United States Patent
Camphausen et al.

(10) Patent No.: US 9,902,762 B2
(45) Date of Patent: *Feb. 27, 2018

(54) MULTIVALENT FIBRONECTIN BASED SCAFFOLD DOMAIN PROTEINS

(71) Applicant: BRISTOL-MYERS SQUIBB COMPANY, Princeton, NJ (US)

(72) Inventors: Ray Camphausen, Wayland, MA (US); Eric Furfine, Concord, MA (US); Irvith M. Carvajal, Brighton, MA (US); H. Nicholas Marsh, Charlestown, MA (US); Marco Gottardis, Princeton, NJ (US); Joan Carboni, Yardley, PA (US); Ricardo Attar, Lawrenceville, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/229,415

(22) Filed: Mar. 28, 2014

(65) Prior Publication Data

US 2014/0349929 A1 Nov. 27, 2014

Related U.S. Application Data

(63) Continuation of application No. 13/533,382, filed on Jun. 26, 2012, now Pat. No. 8,728,483, which is a continuation of application No. 12/470,989, filed on May 22, 2009, now Pat. No. 8,221,765.

(60) Provisional application No. 61/178,395, filed on May 14, 2009, provisional application No. 61/212,982, filed on Apr. 17, 2009, provisional application No. 61/128,651, filed on May 22, 2008.

(51) Int. Cl.

| C07K 14/705 | (2006.01) |
| C07K 14/78 | (2006.01) |
| C07K 14/435 | (2006.01) |
| C07K 16/46 | (2006.01) |
| C07K 16/28 | (2006.01) |
| A61K 38/39 | (2006.01) |
| A61K 38/16 | (2006.01) |
| A61K 38/17 | (2006.01) |
| A61K 38/18 | (2006.01) |
| A61K 47/60 | (2017.01) |
| A61K 39/395 | (2006.01) |
| C07K 14/71 | (2006.01) |
| C07K 14/715 | (2006.01) |
| A61K 39/00 | (2006.01) |

(52) U.S. Cl.
CPC .............. *C07K 14/78* (2013.01); *A61K 38/39* (2013.01); *A61K 47/60* (2017.08); *C07K 16/2863* (2013.01); *A61K 39/3955* (2013.01); *A61K 2039/505* (2013.01); *C07K 14/71* (2013.01); *C07K 14/715* (2013.01); *C07K 2317/31* (2013.01); *C07K 2317/73* (2013.01); *C07K 2317/76* (2013.01); *C07K 2317/92* (2013.01); *C07K 2318/20* (2013.01); *C07K 2319/00* (2013.01)

(58) Field of Classification Search
CPC .............. A61K 2039/505; A61K 38/00; A61K 39/3955; A61K 38/39; A61K 38/17; A61K 38/16; A61K 39/00; A61K 39/395; C07K 16/468; C07K 2317/76; C07K 16/18; C07K 16/2863; C07K 16/28; C07K 16/00

See application file for complete search history.

(56) References Cited

U.S. PATENT DOCUMENTS

| 3,773,919 A | 11/1973 | Boswell et al. |
| 4,863,457 A | 9/1989 | Lee |
| 4,997,652 A | 3/1991 | Wong |
| 5,164,188 A | 11/1992 | Wong |
| 5,235,041 A | 8/1993 | Cappello et al. |
| 5,443,505 A | 8/1995 | Wong et al. |
| 5,501,856 A | 3/1996 | Ohtori et al. |
| 5,514,581 A | 5/1996 | Ferrari et al. |
| 5,516,522 A | 5/1996 | Peyman et al. |
| 5,545,620 A | 8/1996 | Wahl et al. |
| 5,641,648 A | 6/1997 | Ferrari et al. |

(Continued)

FOREIGN PATENT DOCUMENTS

| CA | 2293632 A1 | 12/1998 |
| DE | 19646372 C1 | 6/1997 |

(Continued)

OTHER PUBLICATIONS

Lipscombe et al. Intranasal immunization using the B subunit of the *Escherichia coli* heat-labile toxin fused to an epitope of the Bordetella pertussis P. 69 antigen. Mol Microbiol 5(6): 1385-1392, 1991.*

(Continued)

*Primary Examiner* — Bridget E Bunner
(74) *Attorney, Agent, or Firm* — Nelson Mullins Riley & Scarborough LLP; Jane E. Remillard, Esq.; Christopher L. Frank

(57) ABSTRACT

The present invention relates to multivalent polypeptides comprising at least two fibronectin scaffold domains connected via a polypeptide linker. The invention also relates to multivalent polypeptides for use in diagnostic, research and therapeutic applications. The invention further relates to cells comprising such proteins, polynucleotide encoding such proteins or fragments thereof, and to vectors comprising the polynucleotides encoding the innovative proteins.

10 Claims, 43 Drawing Sheets

(56) References Cited

U.S. PATENT DOCUMENTS

| | | | |
|---|---|---|---|
| 5,766,242 A | 6/1998 | Wong et al. |
| 5,770,697 A | 6/1998 | Ferrari et al. |
| 5,792,742 A | 8/1998 | Gold et al. |
| 5,824,072 A | 10/1998 | Wong |
| 5,869,079 A | 2/1999 | Wong et al. |
| 5,922,676 A | 7/1999 | Pasqualini et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,316,412 B1 | 11/2001 | Ginsberg et al. |
| 6,342,219 B1 | 1/2002 | Thorpe et al. |
| 6,348,333 B1 | 2/2002 | Niwa et al. |
| 6,369,116 B1 | 4/2002 | Wong et al. |
| 6,383,775 B1 | 5/2002 | Duff et al. |
| 6,462,189 B1 | 10/2002 | Koide |
| 6,518,018 B1 | 2/2003 | Szostak et al. |
| 6,524,583 B1 | 2/2003 | Thorpe et al. |
| 6,559,126 B2 | 5/2003 | Tournaire et al. |
| 6,660,492 B1 | 12/2003 | Bode et al. |
| 6,699,493 B2 | 3/2004 | Wong |
| 6,818,418 B1 | 11/2004 | Lipovsek et al. |
| 7,053,701 B2 | 5/2006 | Vice |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 7,858,759 B2 | 12/2010 | Brandt et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 * | 1/2013 | Emanuel ............... C07K 14/78 424/185.1 |
| 8,420,098 B2 | 4/2013 | Camphausen et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 * | 5/2014 | Camphausen ......... C07K 14/78 424/185.1 |
| 8,969,289 B2 | 3/2015 | Gosselin et al. |
| 9,017,655 B2 * | 4/2015 | Emanuel ............... C07K 14/78 424/193.1 |
| 9,234,028 B2 * | 1/2016 | Camphausen ......... C07K 14/78 |
| 9,328,157 B2 | 5/2016 | Chen et al. |
| 9,540,424 B2 | 1/2017 | Gosselin et al. |
| 9,562,089 B2 | 2/2017 | Camphausen et al. |
| 9,605,039 B2 | 3/2017 | Lipovsek et al. |
| 2002/0019517 A1 | 2/2002 | Koide |
| 2002/0061307 A1 | 5/2002 | Whitlow et al. |
| 2002/0142048 A1 | 10/2002 | Sands et al. |
| 2003/0004561 A1 | 1/2003 | Bigus et al. |
| 2003/0104520 A1 | 6/2003 | Ellington et al. |
| 2003/0170753 A1 | 9/2003 | Koide |
| 2003/0186385 A1 | 10/2003 | Koide |
| 2005/0244469 A1 | 11/2005 | Whitcup et al. |
| 2005/0255548 A1 | 11/2005 | Lipovsek et al. |
| 2005/0281861 A1 | 12/2005 | Hughes et al. |
| 2006/0122162 A1 | 6/2006 | Cutler |
| 2006/0182783 A1 | 8/2006 | Hughes et al. |
| 2006/0210604 A1 | 9/2006 | Dadey et al. |
| 2006/0246059 A1 | 11/2006 | Lipovsek et al. |
| 2006/0246549 A1 | 11/2006 | Kurz et al. |
| 2007/0059336 A1 | 3/2007 | Hughes et al. |
| 2007/0071575 A1 | 3/2007 | Rudduck et al. |
| 2007/0071675 A1 | 3/2007 | Wu et al. |
| 2007/0072933 A1 | 3/2007 | Peyman |
| 2007/0082365 A1 | 4/2007 | Lipovsek et al. |
| 2007/0088014 A1 | 4/2007 | Edelman et al. |
| 2007/0099879 A1 | 5/2007 | Sheibani et al. |
| 2007/0160533 A1 | 7/2007 | Chen et al. |
| 2007/0203089 A1 | 8/2007 | Rodrigues et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0193445 A1 | 8/2008 | Goetsch et al. |
| 2008/0220049 A1 | 9/2008 | Chen et al. |
| 2008/0268051 A1 | 10/2008 | Hughes et al. |
| 2009/0176654 A1 | 7/2009 | Cappuccilli et al. |
| 2009/0299040 A1 | 12/2009 | Camphausen et al. |
| 2010/0121033 A1 | 5/2010 | Camphausen et al. |
| 2010/0144599 A1 | 6/2010 | Mendlein et al. |
| 2010/0144601 A1 | 6/2010 | Jacobs et al. |
| 2010/0152063 A1 | 6/2010 | Cappuccilli et al. |
| 2010/0210511 A1 | 8/2010 | Carvajal |
| 2010/0273216 A1 | 10/2010 | Morin et al. |
| 2010/0285000 A1 | 11/2010 | Mamluk |
| 2010/0298541 A1 | 11/2010 | Wu et al. |
| 2010/0310549 A1 | 12/2010 | Chen et al. |
| 2010/0322930 A1 | 12/2010 | Kolbinger et al. |
| 2011/0021746 A1 | 1/2011 | Cappuccilli et al. |
| 2011/0034384 A1 | 2/2011 | Carvajal |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0184212 A1 | 7/2013 | Camphausen et al. |
| 2013/0237684 A1 | 9/2013 | Koide |
| 2013/0267676 A1 | 10/2013 | Koide |
| 2013/0310317 A1 | 11/2013 | Camphausen et al. |
| 2014/0057807 A1 | 2/2014 | Loew et al. |
| 2014/0094595 A1 | 4/2014 | Lipovsek et al. |
| 2015/0152147 A1 | 6/2015 | Gosselin et al. |
| 2015/0252097 A1 | 9/2015 | Camphausen et al. |
| 2015/0259398 A1 | 9/2015 | Emanuel et al. |
| 2016/0152688 A1 | 6/2016 | Camphausen et al. |
| 2016/0297869 A1 | 10/2016 | Chen et al. |

FOREIGN PATENT DOCUMENTS

| | | |
|---|---|---|
| EP | 0430539 A2 | 6/1991 |
| EP | 0488401 A1 | 6/1992 |
| EP | 0654256 A1 | 5/1995 |
| EP | 0962527 A1 | 12/1999 |
| EP | 0985039 B1 | 3/2000 |
| EP | 1137941 B1 | 10/2001 |
| EP | 1266025 B1 | 12/2002 |
| EP | 1477561 B1 | 11/2004 |
| EP | 2141243 A2 | 1/2010 |
| EP | 2379718 B1 | 10/2011 |
| EP | 2385067 A1 | 11/2011 |
| EP | 2439212 A1 | 4/2012 |
| JP | 4-108827 | 4/1992 |
| JP | 2001-500531 | 1/2001 |
| WO | 92/02536 A1 | 2/1992 |
| WO | 93/03172 A1 | 2/1993 |
| WO | 95/11922 A1 | 5/1995 |
| WO | 95/13765 A1 | 5/1995 |
| WO | 96/22391 A1 | 7/1996 |
| WO | 98/12226 A1 | 3/1998 |
| WO | 98/31700 A1 | 7/1998 |
| WO | 98/56915 A2 | 12/1998 |
| WO | 99/51773 A1 | 10/1999 |
| WO | 2000/34784 A1 | 6/2000 |
| WO | 2000/34787 A1 | 6/2000 |
| WO | 2001/07657 A1 | 2/2001 |
| WO | 2001/64942 A1 | 9/2001 |
| WO | 2002/04523 A2 | 1/2002 |
| WO | 2002/32925 A2 | 4/2002 |
| WO | 2002/081497 A2 | 10/2002 |

(56) References Cited

FOREIGN PATENT DOCUMENTS

| | | |
|---|---|---|
| WO | 2002/088171 A2 | 11/2002 |
| WO | 2003/022858 A2 | 3/2003 |
| WO | 2003/072082 A1 | 9/2003 |
| WO | 2003/075840 A2 | 9/2003 |
| WO | 2003/104418 A2 | 12/2003 |
| WO | 2005/056764 A2 | 6/2005 |
| WO | 2006/020258 A2 | 2/2006 |
| WO | 2006/091209 A2 | 8/2006 |
| WO | 2007/012614 A2 | 2/2007 |
| WO | 2007/044688 A1 | 4/2007 |
| WO | 2007/059120 A2 | 5/2007 |
| WO | 2007/062188 A2 | 5/2007 |
| WO | 2007/092537 A2 | 8/2007 |
| WO | 2007/096076 A2 | 8/2007 |
| WO | 2007/121894 A2 | 11/2007 |
| WO | 2008/019290 A2 | 2/2008 |
| WO | 2008/031098 A1 | 3/2008 |
| WO | 2008/048970 A2 | 4/2008 |
| WO | 2008/066752 A2 | 6/2008 |
| WO | 2008/097497 A2 | 8/2008 |
| WO | 2008/108986 A2 | 9/2008 |
| WO | 2008/153745 A2 | 12/2008 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |
| WO | 2009/083804 A2 | 7/2009 |
| WO | 2009/086116 A2 | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |

OTHER PUBLICATIONS

Mao et al. A string of enzymes, purification and characterization of a fusion protein comprising the four subunits of the glucose phosphotransferase system of *Escherichia coli*. J Biol Chem 270(31): 18295-18300, 1995.*

Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).

Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).

Bae, Dong-Goo et al., "Arginine-rich Anti-vascular Endothelial Growth Factor Peptides Inhibit Tumor Growth and Metastasis by Blocking Angiogenesis," The Journal of Biological Chemistry, vol. 275(18):13588-13596 (2000).

Baggio, Rick et al., "Identification of epitope-like consensus motifs using mRNA display," Journal of Molecular Recognition, vol. 15:126-134 (2002).

Baron, Martin et al., "H NMR Assignment and Secondary Structure of the Cell Adhesion Type III Module of Fibronectin," Biochemistry, vol. 31:2068-2073 (1992).

Baron, Martin et al., "Protein modules," TIBS, vol. 16:13-17 (1991).

Batori, Vincent et al., "Exploring the potential of the monobody scaffold: effects of loop elongation on the stability of a fibronectin type III domain," Protein Engineering, vol. 15(12):1015-1020 (2002).

Bianchi, Elisabetta et al., "High Level Expression and Rational Mutagenesis of a Designed Protein, the Minibody," J. Mol. Biol., vol. 236:649-659 (1994).

Boder, Eric T. et al., "Directed evolution of antibody fragments with monovalent femtomolar antigen-binding affinity," PNAS, vol. 97(20):10701-10705 (2000).

Boder, Eric T. et al., "Yeast surface display for screening combinatorial polypeptide libraries," Nature Biotechnology, vol. 15:553-557 (1997).

Boldicke, Thomas et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells from Cord Blood," Stem Cells, vol. 19:24-36 (2001).

Bork, P. et al., "The Immunoglobulin Fold, Structural Classification, Sequence Patterns and Common Core," J. Mol. Biol., vol. 242:309-320 (1994).

Bork, Peer et al., "Go hunting in sequence databases but watch out for the traps," TIG, vol. 12(10):425-427 (1996).

Bork, Peer et al., "Proposed acquisition of an animal protein domain by bacteria," Proc. Natl. Acad. Sci. USA, vol. 89:8990-8994 (1992).

Bork, Peer, "Powers and Pitfalls in Sequence Analysis: The 70% Hurdle," Genome Research, vol. 10:398-400 (2000).

Brenchley, P.E.C. et al., "Angiogenesis in inflammatory joint disease: a target for therapeutic intervention," Clin. Exp. Immunol., vol. 121:426-429 (2000).

Brenner, Steven E., "Errors in genome annotation," TIG, vol. 15(4):132-133 (1999).

Brock, Kenny V. et al., "Nucleotide sequencing of 5' and 3' termini of bovine viral diarrhea virus by RNA ligation and PCR," Journal of Virological Methods, vol. 38:39-46 (1992).

Brown, McKay et al., "Tolerance to Single, but Not Multiple, Amino Acid Replacements in Antibody VH CDR2," The Journal of Immunology, vol. 156:3285-3291 (1996).

Bruzik, James P. et al., "Spliced leader RNAs from lower eukaryotes are trans-spliced in mammalian cells," Nature, vol. 360(6405):692-695 (1992).

Caliceti, Paolo et al., "Pharmacokinetic and biodistribution properties of poly(ethylene glycol)-protein conjugates," Advanced Drug Delivery Reviews, vol. 55:1261-1277 (2003).

Campbell, Iain D. et al., "Building proteins with fibronectin type III modules, Fibronectin type III modules are versatile components of many proteins. Recent structures of module pairs show how these modules are joined together," Structure, vol. 2:333-337 (1994).

Carvalho, Jozelio Freire et al., "Vascular Endothelial Growth Factor (VEGF) in Autoimmune Diseases," Journal of Clinical Immunology, vol. 27(3):246-256 (2007).

Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).

Clackson, Tim et al., "In vitro selection from protein and peptide libraries," TibTech, vol. 12(5):173-184 (1994).

Clackson, Tim et al., "Making antibody fragments using phage display libraries," Nature, vol. 352:624-628 (1991).

Claffey, Kevin P. et al., "Vascular Endothelial Growth Factor, Regulation by Cell Differentiation and Activated Second Messenger Pathways," The Journal of Biological Chemistry, vol. 267(23):16317-16323 (1992).

(56) References Cited

OTHER PUBLICATIONS

Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-lg fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Avidity," Biochemistry, vol. 46:12656-12664 (2007).
Ely, Kathryn R. et al., "Common molecular scaffold for two unrelated RGD molecules," Protein Engineering, vol. 8 (8):823-827 (1995).
Emanuel Stuart L. et al., "Adnectins as a platform for multi-specific targeted biologics: A novel bispecific inhibitor of EGFR and IGF-IR growth factor receptors," Cancer Research, vol. 70(8 Suppl. 1), Poster Presentation No. 2586, 1 page (2010).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Functional activity of a bispecific Adnectin inhibitor to EGFR and IGFR," 2009 AACR Annual Meeting, 1 page, Abstract No. 2813 (2009).
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. ABB78921, "NADH dehydrogenase subunit 6 (mitochondrion) [Homo sapiens]," 2 pages (2008).
GenBank Accession No. CAA26536, Kornblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur. J. Biochem., vol. 161(2):441-453 (1986), 9 pages, (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Gill, Davinder S. et al., "Biopharmaceutical drug discovery using novel protein scaffolds," Current Opinion in Biotechnology, vol. 17:653-658 (2006).
Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth Fill Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hey, Thomas et al., "Artificial, non-antibody binding proteins for pharmaceutical and industrial applications," Trends in Biotechnology, vol. 23(10):514-522 (2005).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Huang, Fei et al., "The Mechanisms of Differential Sensitivity to an Insulin-like Growth Factor-1 Receptor Inhibitor (BMS-536924) and Rationale for Combining with EGFR/HER2 Inhibitors," Cancer Res., vol. 69(1):161-170 (2009).
Huang, Hu et al., "Blockade of VEGFR1 and 2 Suppresses Pathological Angiogenesis and Vascular Leakage in the Eye," PLoS One, vol. 6(6):e21411, 14 pages, doi:10.1371/journal.pone.0021411 (2011).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
Jain, Rakesh K. et al., "Dissecting Tumour Pathophysiology Using Intravital Microscopy," Nature, vol. 2:266-276 (2002).
Jakob, W. et al., "The chick embryo chorioallantoic membrane as a bioassay for angiogenesis factors: Reactions induced by carrier materials," Exp. Path. Bd., vol. 15:241-249 (1978).
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Kohler, G. et al., "Continuous cultures of fused cells secreting antibody of predefined specificity," Nature, vol. 256:495-497 (1975).

(56) References Cited

OTHER PUBLICATIONS

Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The FASEB Journal, vol. 11(9):A1155, Poster No. 1739 (1997).
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).
Kussie, Paul H. et al., "A Single Engineered Amino Acid Substitution Changes Antibody Fine Specificity," Journal of Immunology, vol. 152:146-152 (1994).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).
Lipovsek, D., "Adnectins: engineered target-binding protein therapeutics," Protein Engineering, Design & Selection, vol. 24(1):3-9 (2011).
Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragments of Fibronectin," J. Mol. Biol., vol. 248:611-626 (1995).
Liu, Zhihong et al., "Fine mapping of the antigen-antibody interaction of scFv215, a recombinant antibody inhibiting RNA polymerase II from Drosophila melanogaster," Journal of Molecular Recognition, vol. 12:103-111 (1999).
Lombardo, A. et al., "Conformational flexibility and crystallization of tandemly linked type III modules of human fibronectin," Protein Science, vol. 5:1934-1938 (1996).
Lu, Dan et al., "Tailoring in Vitro Selection for a Picomolar Affinity Human Antibody Directed against Vascular Endothelial Growth Factor Receptor 2 for Enhanced Neutralizing Activity," The Journal of Biological Chemistry, vol. 278(44):43496-43507 (2003).
Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).
Lyden, David et al., "Impaired recruitment of bone-marrow-derived endothelial and hematopoietic precursor cells blocks tumor angiogenesis and growth," Nature Medicine, vol. 7(11):1194-1201 (2001).
Maeda, Hiroshi et al., "SMANCS and polymer-conjugated macromolecular drugs: advantages in cancer chemotherapy," Advanced Drug Delivery Reviews, vol. 46:169-185 (2001).

Main, Alison L. et al., "The Three-Dimensional Structure of the Tenth Type III Module of Fibronectin: An Insight into RGD-Mediated Interactions," Cell, vol. 71:671-678 (1992).
Mamluk, Roni et al., "Anti-tumor effect of CT-322 as an adnectin inhibitor of vascular endothelial growth factor receptor-2," mAbs, vol. 2(2):199-208 (2010).
Mao, Yong et al., "Fibronectin fibrillogenesis, a cell-mediated matrix assembly process," Matrix Biology, vol. 24:389-399 (2005).
Markland, William et al., "Iterative Optimization of High-Affinity Protease Inhibitors Using Phage Display. 1. Plasmin," Biochemistry, vol. 35:8045-8057 (1996).
Markland, William et al., "Iterative Optimization of High-Affinity Protease Inhibitors Using Phage Display. 2. Plasma Kallikrein and Thrombin," Biochemistry, vol. 35:8058-8067 (1996).
Maruyama, Kazuo et al., "Oligo-capping: a simple method to replace the cap structure of eukaryotic mRNAs with oligoribonucleotides," Gene, vol. 138:171-174 (1994).
Matsushima, Ayako et al., "Modification of E. Coli Asparaginase with 2.4-Bis(O-Methoxypolyethylene Glycol)-6-Chloro-S-Triazine(Activated PEG2); Disapperance of Binding Ability Towards Anti-serum and Retention of Enzymic Activity," Chemistry Letters, pp. 773-776 (1980).
Mattheakis, Larry C. et al., "An in vitro polysome display system for identifying ligands from very large peptide libraries," Proc. Natl. Acad. Sci. USA, vol. 91:9022-9026 (1994).
McCleod, D. Scott et al., "Localization of VEGF Receptor-2 (KDR/Flk-1) and Effects of Blocking It in Oxygen-Induced Retinopathy," Investigative Ophthalmology & Visual Science, vol. 43(2):474-482 (2002).
McConnell, Stephen J. et al., "Tendamistat as a Scaffold for Conformationally Constrained Phage Peptide Libraries," J. Mol. Biol., vol. 250:460-470 (1995).
McPherson, Michael et al., "Drug Receptor Identification from Multiple Tissues Using Cellular-Derived mRNA Display Libraries," Chemistry & Biology, vol. 9:691-698 (2002).
Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).
Meissner, Markus et al., "Suppression of VEGFR2 Expression in Human Endothelial Cells by Dimethylfumarate Treatment: Evidence for Anti-Angiogenic Action," Journal of Investigative Dermatology, vol. 131:1356-1364 (2011).
Meyer, Rosana D. et al., "Comparative Structure-Function Analysis of VEGFR-1 and VEGFR-2, What Have We Learned from Chimeric Systems,?" Ann. N. Y. Acad. Sci., vol. 995:200-207 (2003).
Muller, Christoph W. et al., "Structure of the NF-kappaB p50 homodimer bound to DNA," Nature, vol. 373:311-317 (1995).
Muyldermans, Serge, "Single domain camel antibodies: current status," Reviews in Molecular Biotechnology, vol. 74:277-302 (2001).
Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).
NG, Eugene W.M. et al., "Targeting angiogenesis, the underlying disorder in neovascular age-related macular degeneration," Can. J. Ophthalmol., vol. 40:352-368 (2005).
Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), pp. 433-440 and 491-495 (1994).
Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Research, vol. 22(25):5530-5539 (1994).
Nilsen, Timothy W., "Trans-Splicing in Protozoa and Helminths," Infections Agents and Disease, vol. 1:212-218 (1992).
Nord, Karin et al., "A combinatorial library of an alpha-helical bacterial receptor domain," Prot. Eng., vol. 8:601-608 (1995).
Nord, Karin et al., "Binding proteins selected from combinatorial libraries of an alpha-helical bacterial receptor domain," Nature Biotechnology, vol. 15:772-777 (1997).

(56) References Cited

OTHER PUBLICATIONS

Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Patel, Neela et al., "A Selective and Oral Small Molecule Inhibitor of Vascular Epithelial Growth Factor (VEGFR)-2 and VEGFR-1 Inhibits Neovascularization and Vascular Permeability," The Journal of Pharmacology and Experimental Therapeutics, vol. 306(3):838-845 (2003).
Phillips, Anthony J., "The challenge of gene therapy and DNA delivery," Journal of Pharmacy and Pharmacology, vol. 53:1169-1174 (2001).
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Posey, J. et al., "A Phase I Trial of an Anti-KDR (VEGFR2) Chimeric Antibody in Patients with Liver Metastases in Colorectal Cancer (CRC)," Slides from presentation at 2002 American Society of Clinical Oncology (ASCO) Annual Meeting, 20 pages, (2002).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Proescholdt, Martin A. et al., "Vascular Endothelial Growth Factor Is Expressed in Multiple Sclerosis Plaques and Can Induce Inflammatory Lesions in Experimental Allergic Encephalomyelitis Rats," Journal of Neuropathology and Experimental Neurology, vol. 61(10):914-925 (2002).
Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hyperveriable highly constrained epitope via monovalent phagemid display," Gene, vol. 164:243-250 (1995).
Rudikoff, Stuart et al., "Single amino acid substitution altering antigen-binding specificity," Proc. Natl. Acad. Sci. USA, vol. 79:1979-1983 (1982).
Schildbach, Joel F. et al., "Contribution of a single heavy chain residue to specificity of an anti-digoxin monoclonal antibody," Protein Science, vol. 3:737-7419 (1994).
Schildbach, Joel F. et al., "Heavy Chain Positiion 50 Is a Determinant of Affinity and Specificity for the Anti-digoxin Antibody 26-10," The Journal of Biological Chemistry, vol. 268(29):21739-21747 (1993).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).
Shibuya, Masabumi, "Vascular endothelial growth factor receptor-2: Its unique signaling and specific ligand, VEGF-E," Cancer Sci., vol. 94(9):751-756 (2003).
Shima, David T. et al., "The Mouse Gene for Vascular Endothelial Growth Factor," The Journal of Biological Chemistry, vol. 271(7):3877-3883 (1996).
Skolnick, Jeffrey et al., "From genes to protein structure and function: novel applications of computational approaches in the genomic era," TibTech, vol. 18:34-39 (2000).
Smith, George P. et al., "Phage Display," Chem. Rev., vol. 97:391-410 (1997).
Smith, Temple F. et al., "The challenges of genome sequence annotation of 'The devil is in the details,'" Nature Biotechnology, vol. 15:1222-1223 (1997).
Takahashi, Satoru, "Vascular Endothelial Growth Factor (VEGF), VEGF Receptors and Their Inhibitors for Antiangiogenic Tumor Therapy," Biol. Pharm. Bull. vol. 34(12):1785-1788 (2011).
Tang, Lisa et al., "Pharmacokinetic Aspects of Biotechnology Products," Journal of Pharmaceutical Sciences, vol. 93 (9):2184-2204 (2004).
Tischer, Edmund et al., "The Human Gene for Vascular Endothelial Growth Factor," The Journal of Biological Chemistry, vol. 266(18):11947-11954 (1991).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Verheul, H.M.W. et al., "Targeting Vascular Endothelial Growth Factor Blockade: Ascites and Pleural Effusion Formation," The Oncologist, vol. 5(Suppl. 1):45-50 (2000).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, H. et al., "Anti-vascular endothelial growth factor receptor-2 (Flk-1/KDR) antibody suppresses contact hypersensitivity," Experimental Dermatology, vol. 13:671-681 (2004).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol, vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98 (7):3750-3755 (2001).
Xiang, Jim et al., "Study of B72.3 combining sites by molecular modeling and site-directed mutagenesis," Protein Engineering, vol. 13(5):339-344 (2000).
Xu, Lihui et al., "Directed Evolution of High-Affinity Antibody Mimics Using mRNA Display," Chemistry & Biology, vol. 9:933-942 (2002).
Yang, Karen et al., "Tailoring structure-function and pharmacokinetic properties of single-chain Fv proteins by site-specific PEGylation," Protein Engineering, vol. 16(10):761-770 (2003).
Yoshiji, H. et al., "Vascular endothelial growth factor and receptor interaction is a prerequisite for murine hepatic fibrogenesis," Gut, vol. 52:1347-1354 (2003).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).

(56) References Cited

OTHER PUBLICATIONS

Zhou, Tianhong et al., "Development of a multi-drug delivery implant for intraocular management of proliferative vitreoretinopathy," Journal of Controlled Release, vol. 55:281-295 (1998).
Zhu, Z. et al., "Inhibition of human leukemia in an animal model with human antibodies directed against vascular endothelial growth factor receptor 2. Correlation between antibody affinity and biological activity," Leukemia, vol. 17:604-611 (2003).
European Office Action for Application No. 06013825.2, 9 pages, dated Sep. 17, 2008.
European Office Action for Application No. 09167669.2, 7 pages, dated Dec. 28, 2009.
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2011/034998, 10 pages, dated Nov. 6, 2012.
International Preliminary Report on Patentability for Applicaiton No. PCT/US2004/040885, 6 pages, dated Jun. 7, 2006.
International Preliminary Report on Patentability for Application No. PCT/US2011/038013, 9 pages, dated Nov. 27, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US04/40885, 3 pages, dated Feb. 21, 2006.
International Search Report for Application No. PCT/US2009/003192, 8 pages, dated Jun. 1, 2010.
International Search Report for Application No. PCT/US2011/034998, 5 pages, dated Jul. 17, 2012.
International Search Report for Application No. PCT/US2011/038013, 7 pages, dated Jan. 25, 2012.
International Search Report for Application No. PCT/US99/29317, 2 pages, dated Apr. 6, 2000.
Notice of Opposition to European Patent No. 1137941 (Application No. 99 967 261.1), 29 pages, dated May 11, 2010.
Partial European Search Report for Application No. 01981621.4, 5 pages, dated Feb. 25, 2005.
Supplementary European Search Report for Application No. 01913159.8, 3 pages, dated Dec. 21, 2004.
Supplementary European Search Report for Application No. 99967261.1, 3 pages, dated Mar. 6, 2002.
Written Opinion for Application No. PCT/US01/06414, 5 pages, dated Feb. 7, 2002.
U.S. Appl. No. 14/022,827, filed Sep. 10, 2013, Dasa Lipovsek.
U.S. Appl. No. 15/070,572, filed Mar. 15, 2016, Yan Chen.
U.S. Appl. No. 14/954,596, filed Nov. 30, 2015, Ray Camphausen.
U.S. Appl. No. 14/664,290, filed Mar. 20, 2015, Stuart Emanuel.
U.S. Appl. No. 14/552,823, filed Nov. 25, 2014, Michael L. Gosselin.
U.S. Appl. No. 13/699,458, filed Mar. 28, 2013, Ray Camphausen.
U.S. Appl. No. 11/543,316, filed Feb. 12, 2016.
U.S. Appl. No. 11/543,316, filed Jul. 10, 2015.
U.S. Appl. No. 11/543,316, filed Apr. 20, 2011.
U.S. Appl. No. 14/022,827, filed Jan. 13, 2016.
U.S. Appl. No. 14/022,827, filed Jul. 13, 2015.
U.S. Appl. No. 14/022,827, filed Sep. 30, 2014.
U.S. Appl. No. 14/022,827, filed Feb. 11, 2014.
U.S. Appl. No. 14/071,069, filed Dec. 16, 2015.
U.S. Appl. No. 14/071,069, filed Jul. 30, 2015.
U.S. Appl. No. 14/071,069, filed Apr. 16, 2015.
U.S. Appl. No. 14/071,069, filed Dec. 12, 2014.
U.S. Appl. No. 13/892,418, filed Dec. 15, 2014.
U.S. Appl. No. 13/956,952, filed Sep. 1, 2015.
U.S. Appl. No. 13/956,952, filed Mar. 18, 2015.
U.S. Appl. No. 13/956,952, filed Jan. 2, 2015.
U.S. Appl. No. 13/692,555, filed Dec. 23, 2014.
U.S. Appl. No. 14/552,823, filed Mar. 24, 2016.
U.S. Appl. No. 13/699,458, filed Apr. 13, 2016.
U.S. Appl. No. 13/699,458, filed Oct. 27, 2015.
U.S. Appl. No. 13/699,458, filed Jul. 13, 2015.
U.S. Appl. No. 13/699,458, filed Feb. 12, 2015.
U.S. Appl. No. 13/699,458, filed Nov. 7, 2014.
U.S. Appl. No. 15/440,730, filed Feb. 23, 2017, Dasa Lipovsek.
U.S. Appl. No. 15/404,749, filed Jan. 12, 2017, Ray Camphausen.
U.S. Appl. No. 15/363,724, filed Nov. 29, 2016, Michael L. Gosselin.
U.S. Appl. No. 15/385,222, filed Dec. 20, 2016, Ray Camphausen.
U.S. Appl. No. 11/543,316, filed Nov. 16, 2016.
U.S. Appl. No. 13/699,458, filed Sep. 29, 2016.
U.S. Appl. No. 14/022,827, filed Jan. 31, 2017.
U.S. Appl. No. 14/552,823, filed Aug. 31, 2016.
U.S. Appl. No. 14/664,290, filed Jan. 13, 2017.
U.S. Appl. No. 14/664,290, filed Sep. 20, 2016.
U.S. Appl. No. 15/070,572, filed Nov. 9, 2016.

* cited by examiner

| CONSTRUCT DESCRIPTION | DSC | MASS SPEC | |
|---|---|---|---|
| | | THEORETICAL MW | EXPERIMENTAL |
| 385A08-Fn-V2B (with his-tag) | 51.49<br>Soluble prep<br>In NaOAc, pH4.5 | 23,260.16 Da<br>(desMet) | 23,260 Da<br>(desMet) |
| 385A08-Fn-V2B-Cys (with his-tag) | 46.77/55.52<br>refold<br>In NaOAc, pH4.5 | 23,407.43 Da | 23581 Da |
| 385A08-GS10-V2B (with his-tag) | ND | 24,040 Da | 24,040 Da |

FIGURE 4

| MOLECULAR FORM | COLUMN 1<br>IGF-IR KD<br>(pM) (n=1) | COLUMN 2<br>Ba/F3 IC50<br>(nM) | COLUMN 3<br>Rh41 IC50<br>(nM)(n=1) |
|---|---|---|---|
| 385A08-Fn-V2B | ~300 | 1.0 | 26 |
| 385A08-Fn-V2B-Cys |  | 1.3 | 33 |
| 385A08-GS5-V2B | ~300 | 1.0 | 40 |
| 385A08-GS10-V2B | ~300 | 1.2 | 27 |
| V2B-Fn-385A08-Cys |  | 0.8 | 6 |
| V2B-Fn-385A08 | ~200 | 2.2 |  |
| V2B-GS5-385A08 | ~200 | 2.0 |  |
| V2B-GS10-385A08 | ~200 | 1.9 |  |
| Peg-V2Bshort |  | 10 | >50 |
| V2B |  | 7.0 |  |
| AT-577 | 76 |  |  |
| AT580-PEG20-AT580 |  | INACTIVE | 0.07 |

FIGURE 8

| CONSTRUCT | CAPTURED IGF1R-Fc ||| IMMOBILIZED VEGFR2-Fc |||
|---|---|---|---|---|---|---|
| | ka (1/Ms) | kd (1/s) | KD (M) | ka (1/Ms) | Kd (1/s) | KD (M) |
| 385A08-GS10-V2B (with his-tag) | 7.72E+06 | 3.08E-04 | ~ 40 pM | 4.14E+05 | 1.93E-04 | .5 nM |
| V2B-GS10-385A08 (with his-tag) | 4.18E+06 | 2.04E-04 | ~ 50 pM | 3.82E+05 | 2.22E-04 | .6 nM |
| 385A08-Fn-V2B-Cys (with linear PEG & his-tag) | 2.00E+05 | 2.33E-04 | 1.2 nM | 1.06E+04 | 1.49E-04 | 14 nM |

FIGURE 9

KINETIC PARAMETERS FOR VI TANDEM LOTS

| Sample ID | Construct 385A08-Fn-V2B-cys (with branched PEG) | CAPTURED IGF1R-Fc | | | IMMOBILIZED VEGFR2-Fc | | |
|---|---|---|---|---|---|---|---|
| | | ka (1/Ms) | kd (1/s) | KD (M) | ka (1/Ms) | kd (1/s) | KD (M) |
| Batch 1 | with his | 2.99E+05 | 2.5E-04 | 8.31E-10 | 8.6E+03 | 9.49E-05 | 1.10E-08 |
| Batch 2 | with his | 4.80E+05 | 2.23E-04 | 4.65E-10 | 2.18E+04 | 1.30E-04 | 5.96E-09 |
| Batch 3 | with his | 2.77E+05 | 2.38E-04 | 8.57E-10 | 7.53E+03 | 9.46E-05 | 1.26E-08 |
| Batch 4 | without his | 2.75E+05 | 2.70E-04 | 9.82E-10 | 6.67E+03 | 1.15E-04 | 1.72E-08 |
| Batch 5 | without his | 2.44E+05 | 2.53E-04 | 1.04E-09 | 1.30E+04 | 7.49E-05 | 5.8E-09 |
| | Average | 3.15E+05 | 2.47E-04 | 8.35E-10 | 1.15E+04 | 1.02E-04 | 1.05E-08 |
| | Std Dev | 0.94E+05 | 0.18E-04 | 2.24E-10 | 0.62E+04 | 0.21E-04 | 0.48E-08 |

FIGURE 10

| MOLECULE | IC$_{50}$, nM | |
|---|---|---|
| | Rh41 | HMVEC-L |
| AT-577 | 132 ± 1.1 | >1000 |
| MAB391 | 0.1 ± 0.1 | >1000 |
| Peg-V2Bshort | >1000 | 68 ± 14 |
| Bevacizumab | >1000 | 8.6 ± 7 |
| SGE (Non binding $^{10}$Fn3-based protein) | >50 | >50 |
| 385A08-Fn-V2B | 27 ± 7 | 21 ± 7 |
| 385A08-Fn-V2B-cys | 32 ± 1.2 | 27 ± 14 |
| 385A08-GS5-V2B | 43 ± 3.8 | 29 ± 22 |
| 385A08-GS10-V2B | 28 ± 4.1 | 28 ± 14 |
| V2B-Fn-385A08-Cys | 9.5 ± 4 | 6.9 ± 5.4 |
| V2B-Fn-385A08 | 22 | 15 ± 12 |
| V2B-GS5-385A08 | 30 | 13 ± 10 |
| V2B-GS10-385A08 | 23 | 19 ± 17 |

FIGURE 13

Summary of V-I Tandem in vitro Activity

| MOLECULE | IC$_{50}$ Range, nM | |
|---|---|---|
| | NCI-H929 | BaF3 |
| MAB391 (mono-specific IGF-IR antibody) | 0.1 – 0.8 | INACTIVE |
| AT580-PEG40 (mono-specific IGF-IR binder) | 0.5 – 2 | INACTIVE |
| Peg-V2Bshort (mono-specific VEGFR2 binder) | INACTIVE | 8 – 40 |
| Pegylated 385A08-Fn-V2B-Cys (with his-tag) | 1.8 | ~10 |
| Pegylated 385A08-Fn-V2B-Cys (without his-tag) | 1.3 | ~10 |

FIGURE 14

| REAGENT | HMVEC-L |
|---|---|
| | $IC_{50}$ nM |
| Peg-V2Bshort | 48 ± 31 |
| MAB391 | >200 |
| AT577 | >1000 |
| AT-580-PEG40 | >400 |
| Pegylated, his tagged 385A08-Fn-V2B-cys | 137 ± 65 |
| Non-pegylated, His tagged 385A08-Fn-V2B-cys | 147 ± 59 |
| Pegylated, non-his tagged 385A08-Fn-V2B-cys | 106 ± 70 |
| Non-pegylated, non-his tagged 385A08-Fn-V2B-cys | 90 ± 45 |
| Pegylated, non-his tagged 385A08-Fn-V2B-cys | 167 ± 56 |
| SGE (Non binding $^{10}$Fn3-based protein) | >200 |

| REAGENT | IC50 Value (nM) |
|---|---|
| Peg-V2Bshort | 3.9 ± 0.1 |
| AT-580-PEG40 | >100 |
| 385A08-Fn-V2B-cys with PEG & his tag | 4.4 ± 2.8 |
| 385A08-Fn-V2B-cys with his tag (no PEG) | 10.1 ± 1.5 |
| 385A08-Fn-V2B-cys with PEG (no his tag) | 8.9 ± 0.8 |
| SGE (Non-binding $^{10}$Fn3-based protein) | >100 |

FIGURE 21

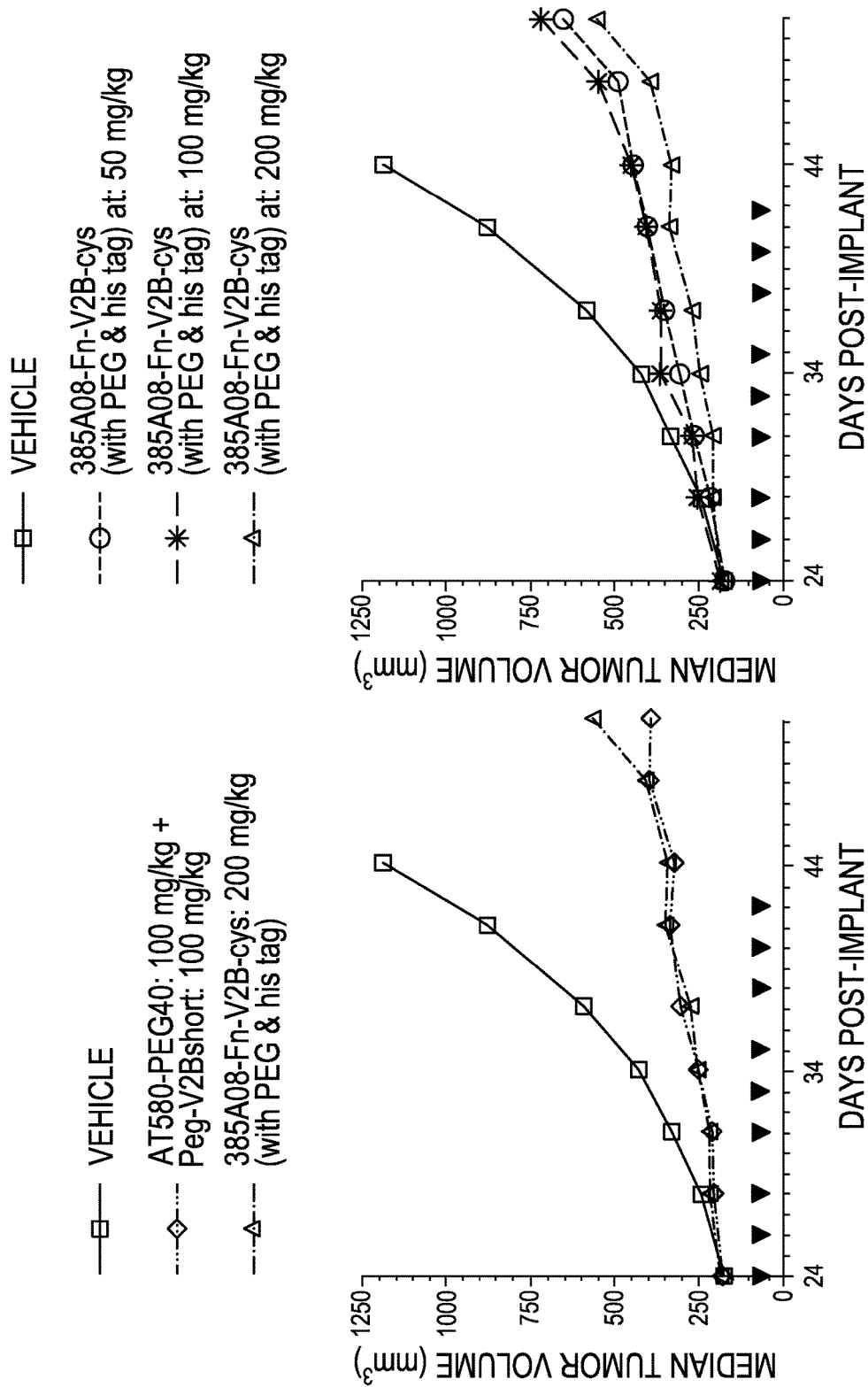

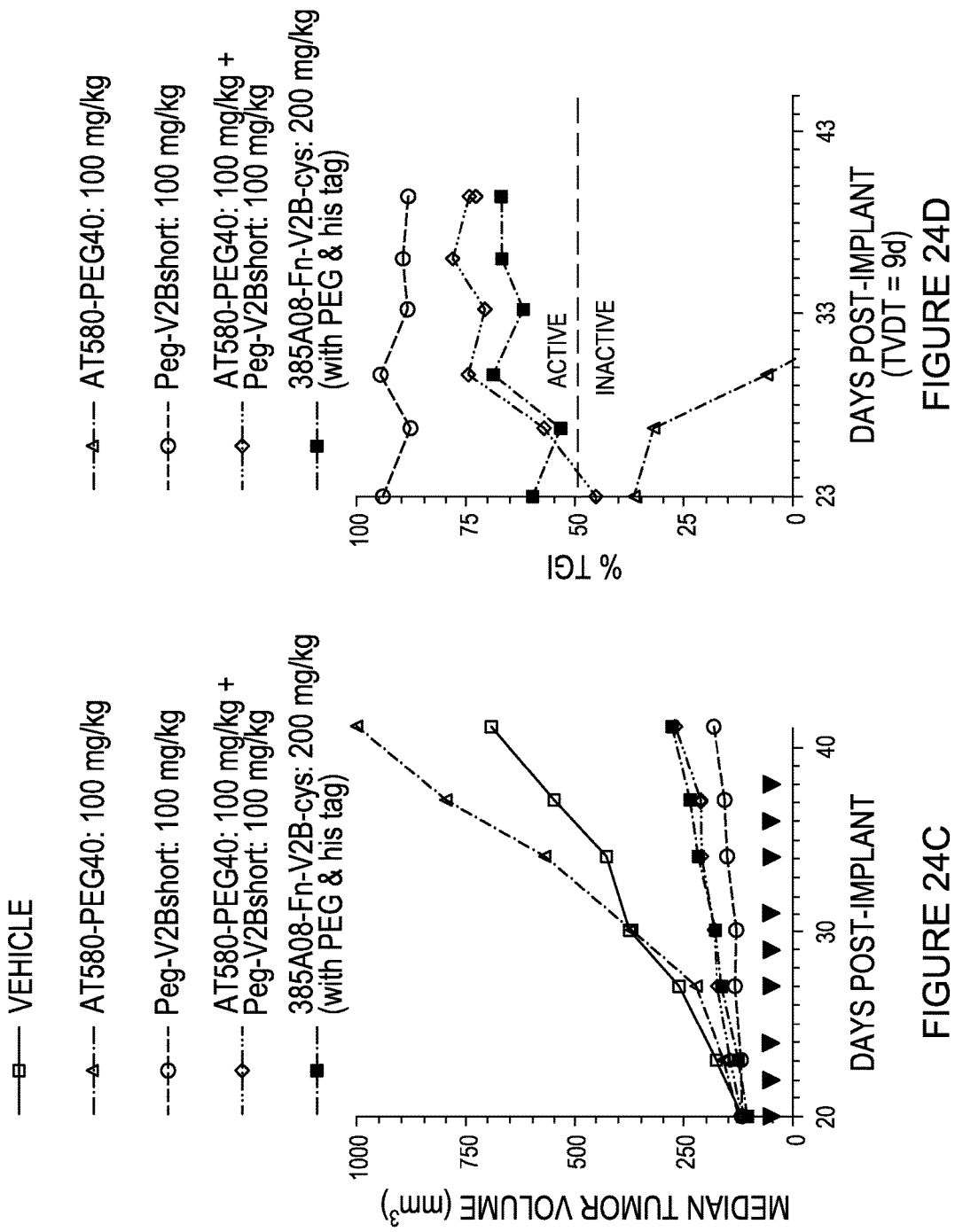

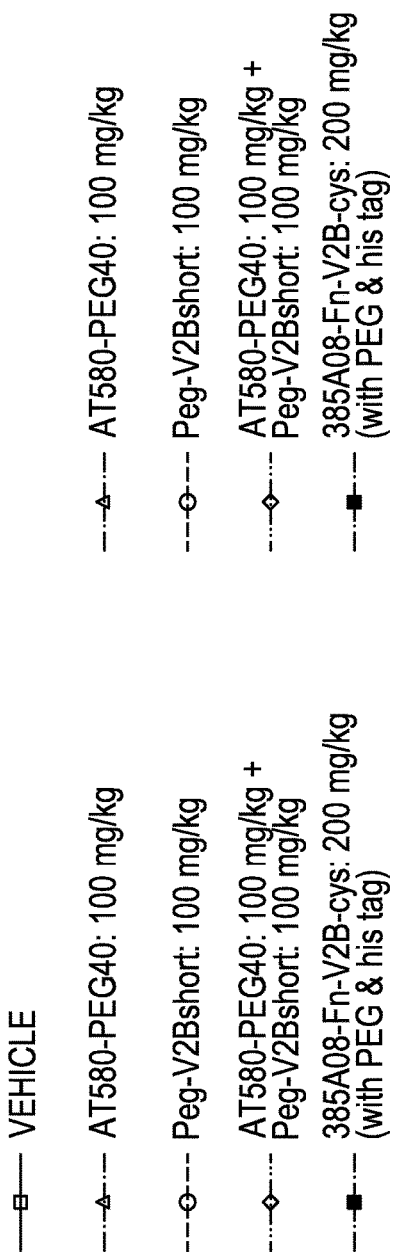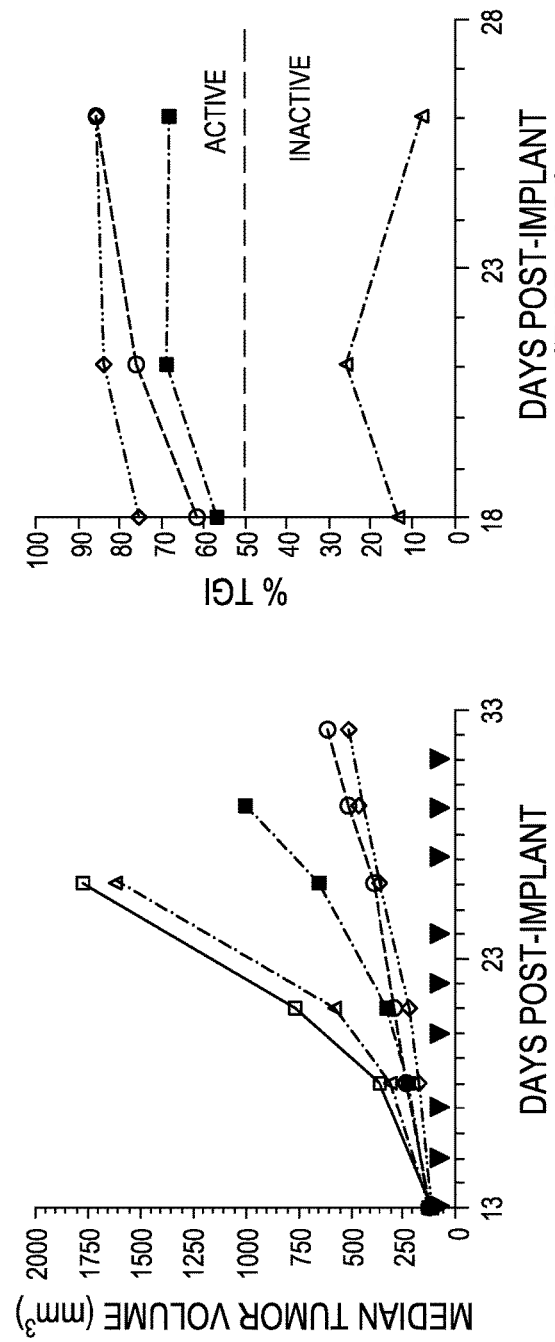
FIGURE 25C
FIGURE 25D

| | IV | | IP | |
|---|---|---|---|---|
| Dose (mg/kg) | 5 | 50 | 5 | 50 |
| AUCtot (µM.h) | 33.8 ± 4.4 | 302.0 ± 50.1 | 27.9 ± 4.3 | 318.6 ± 22.5 |
| CLTp (mL/min/kg) | 0.11 ± 0.01 | 0.12 ± 0.02 | - | - |
| Vss (L/kg) | 0.10 ± 0.02 | 0.12 ± 0.02 | - | - |
| MRT (h) | 15.2 ± 0.8 | 16.8 ± 0.2 | 20.3 ± 0.5 | 24.2 ± 1.2 |
| T1/2 (h) | 13.0 ± 0.5 | 21.4 ± 2.8 | 14.8 ± 0.9 | 17.5 ± 1.3 |
| Cmax (µM) | - | - | 1.5 ± 0.17 | 14.4 ± 4.9 |
| Tmax (h) | - | - | 1.4 ± 0.8 | 3.0 ± 2.0 |
| F (%) | | | 83.1 | 105.8 |

FIGURE 27

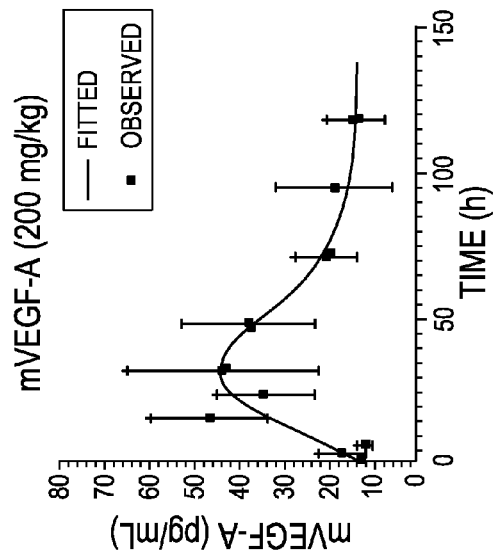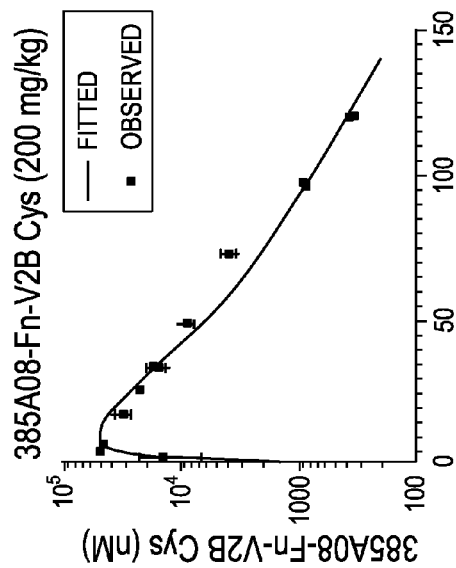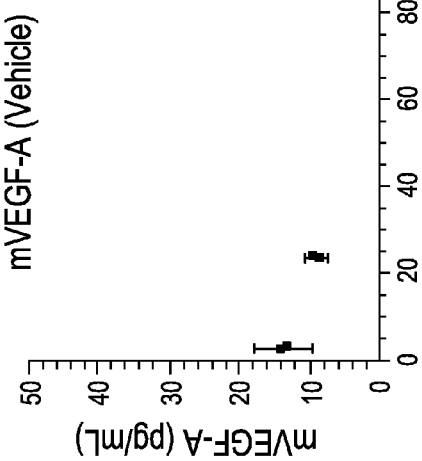
FIGURE 28C
FIGURE 28D
FIGURE 28E

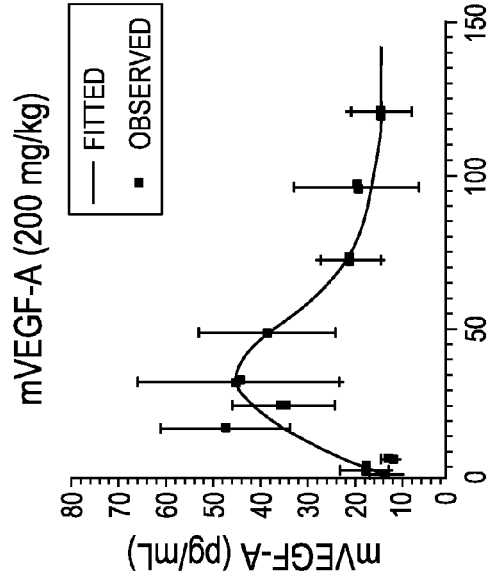
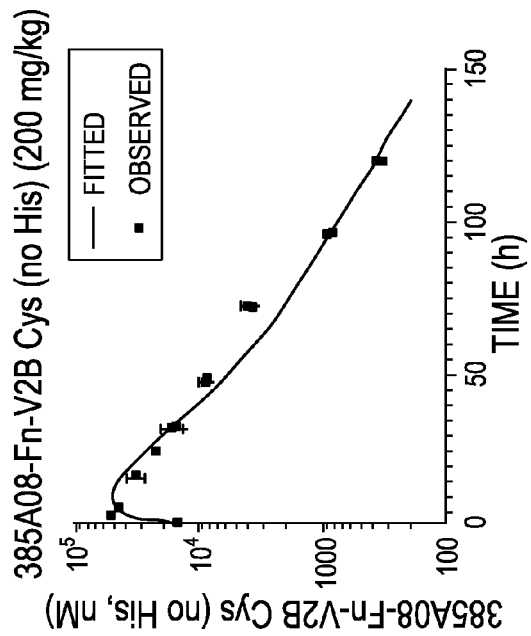

|  | IV (N = 2) | IV (N = 2) |
|---|---|---|
| Dose (mg/kg) | 3 | 30 |
| AUCtot (µM.h) | 74.2 (73.6, 74.8) | 959.6 (833.3, 1085.8) |
| CLTp (mL/min/kg) | 0.029 (0.029, 0.029) | 0.023 (0.026, 0.020) |
| Vss (L/kg) | 0.060 (0.056, 0.063) | 0.077 (0.078, 0.077) |
| MRT (h) | 34.5 (31.9, 37.2) | 57.9 (50.8, 65.0) |
| T1/2 (h) | 23.2 (21.5, 24.9) | 42.7 (37.4, 48.0) |

FIGURE 30

|  | IV (N = 3) | IV (Re-dosed, N = 3) |
| --- | --- | --- |
| Dose (mg/kg) | 3 | 3 |
| AUCtot (µM.h) | 55.0 ± 10.8 | 84.1 ± 10.9 |
| CLTp (mL/min/kg) | 0.041 ± 0.009 | 0.027 ± 0.004 |
| Vss (L/kg) | 0.10 ± 0.02 | 0.047 ± 0.002 |
| MRT (h) | 42.2 ± 1.4 | 30.0 ± 3.7 |
| T1/2 (h) | 29.4 ± 0.8 | 21.3 ± 2.8 |

FIGURE 32

MULTIVALENT FIBRONECTIN BASED SCAFFOLD DOMAIN PROTEINS

RELATED APPLICATIONS

This application is a continuation of U.S. patent application Ser. No. 13/533,382, filed Jun. 26, 2012 (issued as U.S. Pat. No. 8,728,483), which is a continuation of U.S. patent application Ser. No. 12/470,989, filed May 22, 2009 (issued as U.S. Pat. No. 8,221,765), which claims the benefit of U.S. Provisional Patent Application Nos. 61/128,651, filed May 22, 2008, 61/212,982, filed Apr. 17, 2009, and 61/178,395, filed May 14, 2009. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created Mar. 28, 2014, is named MXI_521CN2_Sequence_listing.txt, and is 64,668 bytes in size.

FIELD OF THE INVENTION

The present invention relates to multivalent fibronectin based scaffold domains for use in diagnostic, research and therapeutic applications. The invention further relates to cells comprising such proteins, polynucleotide encoding such proteins or fragments thereof, and to vectors comprising the polynucleotides encoding the innovative proteins.

INTRODUCTION

Fibronectin based scaffolds are a family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins™ (Adnexus, a Bristol-Myers Squibb R&D Company).

Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperoning, and carbohydrate-binding domains. For reviews see Bork & Doolittle, Proc Natl Acad Sci USA. 1992 Oct. 1; 89(19):8990-4; Bork et al., J Mol Biol. 1994 Sep. 30; 242(4):309-20; Campbell & Spitzfaden, Structure. 1994 May 15; 2(5):333-7; Harpez & Chothia, J Mol Biol. 1994 May 13; 238(4):528-39).

Fibronectin type III (Fn3) domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. Any or all of loops AB, BC, CD, DE, EF and FG may participate in target binding. The BC, DE, and FG loops are both structurally and functionally analogous to the complementarity determining regions (CDRs) from immunoglobulins. U.S. Pat. No. 7,115,396 describes Fn3 domain proteins wherein alterations to the BC, DE, and FG loops result in high affinity TNFα binders. U.S. Publication No. 2007/0148126 describes Fn3 domain proteins wherein alterations to the BC, DE, and FG loops result in high affinity VEGFR2 binders.

It would be advantageous to obtain improved fibronectin domain scaffold proteins for both therapeutic and diagnostic purposes. The present disclosure provides such improved proteins.

SUMMARY OF THE INVENTION

One aspect of the application provides for multivalent polypeptides comprising an N-terminal domain comprising a first fibronectin type III tenth domain ($^{10}$Fn3) that binds to a first target molecule with a $K_D$ of less than 500 nM and a C-terminal domain comprising a second $^{10}$Fn3 that binds to a second target molecule with a $K_D$ of less than 500 nM. In some embodiments, first and second $^{10}$Fn3 domains are linked via a polypeptide linker, such as, for example, a polypeptide having from 1-100, 1-50, 1-20, 1-10, 5-50, 5-20, 5-10, 10-50, or 10-20 amino acids. In some embodiments, first and second $^{10}$Fn3 domains are linked via a polypeptide selected from a glycine-serine based linker, such as SEQ ID NOS: 21 and 22. In some embodiments, the first and second $^{10}$Fn3 domains are linked via the polypeptide depicted in SEQ ID NO: 20. In some embodiments, first and second $^{10}$Fn3 domains are linked via a polypeptide selected from a glycine-proline based linker, such as SEQ ID NOS: 32, 33, and 34. In some embodiments, first and second $^{10}$Fn3 domains are linked via a polypeptide selected from a proline-alanine based linker, such as SEQ ID NOS: 60, 61 and 62.

The $^{10}$Fn3 domains each comprise a loop, AB; a loop, BC; a loop, CD; a loop, DE; a loop, EF; and a loop, FG and each, independently, have at least one loop selected from loop BC, DE, and FG with an altered amino acid sequence relative to the sequence of the corresponding loop of the human $^{10}$Fn3 domain. The $^{10}$Fn3 domains each comprise an amino acid sequence that is at least 50, 60, 70, or 80% identical to the naturally occurring human $^{10}$Fn3 domain represented by SEQ ID NO: 1.

In some embodiments, the first $^{10}$Fn3 domain binds to a first target molecule with a $K_D$ of less than 100 nM and the second $^{10}$Fn3 domain binds to a second target molecule with a $K_D$ of less than 100 nM. In some embodiments, the first target molecule and the second target molecule are the same. In some embodiments, the first target molecule and the second target molecule are different. In some embodiments, the first target molecule is IGF-IR and the second target molecule is VEGFR2. In some embodiments, the first target molecule is VEGFR2 and the second target molecule is IGF-IR.

In some embodiments, at least two loops of the $^{10}$Fn3 domains are altered. In some embodiments, loop BC and loop FG have an altered amino acid sequence relative to the sequence of the corresponding loop of the human $^{10}$Fn3 domain. In some embodiments, at least three loops of the $^{10}$Fn3 domains are altered. In some embodiments, at least two loops of the $^{10}$Fn3 domain bind a target molecule. In some embodiments, three loops of the $^{10}$Fn3 domain bind a target molecule.

In some embodiments, the first and/or second $^{10}$Fn3 domain is linked at its C-terminus to an amino acid sequence selected from: SEQ ID NO: 17, 18, 19, 50, 51, 52, 71 or 72 or E, EI, EID, ES, EC, EGS, or EGC. In some embodiments, the first $^{10}$Fn3 domain is linked at its C-terminus to the amino acid sequence of SEQ ID NO: 19 or 50, or E, EI, or EID. In some embodiments, the second $^{10}$Fn3 domain is linked at its C-terminus to the amino acid sequence of SEQ ID NO: 17, 18, 51, 52, 71 or 72.

In some embodiments, multivalent polypeptides are provided comprising the amino acid sequence at least 70, 80, 90, 95, or 100% identical to any one of SEQ ID NOS: 8-15, 29-31 and 63-70.

In some embodiments, the multivalent polypeptide further comprises one or more pharmacokinetic (PK) moieties selected from: a polyoxyalkylene moiety, a human serum albumin binding protein, sialic acid, human serum albumin, transferrin, IgG, an IgG binding protein, and an Fc fragment. In some embodiments, the PK moiety is the polyoxyalkylene moiety and said polyoxyalkylene moiety is polyethylene glycol (PEG).

In some embodiments, the PEG moiety is covalently linked to the multivalent polypeptide via a Cys or Lys amino acid. In some embodiments, the PEG is between about 0.5 kDa and about 100 kDa.

In some embodiments, the PK moiety improves one or more pharmacokinetic properties of the polypeptides, e.g., bioavailability, serum half-life, in vivo stability, and drug distribution. In some embodiments, the PK moiety increases the serum half-life of the multivalent polypeptide by at least 20, 30, 40, 50, 70, 90, 100, 120, 150, 200, 400, 600, 800% or more relative to the multivalent polypeptide alone. In some embodiments, the multivalent polypeptide further comprising a PK moiety has a serum in vivo half-life of at least 1, 2, 3, 4, 5, 6, 7, 8, 9, 10, 11, 12, 13, or 14 days.

In some embodiments, the PK moiety and the $^{10}$Fn3 domain are linked via at least one disulfide bond, a peptide bond, a polypeptide, a polymeric sugar, or a polyethylene glycol moiety. In some embodiments, the PK moiety and the $^{10}$Fn3 domain are linked via a polypeptide comprising the amino acid sequence of SEQ ID NOS: 17, 18, or 20.

In some embodiments, the multivalent polypeptide further comprises a binding moiety. In some embodiments, the multivalent polypeptide further comprises an antibody moiety. In some embodiments, the antibody moiety is less than 50 KDa. In some embodiments, the antibody moiety is less than 40 KDa. In some embodiments, the antibody moiety is a single chain Fvs (scFvs), Fab fragment, Fab' fragment, F(ab')$_2$, disulfide linked Fv (sdFv), Fv, diabody, or whole antibody. In some embodiments, the antibody moiety is a single domain antibody. In some embodiments, the antibody moiety binds a human protein. In some embodiments the antibody moiety binds IGF-IR, FGFR1, FGFR2, FGFR3, FGFR4, c-Kit, human p185 receptor-like tyrosine kinase, HER2, HER3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human alpha4beta7 integrin, human GPIIb-IIIa integrin, stem cell factor (SCF), EGFR, or human CD3.

In some embodiments, the multivalent polypeptide further comprises a derivative of lipocalin; a derivative of tetranectin; an avimer; or a derivative of ankyrin. In some embodiments, the multivalent polypeptide binds a human protein. In some embodiments the multivalent polypeptide binds IGF-IR, FGFR1, FGFR2, FGFR3, FGFR4, c-Kit, human p185 receptor-like tyrosine kinase, HER2, HER3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human alpha4beta7 integrin, human GPIIb-IIIa integrin, stem cell factor (SCF), EGFR, or human CD3.

In some embodiments, the multivalent polypeptide further comprises a binding moiety linked via at least one disulfide bond, a peptide bond, a polypeptide, a polymeric sugar, or a polyethylene glycol moiety (PEG). In some embodiments, the PEG is between about 0.5 kDa and about 100 kDa. In some embodiments, the PEG is conjugated to the polypeptide and the binding moiety via a Cys or Lys residue.

In one aspect, the application provides a multivalent polypeptide that has been deimmunized to remove one or more T-cell epitopes. In one aspect, the application provides a multivalent polypeptide that has been deimmunized to remove one or more B-cell epitopes.

In one aspect, the application provides a multivalent polypeptide wherein the $^{10}$Fn3 domains are selected by the method comprising a) producing a population of candidate nucleic acid molecules, each comprising a candidate fibronectin type III ($^{10}$Fn3) domain sequence which differs from human $^{10}$Fn3 domain coding sequence, said nucleic acid molecules each comprising a translation initiation sequence and a start codon operably linked to said candidate $^{10}$Fn3 domain coding sequence and each being operably linked to a nucleic acid-puromycin linker at the 3' end; b) in vitro translating said candidate $^{10}$Fn3 domain coding sequences to produce a population of candidate nucleic acid-$^{10}$Fn3 fusions; c) contacting said population of candidate nucleic acid-$^{10}$Fn3 fusions with a target molecule; and d) selecting a nucleic acid-$^{10}$Fn3 fusion, the protein portion of which has a binding affinity or specificity for the target molecule that is altered relative to the binding affinity or specificity of said human $^{10}$Fn3 for the target molecule. In some embodiments, the selected nucleic acid-$^{10}$Fn3 fusion is further optimized by altering one or more nucleic acid residues and rescreening the fusion with the target molecule to select for improved binders. In some embodiments the candidate nucleic acid molecule is RNA. In some embodiments the candidate nucleic acid molecule is DNA.

In one aspect, the application provides pharmaceutically acceptable compositions comprising a multivalent polypeptide. In some embodiments, the composition is essentially endotoxin free. In some embodiments, the composition is substantially free of microbial contamination making it suitable for in vivo administration. The composition may be formulated, for example, for IV, IP or subcutaneous administration.

In another aspect, the application provides a nucleic acid encoding a multivalent polypeptide as described herein. Vectors containing polynucleotides for such proteins are included as well. Suitable vectors include, for example, expression vectors. A further aspect of the application provides for a cell, comprising a polynucleotide, vector, or expression vector, encoding a multivalent polypeptide. Sequences are preferably optimized to maximize expression in the cell type used. Preferably, expression is in *E. coli*. Multivalent polypeptides can also be expressed, for example, in eukaryotic microbes, including yeast (e.g., *pichia* or *cerevisiae*) or blue green algae. Yeast cells can be engineered to produce desired glycosylations. The cells of the invention can be a mammalian cell. In one aspect, the mammalian cell can be engineered to produce desired glycosylations. In one aspect, the cell expresses a fibronectin based scaffold protein. In one aspect, the polynucleotides encoding fibronectin based scaffold proteins are codon optimized for expression in the selected cell type. Also provided are methods for producing a multivalent polypeptide as described herein, comprising culturing a host cell comprising a nucleic, vector, or expression vector, comprising a nucleic acid encoding the multivalent polypeptide and recovering the expressed multivalent polypeptide from the culture.

BRIEF DESCRIPTION OF THE FIGURES

FIG. 8. VEGFR2/IGF-IR tandems are equipotent in cells to VEGFR2 or IGF-IR individual binders. Constructs were tested in Biacore assay for binding to IGF-IR, and in Ba/F3 and Rh41 assays to determine IC50 (see Examples 5 and 7). The sequences of the molecular forms are described in Example 1. As shown: 'GS5' (SEQ ID NO: 21) and 'GS10' (SEQ ID NO: 22).

FIG. 9. Certain V/I $^{10}$Fn3-based binders were evaluated for their kinetic behavior towards IGF-IR and VEGFR2. As shown: 'GS10' (SEQ ID NO: 22).

FIG. 10. His-tag and non-his-tag versions of the pegylated construct 385A08-Fn-V2B-cys were evaluated for their kinetic behavior towards IGF-IR and VEGFR2.

FIG. 13. V/I $^{10}$Fn3-based binders were evaluated in the cell based assays Rh41 and HMVEC-L. As shown: 'GS5' (SEQ ID NO: 21) and 'GS10' (SEQ ID NO: 22).

FIG. 14. Selected constructs, including his-tag and non-his-tag of the pegylated construct 385A98-Fn-V2B-Cys were evaluated for their activity in the cell based assays NCI-H929 and Ba/F3, compared to controls.

FIG. 18. Cellular Proliferation Assay: Effect of various V/I $^{10}$Fn3-based binders in HMVEC cells after exposure for 72 hrs.

FIG. 21. Effect of various constructs on calcium release in HMVEC-L cells after exposure for 1 hr. Cells were serum-starved overnight in EBM media and then incubated in the presence of increasing amounts of various constructs for 1 hour. The cells were stimulated with 50 ng/ml VEGF ligand. Ca$^{2+}$ flux was measured 60 seconds after ligand addition.

FIG. 22A. Growth curve following a 3×wk×3 regimen. FIG. 22B. Percent growth inhibition plot demonstrating greater than 50% TGI over one TVDT when compared to vehicle treated group. (▼) Indicates dosing regimen.

FIGS. 23A-23D. Antitumor activity of pegylated, his-tagged 385A08-Fn-V2B-cys in the RH-41 tumor xenograft model at multiple dose levels. FIGS. 23A, 23B, 23C, and 23D list the indicated dose levels of each agent. (▼) Indicates dosing regimen.

FIGS. 24A-24D. Antitumor activity of pegylated, his-tagged 385A08-Fn-V2B-cys in the A549 tumor xenograft lung model at multiple dose levels. The indicated dose levels are shown in FIGS. 24A and 24C with corresponding % TGI in FIGS. 24B and 24D. (▼) Indicates dosing regimen.

FIGS. 25A-25D. Antitumor activity of pegylated, his-tagged 385A08-Fn-V2B-cys in the GEO tumor xenograft colon model at multiple dose levels. The indicated dose levels are shown in FIGS. 25A and 25C with corresponding % TGI in FIGS. 25B and 25D. (▼) Indicates dosing regimen.

FIG. 27. Pharmacokinetic parameters of 385A08-Fn-V2B-cys (with his).

FIGS. 28A-28E. Fitted vs. observed plasma concentration-time profiles of 385A08-Fn-V2B-cys (with his) and mVEGF-A after IP administration of 20 and 200 mg/kg to nude mice bearing the A673 tumor. FIG. 28A: 385A08-Fn-V2B-cys (with his) (20 mg/kg); FIG. 28B: mVEGF-A (20 mg/kg); FIG. 28C: 385A08-Fn-V2B-cys (with his) (200 mg/kg); FIG. 28D: mVEGF-A (200 mg/kg); FIG. 28E: mVEGF-A (vehicle).

FIGS. 29A-29E. Fitted vs. observed plasma concentration-time profiles of 385A08-Fn-V2B-cys (no his) and mVEGF-A after IP administration of 20 and 200 mg/kg to nude mice bearing the A673 tumor. FIG. 29A: 385A08-Fn-V2B-cys (no His) (20 mg/kg); FIG. 29B: mVEGF-A (20 mg/kg); FIG. 29C: 385A08-Fn-V2B-cys (no His) (200 mg/kg); FIG. 29D: mVEGF-A (200 mg/kg); FIG. 29E: mVEGF-A (vehicle).

FIG. 30. Pharmacokinetic parameters of 385A08-Fn-V2B-cys (with his) in monkeys.

FIG. 31A: 385A08-Fn-V2B-cys (with His) (3 mg/kg; monkey #1); FIG. 31B: hVEGF-A (3 mg/kg; monkey #1); FIG. 31C: 385A08-Fn-V2B-cys (with His) (3 mg/kg; monkey #2); FIG. 31D: hVEGF-A (3 mg/kg; monkey #2); FIG. 31E: 385A08-Fn-V2B-cys (with His) (30 mg/kg; monkey #1); FIG. 31F: hVEGF-A (30 mg/kg; monkey #1); FIG. 31G: 385A08-Fn-V2B-cys (with His) (30 mg/kg; monkey #2); FIG. 31H: hVEGF-A (30 mg/kg; monkey #2).

FIG. 32. Pharmacokinetic parameters of 385A08-Fn-V2B-cys (non-his tagged) in monkeys.

FIG. 33A: 385A08-Fn-V2B-cys (no His) (3 mg/kg; monkey #1); FIG. 33B: hVEGF-A (3 mg/kg; monkey #1); FIG. 33C: 385A08-Fn-V2B-cys (no His) (3 mg/kg; monkey #2); FIG. 33D: hVEGF-A (3 mg/kg; monkey #2); FIG. 33E: 385A08-Fn-V2B-cys (no His) (3 mg/kg; monkey #3); FIG. 33F: hVEGF-A (3 mg/kg; monkey #3).

DETAILED DESCRIPTION OF THE INVENTION

Definitions

Figure 1:
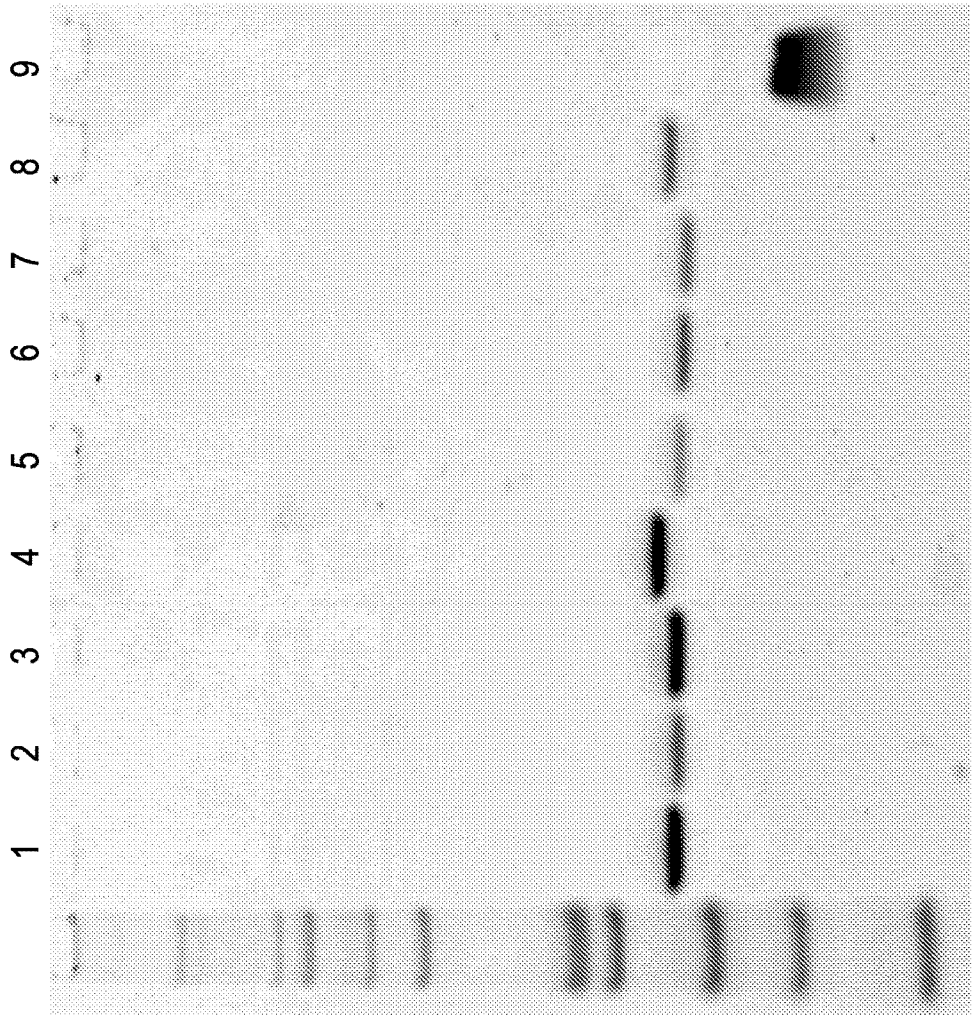
FIG. 1. Various HTPP purified V/I $^{10}$Fn3-based binders demonstrated similar expression profiles. As shown: 'GS5' (SEQ ID NO: 21) and 'GS10' (SEQ ID NO: 22).

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

The term "PK" is an acronym for "pharmokinetic" and encompasses properties of a compound including, by way of example, absorbtion, distribution, metabolism, and elimination by a subject. A "PK modulation protein" or "PK moiety" refers to any protein, peptide, or moiety that affects the pharmokinetic properties of a biologically active molecule when fused to or administered together with the biologically active molecule. Examples of a PK modulation protein or PK moiety include PEG, human serum albumin (HSA) binders (as disclosed in U.S. Publication Nos. 20050287153 and 20070003549), human serum albumin, Fc or Fc fragments, and sugars (e.g., sialic acid).

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

Targets may also be fragments of said targets. Thus a target is also a fragment of said target, capable of eliciting an immune response. A target is also a fragment of said target, capable of binding to a single domain antibody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 11, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$ M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The half-life of an amino acid sequence or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to the primate a suitable dose of the amino acid sequence or compound to be treated; collecting blood samples or other samples from said primate at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is for example made to to the standard handbooks, such as Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd Rev. edition (1982).

Half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. An "increase in half-life" in particular refers to an increase in the t½-beta, either with or without an increase in the t½-alpha and/or the AUC or both.

As used herein, the term "multivalent" refers to a recombinant molecule that incorporates two or more biologically active segments. The protein fragments forming the multivalent molecule optionally may be linked through a polypeptide linker which attaches the constituent parts and permits each to function independently.

Overview

The application provides multivalent polypeptides comprising two or more fibronectin based scaffold proteins, such as Fn3 domains. The Fn3 domains may bind to the same target, thereby increasing the valency and thus the avidity of target binding, or to different targets, thereby demonstrating multiple effector functions.

U.S. Pat. No. 6,818,418 describes fibronectin scaffold multimers that may be linked covalently or non-covalently. The present application describes improved multimers that are covalently bonded via polypeptide linkers, allowing a multivalent polypeptide to be expressed as a single construct. The application relates, in part, on the surprising discovery that Fn3 domains joined via a polypeptide linker correctly fold independently of each other, retain high affinity binding, and that each of the domains retains its functional properties.

Fibronectin Based Scaffolds

One aspect of the application provides for polypeptides comprising at least two Fn3 domains, each binding a target molecule, linked via a polypeptide. Each Fn3 domain comprises an AB loop, a BC loop, a CD loop, a DE loop, an EF loop, and an FG loop.

In some embodiments, the Fn3 domain is an Fn3 domain derived from human fibronectin, particularly the tenth Fn3 domain of fibronectin ($^{10}$Fn3), as shown in SEQ ID NO: 1. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO02/04523). A variety of additional alterations in the $^{10}$Fn3 scaffold that are either beneficial or neutral have been disclosed. See, for example, Batori et al., Protein Eng. 2002 December; 15(12):1015-20; Koide et al., Biochemistry 2001 Aug. 28; 40(34):10326-33.

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87 (Xu et al., Chemistry & Biology 2002 9:933-942). The BC, DE and FG loops align along one face of the molecule and the AB, CD and EF loops align along the opposite face of the molecule. In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation strand A, loop AB, strand B, etc. Residues involved in forming the hydrophobic core (the "core amino acid residues") include the amino acids corresponding to the following amino acids of SEQ ID NO: 1: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 1. See e.g., Dickinson et al., J. Mol. Biol. 236: 1079-1092 (1994).

In some embodiments, the $^{10}$Fn3 polypeptide may be at least 40%, 50%, 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions.

In some embodiments, the disclosure provides polypeptides comprising a tenth fibronectin type III ($^{10}$Fn3) domain, wherein the $^{10}$Fn3 domain comprises a loop, AB; a loop, BC; a loop, CD; a loop, DE; a loop, EF; and a loop, FG; and has at least one loop selected from loop BC, DE, and FG with an altered amino acid sequence relative to the sequence of the corresponding loop of the human $^{10}$Fn3 domain. In some embodiments, the BC and FG loops are altered. In some embodiments, the BC, DE, and FG loops are altered, i.e., the Fn3 domains comprise non-naturally occurring loops. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding.

In some embodiments, the polypeptide comprises a first Fn3 domain that comprises an amino acid sequence at least 80, 85, 90, 95, 98, or 100% identical to the non-loop regions of SEQ ID NO: 1, wherein at least one loop selected from BC, DE, and FG is altered. In some embodiments, the polypeptide comprises a second Fn3 domain that comprises an amino acid sequence at least 80, 85, 90, 95, 98, or 100% identical to the non-loop regions of SEQ ID NO: 1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions or a combination thereof. In some embodiments, the FG loop has up to 12 amino acid substitutions, up to 11 amino acid deletions, up to 25 amino acid insertions or a combination thereof.

The $^{10}$Fn3 domains generally begin with amino acid number 1 of SEQ ID NO: 1. However, domains with amino acid deletions are also encompassed by the invention. In some embodiments, the first eight amino acids of SEQ ID NO: 1 are deleted. Additional sequences may also be added to the N- or C-terminus. For example, an additional MG sequence may be placed at the N-terminus of an Fn3 domain, in particular at the N-terminus of the first Fn3 domain. The M will usually be cleaved off, leaving a G at the N-terminus. In some embodiments, sequences may be placed at the C-terminus of the $^{10}$Fn3 domain, e.g., SEQ ID NOS: 17, 18, or 19. In other embodiments, sequences placed at the C-terminus may be a C-terminally truncated fragment of SEQ ID NOs: 17, 18 or 19, including, for example, one of the following amino acid sequences (represented by the single letter amino acid code): E, EI, EID, EIDKP (SEQ ID NO: 50), EIDKPS (SEQ ID NO: 51), or EIDKPC (SEQ ID NO: 52).

In some embodiments, the polypeptide comprises a first and/or second $^{10}$Fn3 domain with a BC loop having the amino acid sequence of SEQ ID NO: 2, a DE loop having the amino acid sequence of SEQ ID NO: 3, and an FG loop having the amino acid sequence of SEQ ID NO: 4, wherein the Fn3 domain binds IGF-IR. In some embodiments, the polypeptide comprises a first and/or second $^{10}$Fn3 domain with a BC loop having the amino acid sequence of SEQ ID NO: 5, a DE loop having the amino acid sequence of SEQ ID NO: 6, and an FG loop having the amino acid sequence of SEQ ID NO: 7, wherein the Fn3 domain binds VEGFR2. In some embodiments, the polypeptide comprises the amino acid sequence of any one of SEQ ID NOS: 8-15, 29-31 and 63-70. In some embodiments, the polypeptide comprises the amino acid sequence at least 70, 75, 80, 85, 90, 95, or 100% identical to of any one of SEQ ID NOS: 8-15, 29-31 and 63-70.

Fibronectin naturally binds certain types of integrins through its integrin-binding motif, "arginine-glycine-aspartic acid" (RGD). In some embodiments, the polypeptide comprises a $^{10}$Fn3 domain that lacks the (RGD) integrin binding motif.

In one embodiment, a multivalent polypeptide comprises a polypeptide having the structure A-B-C, wherein A is a polypeptide comprising, consisting essentially of, or consisting of a $^{10}$Fn3 domain that binds to VEGFR2, B is a polypeptide linker, and C is a polypeptide comprising, consisting essentially of, or consisting of a $^{10}$Fn3 domain that binds to IGF-IR. In another embodiment, a multivalent polypeptide comprises a polypeptide having the structure A-B-C, wherein A is a polypeptide comprising, consisting essentially of, or consisting of a $^{10}$Fn3 domain that binds to IGF-IR, B is a polypeptide linker, and C is a polypeptide comprising, consisting essentially of, or consisting of a $^{10}$Fn3 domain that binds to VEGFR2. Specific examples of multivalent polypeptides having the structure A-B-C are polypeptides comprising (i) a polypeptide having an amino acid sequence set forth in any one of SEQ ID NOs: 8-15, 29-31 and 63-70, or (ii) a polypeptide comprising an amino acid sequence at least 85%, 90%, 95%, 97%, 98%, or 99% identical to any one of the amino acid sequences set forth in SEQ ID NOs: 8-15, 29-31 and 63-70.

In certain embodiments, the A or C region is a polypeptide comprising a $^{10}$Fn3 domain that binds to VEGFR2, wherein the $^{10}$Fn3 domain has the structure from N-terminus to C-terminus: beta strand A, loop AB, beta strand B, loop BC, beta strand C, loop CD, beta strand D, loop DE, beta strand E, loop EF, beta strand F, loop FG, beta strand G, wherein the BC loop has the amino acid sequence of SEQ ID NO: 5, the DE loop has the amino acid sequence of SEQ ID NO: 6, and the FG loop has the amino acid sequence of SEQ ID NO: 7, wherein the $^{10}$Fn3 domain folds into an antibody heavy chain variable region-like structure, and wherein the polypeptide binds to VEGFR2 with a $K_D$ of less than 100 nM. The $^{10}$Fn3 domain that binds to VEGFR2 preferably folds into a structure wherein the 7 beta strands are distributed between two beta sheets that pack against each other forming a stable core and wherein the beta strands are connected by the six loops which are solvent exposed. In exemplary embodiments, the $^{10}$Fn3 domain is from 80-150 amino acids in length.

In certain embodiments, the A or C region is a $^{10}$Fn3 domain that binds to VEGFR2 comprising a BC loop having the amino acid sequence of SEQ ID NO: 5, a DE loop having the amino acid sequence of SEQ ID NO: 6, and an FG loop having the amino acid sequence of SEQ ID NO: 7, wherein the $^{10}$Fn3 domain binds to VEGFR2 with a $K_D$ of less than 100 nM. An exemplary VEGFR2 binder is represented by the sequence:

(SEQ ID NO: 47)
EVVAATX$_{n1}$SLLIX$_{a1}$SWRHPHFPTRX$_{a2}$YYRITGEX$_{n2}$QEFTVX$_{a3}$

PLQPPTX$_{a4}$ATIX$_{n3}$DYTITVYAVX$_{a5}$TDGRNGRLLSIPX$_{a6}$
ISINYRT.

In SEQ ID NO: 47, the BC, DE and FG loops have a fixed sequence as shown in bold, the AB loop is represented by X$_{n1}$, the CD is represented by X$_{n2}$, and EF loop is represented by X$_{n3}$, and the beta strands A-G are underlined. X represents any amino acid and the subscript following the X represents an integer of the number of amino acids. In particular, n1 may be anywhere from 1-15, 2-15, 1-10, 2-10, 1-8, 2-8, 1-5, 2-5, 1-4, 2-4, 1-3, 2-3, or 1-2 amino acids; n2 and n3 may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids; and a1-a6 may each independently comprise from 0-10, 0-5, 1-10, 1-5, or 2-5 amino acids. In preferred embodiments, n1 is 2 amino acids, n2 is 7 amino acids, n3 is 7 amino acids, and a1-a6 is 0 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In certain embodiments, the VEGFR2 binder is represented by the following amino acid sequence:

```
                                              (SEQ ID NO: 40)
EVVAATPTSLLISWRHPHFPTRYYRITYGETGGNSPVQEFTV

PLQPPTATISGLKPGVDYTITVYAVTDGRNGRLLSIPISINYRT.
```

In SEQ ID NO: 40, the sequence of the BC, DE and FG loops have a fixed sequence as shown in bold (e.g., a BC loop having the amino acid sequence of SEQ ID NO: 5, a DE loop having the amino acid sequence of SEQ ID NO: 6, and an FG loop having the amino acid sequence of SEQ ID NO: 7) and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 35. In certain embodiments, the core amino acid residues are fixed and any substitutions, conservative substitutions, deletions or additions occur at residues other than the core amino acid residues. The $^{10}$Fn3 domain that binds to VEGFR2 may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSD-VPRDL (SEQ ID NO: 45), VSDVPRDL (SEQ ID NO: 46), and GVSDVPRDL (SEQ ID NO: 48), or N-terminal truncations of any one of SEQ ID NOs: 45, 46 or 48. Other suitable N-terminal extensions include, for example, $X_n$S-DVPRDL (SEQ ID NO: 53), $X_n$DVPRDL (SEQ ID NO: 54), $X_n$VPRDL (SEQ ID NO: 55), $X_n$PRDL (SEQ ID NO: 56), $X_n$RDL (SEQ ID NO: 57), $X_n$DL (SEQ ID NO: 58), or $X_n$L, wherein n=0, 1 or 2 amino acids, wherein when n=1, X is Met or Gly, and when n=2, X is Met-Gly. The $^{10}$Fn3 domain that binds to VEGFR2 may optionally comprise a C-terminal tail. Exemplary C-terminal tails include polypeptides that are from 1-20, 1-15, 1-10, 1-8, 1-5, 1-4, 1-3, 1-2, or 1 amino acids in length. Specific examples of C-terminal tails include EIDKPSQ (SEQ ID NO: 17), EIDKPCQ (SEQ ID NO: 18), and EIDK (SEQ ID NO: 19). In other embodiments, suitable C-terminal tails may be a C-terminally truncated fragment of SEQ ID NOs: 17, 18 or 19, including, for example, one of the following amino acid sequences (represented by the single letter amino acid code): E, EI, EID, EIDKP (SEQ ID NO: 50), EIDKPS (SEQ ID NO: 51), or EIDKPC (SEQ ID NO: 52). Other suitable C-terminal tails include, for example, ES, EC, EGS, EGC, EGSGS (SEQ ID NO: 71), or EGSGC (SEQ ID NO: 72). In certain embodiments, the $^{10}$Fn3 domain that binds to VEGFR2 comprises both an N-terminal extension and a C-terminal tail. In exemplary embodiments, the A region comprises an N-terminal extension beginning with Gly or Met-Gly and a C-terminal extension that does not contain a cysteine residue and the B region comprises an N-terminal extension that does not start with a Met and a C-terminal extension that comprises a cysteine residue. Specific examples of $^{10}$Fn3 domains that bind to VEGFR2 are polypeptides comprising (i) a polypeptide having an amino acid sequence set forth in any one of SEQ ID NOs: 16, 28 and 40-44, or (ii) a polypeptide comprising an amino acid sequence at least 85%, 90%, 95%, 97%, 98%, or 99% identical to the amino acid sequence set forth in any one of SEQ ID NOs: 16, 28 and 40-44.

In certain embodiments, the A or C region is a polypeptide comprising a $^{10}$Fn3 domain that binds to IGF-IR, wherein the $^{10}$Fn3 domain has the structure from N-terminus to C-terminus: beta strand A, loop AB, beta strand B, loop BC, beta strand C, loop CD, beta strand D, loop DE, beta strand E, loop EF, beta strand F, loop FG, beta strand G, wherein the BC loop has the amino acid sequence of SEQ ID NO: 2, the DE loop has the amino acid sequence of SEQ ID NO: 3, and the FG loop has the amino acid sequence of SEQ ID NO: 4, wherein the $^{10}$Fn3 domain folds into an antibody heavy chain variable region-like structure, and wherein the polypeptide binds to IGF-IR with a $K_D$ of less than 100 nM. The $^{10}$Fn3 domain that binds to IGF-IR preferably folds into a structure wherein the 7 beta strands are distributed between two beta sheets that pack against each other forming a stable core and wherein the beta strands are connected by the six loops which are solvent exposed. In exemplary embodiments, the $^{10}$Fn3 domain is from 80-150 amino acids in length.

In certain embodiments, the A or C region is a $^{10}$Fn3 domain that binds to IGF-IR comprising a BC loop having the amino acid sequence of SEQ ID NO: 2, a DE loop having the amino acid sequence of SEQ ID NO: 3, and an FG loop having the amino acid sequence of SEQ ID NO: 4, wherein the $^{10}$Fn3 domain binds to IGF-IR with a $K_D$ of less than 100 nM. An exemplary IGF-IR binder is represented by the sequence:

```
                                              (SEQ ID NO: 49)
EVVAATX$_{n1}$SLLIX$_{a1}$SWSARLKVARX$_{a2}$YYRITGEX$_{n2}$QEFTVX$_{a3}$

PKNVYTX$_{a4}$ATIX$_{n3}$DYTITVYAVX$_{a5}$TRFRDYQPX$_{a6}$ISINYRT.
```

In SEQ ID NO: 49, the BC, DE and FG loops have a fixed sequence as shown in bold, the AB loop is represented by $X_{n1}$, the CD loop is represented by $X_{n2}$, and the EF loop is represented by $X_{n3}$, and the beta strands A-G are underlined. X represents any amino acid and the subscript following the X represents an integer of the number of amino acids. In particular, n1 may be anywhere from 1-15, 2-15, 1-10, 2-10, 1-8, 2-8, 1-5, 2-5, 1-4, 2-4, 1-3, 2-3, or 1-2 amino acids; n2 and n3 may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids; and a1-a6 may each independently comprise from 0-10, 0-5, 1-10, 1-5, or 2-5 amino acids. In preferred embodiments, n1 is 2 amino acids, n2 is 7 amino acids, n3 is 7 amino acids, and a1-a6 is 0 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In certain embodiments, the IGF-IR binder is represented by the following amino acid sequence:

```
                                              (SEQ ID NO: 40)
EVVAATPTSLLISWSARLKVARYYRITGETGGNSPVQEFTV

PKNVYTATISGLKPGVDYTITVYAVTRFRDYQPISINYRT.
```

In SEQ ID NO: 40, the sequence of the BC, DE and FG loops have a fixed sequence as shown in bold (e.g., a BC loop having the amino acid sequence of SEQ ID NO: 2, a DE loop having the amino acid sequence of SEQ ID NO: 3, and an FG loop having the amino acid sequence of SEQ ID NO: 4) and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 40. In certain embodiments, the core amino acid residues are fixed and any substitutions, conservative substitutions, deletions or additions occur at residues other than the core amino acid residues. The $^{10}$Fn3 domain that binds to IGF-IR may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSD-VPRDL (SEQ ID NO: 45), VSDVPRDL (SEQ ID NO: 46), and GVSDVPRDL (SEQ ID NO: 48), or N-terminally truncated fragments of any one of SEQ ID NOs: 45, 46 or 48. Other suitable N-terminal extensions include, for example, $X_n$SDVPRDL (SEQ ID NO: 53), $X_n$DVPRDL (SEQ ID NO: 54), $X_n$VPRDL (SEQ ID NO: 55), $X_n$PRDL (SEQ ID NO: 56), $X_n$RDL (SEQ ID NO: 57), $X_n$DL (SEQ ID NO: 58), or $X_n$L, wherein n=0, 1 or 2 amino acids, wherein when n=1, X is Met or Gly, and when n=2, X is Met-Gly. The $^{10}$Fn3 domain that binds to IGF-IR may optionally comprise a C-terminal tail. Exemplary C-terminal tails include polypeptides that are from 1-20, 1-15, 1-10, 1-8, 1-5, 1-4, 1-3, 1-2, or 1 amino acids in length. Specific examples of C-terminal tails include EIDKPSQ (SEQ ID NO: 17), EIDKPCQ (SEQ ID NO: 18), and EIDK (SEQ ID NO: 19). In other embodiments, suitable C-terminal tails may be a C-terminally truncated fragment of SEQ ID NOs: 17, 18 or 19, including, for example, one of the following amino acid sequences (represented by the single letter amino acid code): E, EI, EID, EIDKP (SEQ ID NO: 50), EIDKPS (SEQ ID NO: 51), or EIDKPC (SEQ ID NO: 52). Other suitable C-terminal tails include, for example, ES, EC, EGS, EGC, EGSGS (SEQ ID NO: 71), or EGSGC (SEQ ID NO: 72). In certain embodiments, the $^{10}$Fn3 domain that binds to IGF-IR comprises both an N-terminal extension and a C-terminal tail. In exemplary embodiments, the A region comprises an N-terminal extension beginning with Gly or Met-Gly and a C-terminal extension that does not contain a cysteine residue and the B region comprises an N-terminal extension that does not start with a Met and a C-terminal extension that comprises a cysteine residue. Specific examples of $^{10}$Fn3 domains that bind to IGF-IR are polypeptides comprising (i) a polypeptide having the amino acid sequence set forth in any one of SEQ ID NOs: 26-27 and 35-39, or (ii) a polypeptide comprising an amino acid sequence at least 85%, 90%, 95%, 97%, 98%, or 99% identical to the amino acid sequence set forth in any one of SEQ ID NOs: 26-27 and 35-39.

The B region is a polypeptide linker. Exemplary polypeptide linkers include polypeptides having from 1-20, 1-15, 1-10, 1-8, 1-5, 1-4, 1-3, or 1-2 amino acids. Specific examples of suitable polypeptide linkers are described further herein. In certain embodiments, the linker may be a C-terminal tail polypeptide as described herein, an N-terminal extension polypeptide as described herein, or a combination thereof.

In one embodiment, a multivalent polypeptide comprises a polypeptide having the structure $X_1$-A-$X_2$-B-$X_3$-C-$X_4$, wherein $X_1$ is an optional N-terminal extension, A is a $^{10}$Fn3 domain that binds to VEGFR2, $X_2$ is an optional C-terminal tail, B is a polypeptide linker, $X_3$ is an optional N-terminal extension, C is a $^{10}$Fn3 domain that binds to IGF-IR, and $X_4$ is an optional C-terminal tail. In another embodiment, a multivalent polypeptide comprises a polypeptide having the structure $X_1$-A-$X_2$-B-$X_3$-C-$X_4$, wherein $X_1$ is an optional N-terminal extension, A is a $^{10}$Fn3 domain that binds to IGF-IR, $X_2$ is an optional C-terminal tail, B is a polypeptide linker, $X_3$ is an optional N-terminal extension, C is a $^{10}$Fn3 domain that binds to VEGFR2, and $X_4$ is an optional C-terminal tail. Specific examples of suitable N-terminal extensions and C-terminal tails are described above. In certain embodiments, one or more of $X_1$, $X_2$, B, $X_3$ or $X_4$ may comprise an amino acid residue suitable for pegylation, such as a cysteine or lysine residue. In exemplary embodiments, $X_4$ comprises at least one amino acid suitable for pegylation, such as a cysteine or lysine residue. Specific examples of suitable polypeptide linkers are described further below. Specific examples of multivalent polypeptides having the structure $X_1$-A-$X_2$-B-$X_3$-C-$X_4$ are polypeptides comprising (i) a polypeptide having the amino acid sequence set forth in any one of SEQ ID NOs: 8-15, 29-31 and 63-70, or (ii) a polypeptide comprising an amino acid sequence at least 85%, 90%, 95%, 97%, 98%, or 99% identical to the amino acid sequence set forth in any one of SEQ ID NOs: 8-15, 29-31 and 63-70.

In exemplary embodiments, X as defined herein is a naturally occurring amino acid.

Polypeptide Linkers

The application provides multivalent polypeptides comprising at least two Fn3 domains linked via a polypeptide linker. The polypeptides comprise an N-terminal domain comprising a first Fn3 domain and a C-terminal domain comprising a second Fn3 domain. The first and second Fn3 domains may be directly or indirectly linked via a polypeptide linker. Additional linkers or spacers, e.g., SEQ ID NOS: 17, 18, or 19, may be introduced at the C-terminus of the first Fn3 domain between the Fn3 domain and the polypeptide linker. Additional linkers or spacers may be introduced at the N-terminus of the second Fn3 domain between the Fn3 domain and the polypeptide linker.

Suitable linkers for joining the Fn3 domains are those which allow the separate domains to fold independently of each other forming a three dimensional structure that permits high affinity binding to a target molecule. The application provides that suitable linkers that meet these requirements comprise glycine-serine based linkers, glycine-proline based linkers, proline-alanine based linkers as well as the linker SEQ ID NO: 20. The Examples described herein demonstrate that Fn3 domains joined via these linkers retain their target binding function. In some embodiments, the linker is a glycine-serine based linker. These linkers comprise glycine and serine residues and may be between 8 and 50, 10 and 30, and 10 and 20 amino acids in length. Examples of such linkers include SEQ ID NOS: 23, 24, and 25. In some embodiments the polypeptide linker is selected from SEQ ID NOS: 21 and 22. In some embodiments, the linker is a glycine-proline based linker. These linkers comprise glycine and proline residues and may be between 3 and 30, 10 and 30, and 3 and 20 amino acids in length. Examples of such linkers include SEQ ID NOS: 32, 33, and 34. In some embodiments, the linker is a proline-alanine based linker. These linkers comprise proline and alanine residues and may be between 3 and 30, 10 and 30, 3 and 20 and 6 and 18 amino acids in length. Examples of such linkers include SEQ ID NOS: 60, 61 and 62. It is contemplated, that the optimal linker length and amino acid composition may be determined by routine experimentation by methods well known in the art. In some embodiments, the polypeptide linker is SEQ ID NO: 20.

Pharmacokinetic Moieties

In one aspect, the application provides for multivalent polypeptides further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The polypeptides may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety.

Moieties that tend to slow clearance of a protein from the blood, herein referred to as "PK moieties", include polyoxyalkylene moieties, e.g., polyethylene glycol, sugars (e.g., sialic acid), and well-tolerated protein moieties (e.g., Fc, Fc fragments, transferrin, or serum albumin). The polypeptides may be fused to albumin or a fragment (portion) or variant of albumin as described in U.S. Publication No. 20070048282.

In some embodiments, the PK moiety is a serum albumin binding protein such as those described in U.S. Publication Nos. 2007/0178082 and 2007/0269422.

In some embodiments, the PK moiety is a serum immunoglobulin binding protein such as those described in U.S. Publication No. 2007/0178082.

In some embodiments, the multivalent polypeptide comprises polyethylene glycol (PEG). One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

Pegylation may be achieved by site-directed pegylation, wherein a suitable reactive group is introduced into the protein to create a site where pegylation preferentially occurs. In some embodiments, the protein is modified to introduce a cysteine residue at a desired position, permitting site directed pegylation on the cysteine. In some embodiments, the polypeptide comprises a Cys containing linker such as SEQ ID NO: 18, which permits site directed pegylation. In some embodiments, the Cys containing linker is introduced at the 3' end of the second Fn3 domain (i.e., the domain most C-terminal in the polypeptide). PEG may vary widely in molecular weight and may be branched or linear.

In some embodiments, the multivalent polypeptide comprises an Fn3 domain and a PK moiety. In some embodiments, the Fn3 domain is a $^{10}$Fn3 domain. In some embodiments, the PK moiety increases the serum half-life of the polypeptide by more than 5, 10, 20, 30, 40, 50, 60, 70, 80, 90, 100, 120, 150, 200, 400, 600, 800, 1000% or more relative to the Fn3 domain alone.

In some embodiments, the PK moiety is linked to the Fn3 domain via at least one disulfide bond, a peptide bond, a polypeptide, a polymeric sugar, or a polyethylene glycol moiety. Exemplary polypeptide linkers include PSTSTST (SEQ ID NO: 20), EIDKPSQ (SEQ ID NO: 17), and GS linkers, such as GSGSGSGSGS (SEQ ID NO: 21) and multimers thereof. In some embodiments the PK moiety is human serum albumin. In some embodiments, the PK moiety is transferrin.

Target

The application provides multivalent polypeptides comprising a first Fn3 domain that binds to a first target molecule and a second Fn3 domain that binds to a second target molecule. The first and second target molecules may be the same or different target molecules. When the first and second target molecules are the same, the Fn3 domains, i.e., the binding loops, may be the same or different. Therefore, the first and second Fn3 domains may bind to the same target but at different epitopes. By introducing sequence variation in the loop regions, in particular loops BC, DE, and FG, Fn3 domains can be generated that can bind to almost any target molecule.

Polypeptide binding to a target molecule may be assessed in terms of equilibrium constants (e.g., dissociation, $K_D$) and in terms of kinetic constants (e.g., on rate constant, $k_{on}$ and off rate constant, $k_{off}$). An Fn3 domain will generally bind to a target molecule with a $K_D$ of less than 500 nM, 100 nM, 1 nM, 500 pM, 100 pM or less, although higher $K_D$ values may be tolerated where the $k_{off}$ is sufficiently low or the $k_{on}$ is sufficiently high.

In some embodiments, the first and/or second Fn3 domain binds a target selected from IGF-IR, FGFR, FGFR1, FGFR2, FGFR3, FGFR4, FGFR5, c-Kit, human p185 receptor-like tyrosine kinase, EGFR, HER2, HER3, HER4, c-Met, folate receptor, PDGFR, VEGFR1, VEGFR2, VEGFR3, human vascular endothelial growth factor (VEGF)-A, VEGF-C, VEGF-D, human CD20, human CD18, human CD11a, human apoptosis receptor-2 (Apo-2), human alpha4beta7 integrin, human GPIIb-IIIa integrin, stem cell factor (SCF), human CD3, IGF-IR, Ang1, Ang2, fibroblast growth factor, epidermal growth factor, hepatocyte growth factor, or Tie2.3. In some embodiments, the first Fn3 domain is in the N-terminal position and binds IGF-IR and the second Fn3 domain binds VEGFR2. In some embodiments, the first Fn3 domain is in the N-terminal position and binds VEGFR2 and the second domain binds IGF-IR. In some embodiments, the first Fn3 domain is in the N-terminal position and binds IGF-1R and the second domain binds VEGFR2.

In certain embodiments, the multivalent polypeptides comprise first and second Fn3 domains that bind to different targets. In such embodiments, it may be desirable to tune the potency of one Fn3 binding domain relative to the other Fn3 binding domain. For example, if the binding affinity of the first Fn3 domain is significantly higher than the binding affinity of the second Fn3 domain, the biological effect of the first Fn3 domain could overwhelm the effects of the second of second Fn3 domain. Accordingly, in certain embodiments, it may be desirable for the binding affinities of the first and second Fn3 domains of a multivalent polypeptide to be similar to each other, e.g., binding affinities within 100-fold, 30-fold, 10-fold, 3-fold, 1-fold, 0.3-fold or 0.1-fold, of each other, or binding affinities within 0.1-fold to 10-fold, within 0.3-fold to 10-fold, within 0.1-fold to 3-fold, within 0.3-fold to 3-fold, within 0.1-fold to 1-fold, within 0.3-fold to 1-fold, within 1-fold to 10-fold, within 3-fold to 10-fold, within 3-fold to 30-fold, or within 1-fold to 3-fold of each other.

Multi-Domain Embodiments

One aspect of the application provides for multivalent polypeptides further comprising a binding moiety. In some embodiments, the binding moiety binds a human target protein with a $K_D$ of less than $10^{-6}$M, $10^{-7}$M, $10^{-8}$M, $10^{-9}$M, or $10^{-9}$M.

In some embodiments, the binding moiety binds a tumor associated target or antigen. In some embodiments antigen targeting will help localize the multivalent polypeptide in terms of tissue distribution or increased local concentration affect either in the tissue or desired cell type.

In some embodiments, the binding moiety binds a tumor associated target or antigen, such as, for example, carbonic anhydrase IX, A3, antigen specific for A33 antibody, BrE3-antigen, CD1, CD1a, CD3, CDS, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RSS, 5100, TAG-72, p53, tenascin, IL-6, IL-8, insulin growth factor-I (IGF-I), insulin growth factor-II (IGF-II), Tn antigen, Thomson-Friedenreich antigens, tumor necrosis antigens, placenta growth factor (PlGF), 17-1A-antigen, an angiogenesis marker (e.g., ED-B fibronectin), an oncogene marker, an oncogene product, and other tumor-associated antigens. Recent reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference.

In some embodiments, the binding moiety is selected from an antibody moiety. An antibody moiety refers to immunoglobulin molecules and immunologically active portions of immunoglobulin molecules, i.e., molecules that contain an antigen binding site that immunospecifically binds an antigen. As such, the term antibody moiety encompasses not only whole antibody molecules, but also antibody multimers and antibody fragments as well as variants (including derivatives) of antibodies, antibody multimers and antibody fragments. Examples of antibody moieties include, but are not limited to single chain Fvs (scFvs), Fab fragments, Fab' fragments, F(ab')$_2$, disulfide linked Fvs (sdFvs), and Fvs. Antibody moieties may be, for example, monoclonal, chimeric, human, or humanized.

In some embodiments, the antibody moiety is selected from (i) a Fab fragment, having VL, CL, VH and CH1 domains; (ii) a Fab' fragment, which is a Fab fragment having one or more cysteine residues at the C-terminus of the CH1 domain; (iii) a Fd fragment having VH and CH1 domains; (iv) a Fd' fragment having VH and CH1 domains and one or more cysteine residues at the C-terminus of the CH1 domain; (v) a Fv fragment having the VL and VH domains of a single arm of an antibody; (vi) a dAb fragment (Ward et al., Nature 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) a "diabody" with two antigen binding sites, comprising a heavy chain variable domain (VH) connected to a light chain variable domain (VL) in the same polypeptide chain (see, e.g., EP Patent Publication No. 404,097; WO93/11161; and Hollinger et al., Proc. Natl. Acad. Sci. USA, 90:6444-6448 (1993)); and (xi) a "linear antibody" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

In some embodiments, an antibody moiety is a single domain antibody. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, bovine.

In some embodiments, a single domain antibody is a naturally occurring single domain antibody such as VHH domains. VHHs are heavy chain variable domains derived from immunoglobulins naturally devoid of light chains such as those derived from Camelidae (including camel, dromedary, llama, vicuna, alpaca and guanaco) as described in WO94/04678. VHH molecules are about 10 times smaller than IgG molecules. Since VHH's are known to bind to 'unusual' epitopes such as cavities or grooves, the affinity of such VHH's may be more suitable for therapeutic treatment, PCT Publication No. WO97/49805.

In some embodiments, the single domain antibody is a VHH that binds a serum protein as described in U.S. Publication No. 20070178082. The serum protein may be any suitable protein found in the serum of subject, or fragment thereof. In some embodiments, the serum protein is serum albumin, serum immunoglobulins, thyroxine-binding protein, transferrin, or fibrinogen.

Various techniques have been developed for the production of antibody fragments that may be used to make antibody fragments used in the invention. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

In some embodiments, the binding moiety comprises one or more avimer sequences. Avimers were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains that may exhibit improved affinity (in some cases sub-nanomolar) and specificity compared with single-epitope binding proteins. Additional details concerning methods of construction and use of avimers are disclosed, for example, in U.S. Patent Publication Nos. 20040175756, 20050048512, 20050053973, 20050089932 and 20050221384, which is incorporated herein by reference in their entirety.

In some embodiments, the binding moiety comprises one or more lipocalin related sequences, e.g., anticalins or lipocalin derivatives. Anticalins or lipocalin derivatives are a type of binding proteins that have affinities and specificities for various target molecules, including those described herein. Such proteins are described in US Patent Publication Nos. 20060058510, 20060088908, 20050106660, and PCT Publication No. WO2006/056464.

In some embodiments, the binding moiety comprises one or more tetranectin C-type lectin related sequences or trinectins, e.g., tetranectin C-type lectin or tetranectin C-type lectin derivatives. Tetranectin C-type lectins or tetranectin C-type lectin derivatives are a type of binding proteins that have affinities and specificities for various target molecules including those described herein. Different tetranectin C-type lectin and related proteins are described in PCT Publication Nos. WO2006/053568, WO2005/080418, WO2004/094478, WO2004/039841, WO2004/005335, WO2002/048189, WO98/056906, and U.S. Patent Publication No. 20050202043.

In some embodiments, the binding moiety comprises one or more natural ankyrin repeat proteins, e.g., DARPins (Molecular Partners).

In some embodiments, the binding moiety comprises one or more Affibodies™. Affibodies™ are derived from the IgG binding domain of Staphyloccal Protein A. Novel binding properties can be achieved by altering residues located near the binding surface of the Protein A domain.

In some embodiments, the binding moiety comprises one or more cysteine knot based protein scaffolds, i.e., microbodies (Selecore/NascaCell).

In some embodiments, the binding moiety comprises one or more Trans-bodies™. Trans-bodies™ are based on transferrin scaffolds (BioResis/Pfizer).

In some embodiments, the binding moiety comprises binding proteins based on gamma-crystalline or ubiquitin. These so-called Affilin™ (Scil Proteins) molecules are characterized by the de novo design of a binding region in beta sheet structures of the proteins. Affilin™ molecules have been described in U.S. Publication No. 20070248536.

Conjugation

The multivalent polypeptide and the binding moiety may be linked via at least one disulfide bond, a peptide bond, a polypeptide, a polymeric sugar, or a PEG moiety.

In some embodiments, the multivalent polypeptide and the binding moiety are linked via a polypeptide. In some embodiments, the polypeptide linker is SEQ ID NOS: 17, 18, or 20.

In some embodiments, the multivalent polypeptide and the binding moiety are linked via a polypeptide linker having a protease site that is cleavable by a protease in the blood or target tissue. Such embodiments can be used to release two or more therapeutic proteins for better delivery or therapeutic properties or more efficient production compared to separately producing such proteins.

In some embodiments, the multivalent polypeptide and the binding moiety are linked via a biocompatible polymer such as a polymeric sugar. Such polymeric sugar can include an enzymatic cleavage site that is cleavable by an enzyme in the blood or target tissue. Such embodiments can be used to release two or more therapeutic proteins for better delivery or therapeutic properties or more efficient production compared to separately producing such proteins.

In some embodiments, the multivalent polypeptide and the binding moiety are linked via a polymeric linker. Polymeric linkers can be used to optimally vary the distance between each protein moiety to create a protein with one or more of the following characteristics: 1) reduced or increased steric hindrance of binding of one or more protein domain when binding to a protein of interest, 2) increased protein stability or solubility without searching for additional amino acid substitutions to increase stability or solubility (e.g., solubility at least about 20 mg/ml, or at least about 50 mg/ml), 3) decreased protein aggregation without searching for additional amino acid substitutions to decrease stability (e.g., as measured by SEC), and 4) increased the overall avidity or affinity of the protein by adding additional binding domains.

In some embodiments, the multivalent polypeptide comprises a second $^{10}$Fn3 domain comprising the linker of SEQ ID NO: 18. PEG is conjugated to the cysteine moiety in the linker sequence and links the multivalent polypeptide and the binding moiety.

PEGylated Embodiments

One aspect of the application provides linking the multivalent polypeptides to nonproteinaceous polymers. In some embodiments, the polymer is polyethylene glycol ("PEG"), polypropylene glycol, or polyoxyalkylenes, as described in U.S. Pat. Nos. 4,640,835; 4,496,689; 4,301,144; 4,670,417; 4,791,192 or 4,179,337. In some embodiments, the multivalent polypeptides comprise an Fn3 domain. In some embodiments, the polymer is a PEG moiety. In addition, the application provides N or C terminal PEG conjugation to antibody moieties (e.g., camel antibodies and their derivatives, as well as single chain and domain antibodies; and particularly those expressed from microbes) and antibody-like moieties (e.g., derivatives of lipocalins, ankyrins, multiple Cys-Cys domains, and tetranectins; and particularly those expressed from microbes).

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_{n-1}$CH$_2$CH$_2$OH (1), where n is 20 to 2300 and X is H or a terminal modification, e.g., a C$_{14}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, *J. Biol. Chem.*, 252, 3571 (1977) and *J. Biol. Chem.*, 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

The size of PEG utilized will depend on several factors including the intended use of the multivalent polypeptide. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging application, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to binding polypeptides of the invention. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to the multivalent polypeptide. In some embodiments, the PEG moiety is about 20, 30, 40, 50, 60, 70, 80, or 90 KDa. In some embodiments, the PEG moiety is about 40 KDa.

In some embodiments, PEGylated multivalent polypeptides contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, or from about 10,000 Da to 36,000 Da. In a one embodiment, the PEG in pegylated binding polypeptide is a substantially linear, straight-chain PEG.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In some embodiments, a multivalent polypeptide is covalently linked to one poly(ethylene glycol) group of the formula: $-CO-(CH_2)_x-(OCH_2CH_2)_m-OR$, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of a multivalent polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylated at a ε-amino group of a binding polypeptide lysine or the N-terminal amino group of the binding polypeptide.

In another embodiment, PEG molecules may be coupled to sulfhydryl groups on a binding polypeptide (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments, the pegylated a multivalent polypeptide is produced by site-directed pegylation, particularly by conjugation of PEG to a cysteine moiety at the N- or C-terminus. In some embodiments, the multivalent polypeptide is an Fn3 domain covalently bound to a PEG moiety, wherein at least one of the loops of said Fn3 domain participates in target binding. The PEG moiety may be attached to the Fn3 polypeptide by site directed pegylation, such as by attachment to a Cys residue, where the Cys residue may be positioned at the N-terminus of the Fn3 polypeptide or between the N-terminus and the most N-terminal beta or beta-like strand or at the C-terminus of the Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414 (6866):933-8) and thus the surface-exposed residues identified. In one embodiment, cysteine residues are introduced into binding polypeptides at or near the N- and/or C-terminus, or within loop regions. Pegylation of cysteine residues may be carried out using, for example, PEG-maleiminde, PEG-vinylsulfone, PEG-iodoacetamide, or PEG-orthopyridyl disulfide.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Publication No. 2002/0044921 and PCT Publication No. WO94/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

Conventional separation and purification techniques known in the art can be used to purify PEGylated binding polypeptide, such as size exclusion (e.g., gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment of the invention, the PEG in a pegylated multivalent polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated polypeptides will preferably retain at least about 25%, 50%, 60%, 70%, 80%, 85%, 90%, 95% or 100% of the biological activity associated with the unmodified protein. In one embodiment, biological activity refers to its ability to bind to a target molecule, as assessed by $K_D$, $k_{on}$ or $k_{off}$. In one specific embodiment, the pegylated binding polypeptide protein shows an increase in binding to a target molecule relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Deimmunization of Multivalent Polypeptides

In one aspect, the application provides deimmunized multivalent polypeptides. In some embodiments, the sequence of a multivalent polypeptide has been altered to eliminate one or more B- or T-cell epitopes.

The multivalent polypeptide may be deimmunized to render it non-immunogenic, or less immunogenic, to a given species. Deimmunization can be achieved through structural alterations to the polypeptide. Any deimmunization technique known to those skilled in the art can be employed. One suitable technique, for example, for deimmunizing proteins is described in WO 00/34317, the disclosure of which is incorporated herein in its entirety. In summary, a typical protocol within the general method described therein includes the following steps:

1. Determining the amino acid sequence of the polypeptide;
2. Identifying potential T-cell epitopes within the amino acid sequence of the polypeptide by any method including determination of the binding of peptides to MHC molecules, determination of the binding of peptide: HLA complexes to the T-cell receptors from the species to receive the therapeutic protein, testing of the polypeptide or parts thereof using transgenic animals with HLA molecules of the species to receive the therapeutic protein, or testing such transgenic animals reconstituted with immune system cells from the species to receive the therapeutic protein; and
3. By genetic engineering or other methods for producing modified polypeptide, altering the polypeptide to remove one or more of the potential T-cell epitopes and producing such an altered polypeptide for testing.

In one embodiment, the sequences of the polypeptide can be analyzed for the presence of MHC class II binding motifs. For example, a comparison may be made with databases of MHC-binding motifs such as, for example by searching the "motifs" database on the worldwide web at sitewehil.we-hi.edu.au. Alternatively, MHC class II binding peptides may be identified using computational threading methods such as those devised by Altuvia et al. (J. Mol. Biol. 249 244-250

(1995)) whereby consecutive overlapping peptides from the polypeptide are testing for their binding energies to MHC class II proteins. Computational binding prediction algorithms include iTope™, Tepitope, SYFPEITHI, EpiMatrix (EpiVax), and MHCpred. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

Once identified T-cell epitopes are removed, the deimmunized sequence may be analyzed again to ensure that new T-cell epitopes have not been created and, if they have, the epitope(s) can be deleted.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining binding affinity of the polypeptide. Therefore, one strategy is to sequentially introduce substitutions into the polypeptide and then test for antigen binding and immunogenicity.

In one aspect the deimmunized polypeptide is less immunogenic (or rather, elicits a reduced HAMA response) than the original polypeptide in a human subject. Assays to determine immunogenicity are well within the knowledge of the skilled person. Art-recognized methods of determining immune response can be performed to monitor a HAMA response in a particular subject or during clinical trials. Subjects administered deimmunized polypeptide can be given an immunogenicity assessment at the beginning and throughout the administration of said therapy. The HAMA response is measured, for example, by detecting antibodies to the deimmunized polypeptide, in serum samples from the subject using a method known to one in the art, including surface plasmon resonance technology (BIACORE) and/or solid-phase ELISA analysis. Alternatively, in vitro assays designed to measure a T-cell activation event are also indicative of immunogenicity.

Additional Modifications

In some embodiments, the multivalent polypeptides are glycosylated. Fn3 domains do not normally contain glycosylation sites, however, such glycosylation may be engineered into the protein.

Glycosylation of proteins is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. These can be engineered into the proteins of the invention, in particular fibronectin-based scaffold proteins and their corresponding polynucleotides. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to proteins is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In some embodiments, the multivalent polypeptides are modified to enhance antigen-dependent cell-mediated cytotoxicity (ADCC) and/or complement dependent cytotoxicity (CDC). In some embodiments, the multivalent polypeptide is an Fn3 domain further comprising an Fc region. In some embodiments, the Fc region is a variant that enhances ADCC or CDC. The Fc region variant may comprise a human Fc region sequence (e.g., a human IgG1, IgG2, IgG3 or IgG4 Fc region) comprising an amino acid modification (e.g., a substitution) at one or more amino acid positions.

In one embodiment, the variant Fc region may mediate antibody-dependent cell-mediated cytotoxicity (ADCC) in the presence of human effector cells more effectively, or bind an Fc gamma receptor (FcγR) with better affinity, than a native sequence Fc region. Such Fc region variants may comprise an amino acid modification at any one or more of positions 256, 290, 298, 312, 326, 330, 333, 334, 360, 378 or 430 of the Fc region, wherein the numbering of the residues in the Fc region is that of the EU index as in Kabat.

Nucleic Acid-Protein Fusion Technology

In one aspect, the application provides multivalent polypeptides comprising fibronectin type III domains that bind a human target, such as, for example, EGFR, VEGFR2, IGF-IR, or other proteins. One way to rapidly make and test Fn3 domains with specific binding properties is the nucleic acid-protein fusion technology of Adnexus, a Bristol-Myers Squibb R&D Company. This disclosure describes the use of such in vitro expression and tagging technology, termed PROfusion™, that exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO00/34784; WO01/64942; WO02/032925; and Roberts and Szostak, Proc Natl. Acad. Sci. 94:12297-12302, 1997, herein incorporated by reference. Further discussion of nucleic acid-protein fusion technology can be found in the Examples and the Materials and Methods section of the application.

Vectors & Polynucleotides Embodiments

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the multivalent antibody-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, E. coli or Bacillus spp. Yeast, preferably from the Saccharomyces species, such as S. cerevisiae, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in E. coli as the preferred method for expression. The protein is then purified from culture media or cell extracts.

Suitable host cells for the expression of glycosylated proteins of the invention are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the present invention, particularly for transfection of Spodoptera frugiperda cells.

In some instance it will be desired to produce proteins in vertebrate cells, such as for glycosylation, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59. (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; a human hepatoma line (Hep G2); and myeloma or lymphoma cells (e.g., Y0, J558L, P3 and NS0 cells) (see U.S. Pat. No. 5,807,715). Plant cell cultures of cotton, corn, potato, soybean, petunia, tomato, and tobacco can also be utilized as hosts.

Protein Production

Host cells are transformed with the herein-described expression or cloning vectors for protein production and cultured in conventional nutrient media modified as appropriate for inducing promoters, selecting transformants, or amplifying the genes encoding the desired sequences. In the examples shown here, the host cells used for high-throughput protein production (HTPP) and mid-scale production was the HMS174-bacterial strain.

The host cells used to produce the proteins of this invention may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Proteins of the invention can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Imaging, Diagnostic and Other Applications

In one aspect, the application provides multivalent polypeptides labeled with a detectable moiety. The polypeptides may be used for a variety of diagnostic applications. The detectable moiety can be any one which is capable of producing, either directly or indirectly, a detectable signal. For example, the detectable moiety may be a radioisotope, such as H3, C14 or 13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a moiety (such as PEG) to a protein of the invention, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

Multivalent binding polypeptides linked with a detectable moiety also are useful for in vivo imaging. The polypeptide may be linked to a radio-opaque agent or radioisotope, administered to a subject, preferably into the bloodstream, and the presence and location of the labeled protein in the subject is assayed. This imaging technique is useful in the staging and treatment of malignancies. The protein may be labeled with any moiety that is detectable in a subject, whether by nuclear magnetic resonance, radiology, or other detection means known in the art.

Multivalent polypeptides also are useful as affinity purification agents. In this process, the polypeptides are immobilized on a suitable support, such a Sephadex resin or filter paper, using methods well known in the art.

Multivalent polypeptides can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting a target molecule in a sample. A method may comprise contacting the sample with a multivalent polypeptide described herein, wherein said contacting is carried out under conditions that allow polypeptide-target complex formation; and detecting said complex, thereby detecting said target in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, a suspected tumor. The sample may be from a human or other mammal. The multivalent polypeptide may be labeled with a labeling moiety, such as a radioactive moiety, a fluorescent moiety, a chromogenic moiety, a chemiluminescent moiety, or a hapten moiety. The multivalent polypeptide may be immobilized on a solid support.

Therapeutic/In Vivo Uses

In one aspect, the application provides multivalent polypeptides useful in the treatment of disorders. The application also provides methods for administering multivalent polypeptides to a subject. In some embodiments, the subject is a human. In some embodiments, the multivalent polypeptides are pharmaceutically acceptable to a mammal, in particular a human. A "pharmaceutically acceptable" polypeptide refers to a polypeptide that is administered to an animal without significant adverse medical consequences. Examples of pharmaceutically acceptable multivalent polypeptides include $^{10}$Fn3 domains that lack the integrin-binding domain (RGD) and $^{10}$Fn3 domains that are essentially endotoxin free or have very low endotoxin levels.

The multivalent polypeptides are particularly useful in disorders such as cancer. In an exemplary embodiment, the multivalent polypeptide comprises Fn3 domains that bind to two different targets. The two targets may be within the same signaling pathway or within two separate signaling pathways. One of the target molecules may "recruit" the multivalent polypeptide to a particular site, such as a cancer cell, while binding to the second target molecule may affect a particular signaling pathway.

One aspect of the applications provides multivalent polypeptides that target one or more proteins involved in tumor biology, such as, for example, VEGFR2, IGF-IR, and EGFR. In some embodiments, administration of a multivalent polypeptide inhibits tumor cell growth in vivo. The tumor cell may be derived from any cell type including, without limitation, epidermal, epithelial, endothelial, leukemia, sarcoma, multiple myeloma, or mesodermal cells. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/]GF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SY5Y cells, Sk-Mel-2 cells, NCI-H929, RPM18226, and A431 cells. In some embodiments, the polypeptide inhibits tumor cell growth relative to the growth of the tumor in an untreated animal. In some embodiments, the polypeptide inhibits tumor cell growth by 50, 60, 70, 80% or more relative to the growth of the tumor in an untreated animal. In some embodiments, the inhibition of tumor cell growth is measured at least 7 days or at least 14 days after the animals have started treatment with the polypeptide. In some embodiments, another antineoplastic agent is administered to the animal with the polypeptide.

In certain aspects, the disclosure provides methods for administering multivalent polypeptides for the treatment and/or prophylaxis of tumours and/or tumour metastases, where the tumour is particularly preferably selected from the group consisting of brain tumour, tumour of the urogenital tract, tumour of the lymphatic system, stomach tumour, laryngeal tumour, monocytic leukemia, lung adenocarcinoma, small-cell lung carcinoma, pancreatic cancer, glioblastoma and breast carcinoma, without being restricted thereto.

In certain aspects, the disclosure provides methods for administering multivalent polypeptide for the treatment of diseases selected from the group of cancerous diseases consisting of squamous cell carcinoma, bladder cancer, stomach cancer, liver cancer, kidney cancer, colorectal cancer, breast cancer, head cancer, neck cancer, oesophageal cancer, gynecological cancer, thyroid cancer, lymphoma, chronic leukemia and acute leukemia.

Additional Agents that May be Used with Appropriate Embodiments of the Invention One aspect of the invention provides multivalent polypeptides linked to a cytotoxic agent. Such embodiments can be prepared by in vitro or in vivo methods as appropriate. In vitro methods, include conjugation chemistry well know in the art including chemistry compatible with proteins, such as chemistry for specific amino acids, such as Cys and Lys. In order to link a cytotoxic agent to a polypeptide, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the cytotoxic agent. Preferred cytotoxic agents are maytansinoids, taxanes and analogs of CC-1065.

In some embodiments, a multivalent polypeptide is linked to a bacterial toxin, a plant toxin, ricin, abrin, a ribonuclease (RNase), DNase I, a protease, Staphylococcal enterotoxin-A, pokeweed antiviral protein, gelonin, diphtherin toxin, *Pseudomonas* exotoxin, *Pseudomonas* endotoxin, Ranpimase (Rap), Rap (N69Q), an enzyme, or a fluorescent protein.

In some embodiments, a multivalent polypeptide is linked to maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

In some embodiments, a multivalent polypeptide is linked to a taxanes. Taxanes suitable for use in the present invention are disclosed in U.S. Pat. Nos. 6,372,738 and 6,340,701.

In some embodiments, a multivalent is linked to CC-1065 or its analogs. CC-1065 and its analogs are disclosed in U.S. Pat. Nos. 6,372,738; 6,340,701; 5,846,545 and 5,585,499.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., Cancer Res., 42, 3532-3537 (1982)).

Cytotoxic drugs such as methotrexate, daunorubicin, doxorubicin, vincristine, vinblastine, melphalan, mitomycin C, chlorambucil, and calicheamicin are also suitable for the preparation of conjugates of the present invention, and the drug molecules can also be linked to multivalent polypeptides through an intermediary carrier molecule such as serum albumin.

In other therapeutic treatments or compositions, multivalent polypeptides are co-administered, or administered sequentially, with one or more additional therapeutic agents. Suitable therapeutic agents include, but are not limited to, targeted therapeutics, other targeted biologics, and cytotoxic or cytostatic agents. In some instances in will be preferred to administer agents from the same or separate therapeutically acceptable vial, syringe or other administration device that holds a liquid formulation.

Cancer therapeutic agents are those agents that seek to kill or limit the growth of cancer cells while having minimal effects on the patient. Thus, such agents may exploit any difference in cancer cell properties (e.g., metabolism, vascularization or cell-surface antigen presentation) from healthy host cells. Differences in tumor morphology are potential sites for intervention: for example, the second therapeutic can be an antibody such as an anti-VEGF antibody that is useful in retarding the vascularization of the interior of a solid tumor, thereby slowing its growth rate. Other therapeutic agents include, but are not limited to, adjuncts such as granisetron HCl, androgen inhibitors such as leuprolide acetate, antibiotics such as doxorubicin, antiestrogens such as tamoxifen, antimetabolites such as interferon alpha-2a, cytotoxic agents such as taxol, enzyme inhibitors such as ras farnesyl-transferase inhibitor, immunomodulators such as aldesleukin, and nitrogen mustard derivatives such as melphalan HCl, and the like.

The therapeutic agents that can be combined with multivalent polypeptides for improved anti-cancer efficacy include diverse agents used in oncology practice (Reference: Cancer, Principles & Practice of Oncology, DeVita, V. T., Hellman, S., Rosenberg, S. A., 6th edition, Lippincott-Raven, Philadelphia, 2001), such as docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumab), ixabepilone, epothilones or derivatives thereof, and conjugates of cytotoxic drugs and antibodies against cell-surface receptors. Preferred therapeutic agents are platinum agents (such as carboplatin, oxaliplatin, cisplatin), taxanes (such as paclitaxel, docetaxel), gemcitabine, and camptothecin.

The one or more additional therapeutic agents can be administered before, concurrently, or after the multivalent polypeptides. The skilled artisan will understand that for each therapeutic agent there may be advantages to a particular order of administration. Similarly, the skilled artisan will understand that for each therapeutic agent, the length of time between which the agent, and an antibody, antibody fragment or conjugate of the invention is administered, will vary.

Formulation and Administration

The application further provides pharmaceutically acceptable compositions comprising the multivalent polypeptides described herein, wherein the composition is essentially endotoxin free. Therapeutic formulations comprising multivalent polypeptides are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Examples of combinations of active compounds are provided in herein. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins of the invention may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each therapeutic agent will be dependent on the identity of the agent, the preferred dosages can range from about 10 mg/square meter to about 2000 mg/square meter, more preferably from about 50 mg/square meter to about 1000 mg/square meter.

For therapeutic applications, the multivalent polypeptides are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The method of the present invention can be practiced in vitro, in vivo, or ex vivo.

Administration of multivalent polypeptides, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of multivalent polypeptides will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The protein is suitably administered to the patient at one time or over a series of treatments.

ADDITIONAL PATENT REFERENCES

Methods and compositions described in the following additional Patent Applications and Patents are also included in this disclosure:

U.S. Publication Nos. 20050186203; 20050084906; 20050008642; 20040202655; 20040132028; 20030211078; 20060083683; 20060099205; 20060228355; 20040081648; 20040081647; 20050074865; 20040259155; 20050038229; 20050255548; 20060246059; and U.S. Pat. Nos. 5,707,632; 6,818,418; and 7,115,396; and PCT International Application Publication Nos. WO2005/085430; WO2004/019878; WO2004/029224; WO2005/056764; WO2001/064942; and WO2002/032925.

INCORPORATION BY REFERENCE

All documents and references, including patent documents and websites, described herein are individually incorporated by reference to into this document to the same extent as if there were written in this document in full or in part.

---

SEQUENCE LISTING $^{10}$Fn3 with the BC, DE, and FG loops underlined (SEQ ID NO: 1)
VSDVPRDLEVVAATPTSLLI<u>SWDAPAVTVR</u>YYRITYGETGGNSPVQEFTV<u>PGSKST</u>ATISGLKPGVDYTITVYA
VT<u>GRGDSPASSKP</u>ISINYRT 385A08 BC loop
(SEQ ID NO: 2)
SWSARLKVAR 385A08 DE loop
(SEQ ID NO: 3)
PKNVYT 385A08 FG loop
(SEQ ID NO: 4)
TRFRDYQP V2B BC loop
(SEQ ID NO: 5)
SWRHPHFPTR V2B DE loop
(SEQ ID NO: 6)
PLQPPT V2B FG loop
(SEQ ID NO: 7)
TDGRNGRLLSIP 385A08-Fn-V2B (Ser tail)
(SEQ ID NO: 8)
MGVSDVPRDLEVVAATPTSLLISWSARLKVARYYRITYGETGGNSPVQEFTVPKNVYTATISGLKPGVDYTITV
YAVTRFRDYQPISINYRTEIDKPSTSTSTVSDVPRDLEVVAATPTSLLISWRHPHFPTRYYRITYGETGGNSPV
QEFTVPLQPPTATISGLKPGVDYTITVYAVTDGRNGRLLSIPISINYRTEIDKPSQ 385A08-Fn-V2B (Cys tail)
(SEQ ID NO: 9)
MGVSDVPRDLEVVAATPTSLLISWSARLKVARYYRITYGETGGNSPVQEFTVPKNVYTATISGLKPGVDYTITV
YAVTRFRDYQPISINYRTEIDKPSTSTSTVSDVPRDLEVVAATPTSLLISWRHPHFPTRYYRITYGETGGNSPV
QEFTVPLQPPTATISGLKPGVDYTITVYAVTDGRNGRLLSIPISINYRTEIDKPCQ 385A08-GS5 (SEQ ID NO: 21)-V2B (Ser tail)
(SEQ ID NO: 10)
MGVSDVPRDLEVVAATPTSLLISWSARLKVARYYRITYGETGGNSPVQEFTVPKNVYTATISGLKPGVDYTITV
YAVTRFRDYQPISINYRTEIDKGSGSGSGSGSVSDVPRDLEVVAATPTSLLISWRHPHFPTRYYRITYGETGGN
SPVQEFTVPLQPPTATISGLKPGVDYTITVYAVTDGRNGRLLSIPISINYRTEIDKPSQ

```
                              SEQUENCE LISTING

385A08-GS10 (SEQ ID NO: 22)-V2B (Ser tail)
                                                          (SEQ ID NO: 11)
MGVSDVPRDLEVVAATPTSLLISWSARLKVARYYRITYGETGGNSPVQEFTVPKNVYTATISGLKPGVDYTITV
YAVTRFRDYQPISINYRTEIDKGSGSGSGSGSGSGSGSGSVSDVPRDLEVVAATPTSLLISWRHPHFPTRYY
RITYGETGGNSPVQEFTVPLQPPTATISGLKPGVDYTITVYAVTDGRNGRLLSIPISINYRTEIDKPSQ V2B-Fn-385A08 (Ser tail)
                                                          (SEQ ID NO: 12)
MGVSDVPRDLEVVAATPTSLLISWRHPHFPTRYYRITYGETGGNSPVQEFTVPLQPPTATISGLKPGVDYTITV
YAVTDGRNGRLLSIPISINYRTEIDKPSTSTSTVSDVPRDLEVVAATPTSLLISWSARLKVARYYRITYGETGG
NSPVQEFTVPKNVYTATISGLKPGVDYTITVYAVTRFRDYQPISINYRTEIDKPSQ (SEQ ID NO: 2)

V2B-Fn-385A08 (Cys tail)
                                                          (SEQ ID NO: 13)
MGVSDVPRDLEVVAATPTSLLISWRHPHFPTRYYRITYGETGGNSPVQEFTVPLQPPTATISGLKPGVDYTITV
TYAVDGRNGRLLSIPISINYRTEIDKPSTSTSTVSDVPRDLEVVAATPTSLLISWSARLKVARYYRITYGETGG
NSPVQEFTVPKNVYTATISGLKPGVDYTITVYAVTRFRDYQPISINYRTEIDKPCQ V2B-GS5 (SEQ ID NO: 21)-385A08 (Ser tail)
                                                          (SEQ ID NO: 14)
MGVSDVPRDLEVVAATPTSLLISWRHPHFPTRYYRITYGETGGNSPVQEFTVPLQPPTATISGLKPGVDYTITV
YAVTDGRNGRLLSIPISINYRTEIDKGSGSGSGSGSVSDVPRDLEVVAATPTSLLISWSARLKVARYYRITYGE
TGGNSPVQEFTVPKNVYTATISGLKPGVDYTITVYAVTRFRDYQPISINYRTEIDKPSQ V2B-GS10 (SEQ ID NO: 22)-385A08 (Ser tail)
                                                          (SEQ ID NO: 15)
MGVSDVPRDLEVVAATPTSLLISWRHPHFPTRYYRITYGETGGNSPVQEFTVPLQPPTATISGLKPGVDYTITV
YAVTDGRNGRLLSIPISINYRTEIDKGSGSGSGSGSGSGSGSGSVSDVPRDLEVVAATPTSLLISWSARLKV
ARYYRITYGETGGNSPVQEFTVPKNVYTATISGLKPGVDYTITVYAVTRFRDYQPISINYRTEIDKPSQ V2B (Ser tail)
                                                          (SEQ ID NO: 16)
MGVSDVPRDLEVVAATPTSLLISWRHPHFPTRYYRITYGETGGNSPVQEFTVPLQPPTATISGLKPGVDYTITV
YAVTDGRNGRLLSIPISINYRTEIDKPSQ Ser tail
                                                          (SEQ ID NO: 17)
EIDKPSQ Cys tail
                                                          (SEQ ID NO: 18)
EIDKPCQ Short tail
                                                          (SEQ ID NO: 19)
EIDK Fn based linker
                                                          (SEQ ID NO: 20)
PSTSTST GS$_5$ linker
                                                          (SEQ ID NO: 21)
GSGSGSGSGS GS$_{10}$ linker
                                                          (SEQ ID NO: 22)
GSGSGSGSGSGSGSGSGSGS (GGGGS)$_3$
                                                          (SEQ ID NO: 23)
GGGGS GGGGS GGGGS (GGGGS)$_5$
                                                          (SEQ ID NO: 24)
GGGGS GGGGS GGGGS GGGGS GGGGS G$_4$SG$_4$SG$_3$SG
                                                          (SEQ ID NO: 25)
GGGGSGGGGSGGGSG AT577
                                                          (SEQ ID NO: 26)
MGVSDVPRDLEVVAATPTSLLISWSARLKVARYYRITYGETGGNSPVQEFTVPKNVYTATISGLKPGVDYTITV
YAVTRFRDYQPISINYRTEIDKPSQ
```

SEQUENCE LISTING

AT580

(SEQ ID NO: 27)
MGVSDVPRDLEVVAATPTSLLISWSARLKVARYYRITYGETGGNSPVQEFTVPKNVYTATISGLKPGVDYTITV
YAVTRFRDYQPISINYRTEIDKPCQ

V2B short (SEQ ID NO: 28)
GEVVAATPTSLLISWRHPHFPTRYYRITYGETGGNSPVQEFTVPLQPPTATISGLKPGVDYTITVYAVTDGRNG
RLLSIPISINYRTEIDKPCQ

385A08-GPG (SEQ ID NO: 32)-V2B (SEQ ID NO: 29)
MGVSDVPRDLEVVAATPTSLLISWSARLKVARYYRITYGETGGNSPVQEFTVPKNVYTATISGLKPGVDYTITV
YAVTRFRDYQPISINYRTGPGVSDVPRDLEVVAATPTSLLISWRHPHFPTRYYRITYGETGGNSPVQEFTVPLQ
PPTATISGLKPGVDYTITVYAVTDGRNGRLLSIPISINYRT

385A08-GPGPGPG (SEQ ID NO: 33)-V2B (SEQ ID NO: 30)
MGVSDVPRDLEVVAATPTSLLISWSARLKVARYYRITYGETGGNSPVQEFTVPKNVYTATISGLKPGVDYTITV
YAVTRFRDYQPISINYRTGPGPGPGVSDVPRDLEVVAATPTSLLISWRHPHFPTRYYRITYGETGGNSPVQEFT
VPLQPPTATISGLKPGVDYTITVYAVTDGRNGRLLSIPISINYRT

385A08-GPGPGPGPGPG (SEQ ID NO: 34)-V2B (SEQ ID NO: 31)
MGVSDVPRDLEVVAATPTSLLISWSARLKVARYYRITYGETGGNSPVQEFTVPKNVYTATISGLKPGVDYTITV
YAVTRFRDYQPISINYRTGPGPGPGPGPGVSDVPRDLEVVAATPTSLLISWRHPHFPTRYYRITYGETGGNSPV
QEFTVPLQPPTATISGLKPGVDYTITVYAVTDGRNGRLLSIPISINYRT (SEQ ID NO: 32)
GPG

GPGPGPG (SEQ ID NO: 33)

GPGPGPGPGPG (SEQ ID NO: 34)

385A08 Core (SEQ ID NO: 35)
EVVAATPTSLLISWSARLKVARYYRITYGETGGNSPVQEFTVPKNVYTATISGLKPGVDYTITVYAVTRFRDYQ
PISINYRT 385A08 Core with Full N-terminal Extension (underlined)

(SEQ ID NO: 36)
MGVSDVPRDLEVVAATPTSLLISWSARLKVARYYRITYGETGGNSPVQEFTVPKNVYTATISGLKPGVDYTITV
YAVTRFRDYQPISINYRT

385A08 Core with Full N-terminal Extension (underlined) and Short Tail (underlined)

(SEQ ID NO: 37)
MGVSDVPRDLEVVAATPTSLLISWSARLKVARYYRITYGETGGNSPVQEFTVPKNVYTATISGLKPGVDYTITV
YAVTRFRDYQPISINYRTEIDK

385A08 Core with N-terminal Extension (underlined) and Ser Tail (underlined)

(SEQ ID NO: 38)
VSDVPRDLEVVAATPTSLLISWSARLKVARYYRITYGETGGNSPVQEFTVPKNVYTATISGLKPGVDYTITVYA
VTRFRDYQPISINYRTEIDKPSQ

385A08 Core with N-terminal Extension (underlined) and Cys Tail (underlined)

(SEQ ID NO: 39)
VSDVPRDLEVVAATPTSLLISWSARLKVARYYRITYGETGGNSPVQEFTVPKNVYTATISGLKPGVDYTITVYA
VTRFRDYQPISINYRTEIDKPCQ

V2B Core (SEQ ID NO: 40)
EVVAATPTSLLISWRHPHFPTRYYRITYGETGGNSPVQEFTVPLQPPTATISGLKPGVDYTITVYAVTDGRNGR
LLSIPISINYRT V2B Core with N-terminal Extension (underlined)

(SEQ ID NO: 41)
VSDVPRDLEVVAATPTSLLISWRHPHFPTRYYRITYGETGGNSPVQEFTVPLQPPTATISGLKPGVDYTITVYA
VTDGRNGRLLSIPISINYRT

SEQUENCE LISTING

V2B Core with full N-terminal Extension (underlined) and Short Tail (underlined)

(SEQ ID NO: 42)

MGVSDVPRDLEVVAATPTSLLISWRHPHFPTRYYRITYGETGGNSPVQEFTVPLQPPTATISGLKPGVDYTITV
YAVTDGRNGRLLSIPISINYRTEIDK

V2B Core with full N-terminal Extension (underlined) and Ser Tail (underlined)

(SEQ ID NO: 43)

VSDVPRDLEVVAATPTSLLISWRHPHFPTRYYRITYGETGGNSPVQEFTVPLQPPTATISGLKPGVDYTITVYA
VTDGRNGRLLSIPISINYRTEIDKPSQ

V2B Core with full N-terminal Extension (underlined) and Cys Tail (underlined)

(SEQ ID NO: 44)

VSDVPRDLEVVAATPTSLLISWRHPHFPTRYYRITYGETGGNSPVQEFTVPLQPPTATISGLKPGVDYTITVYA
VTDGRNGRLLSIPISINYRTEIDKPCQ

Full N-Terminal Extension (SEQ ID NO: 45)

MGVSDVPRDL

N-Terminal Extension (SEQ ID NO: 46)

VSDVPRDL

N-Terminal Extension (SEQ ID NO: 48)

GVSDVPRDL

PA3 linker (SEQ ID NO: 60)

PAPAPA

PA6 linker (SEQ ID NO: 61)

PAPAPAPAPAPA

PA9 linker (SEQ ID NO: 62)

PAPAPAPAPAPAPAPAPA

385A08-Fn-V2B (Modified Ser tail)

(SEQ ID NO: 63)

MGVSDVPRDLEVVAATPTSLLISWSARLKVARYYRITYGETGGNSPVQEFTVPKNVYTATISGLKPGVDYTITV
YAVTRFRDYQPISINYRTEPSTSTSTVSDVPRDLEVVAATPTSLLISWRHPHFPTRYYRITYGETGGNSPVQEF
TVPLQPPTATISGLKPGVDYTITVYAVTDGRNGRLLSIPISINYRTEGSGS

385A08-Fn-V2B (Modified Cys tail)

(SEQ ID NO: 64)

MGVSDVPRDLEVVAATPTSLLISWSARLKVARYYRITYGETGGNSPVQEFTVPKNVYTATISGLKPGVDYTITV
YAVTRFRDYQPISINYRTEPSTSTSTVSDVPRDLEVVAATPTSLLISWRHPHFPTRYYRITYGETGGNSPVQEF
TVPLQPPTATISGLKPGVDYTITVYAVTDGRNGRLLSIPISINYRTEGSGC

385A08-PA3 (SEQ ID NO: 60)-V2B (Modified Ser tail)

(SEQ ID NO: 65)

MGVSDVPRDLEVVAATPTSLLISWSARLKVARYYRITYGETGGNSPVQEFTVPKNVYTATISGLKPGVDYTITV
YAVTRFRDYQPISINYRTEPAPAPAVSDVPRDLEVVAATPTSLLISWRHPHFPTRYYRITYGETGGNSPVQEFT
VPLQPPTATISGLKPGVDYTITVYAVTDGRNGRLLSIPISINYRTEGSGS

385A08-PA3 (SEQ ID NO: 60)-V2B (Modified Cys tail)

(SEQ ID NO: 66)

MGVSDVPRDLEVVAATPTSLLISWSARLKVARYYRITYGETGGNSPVQEFTVPKNVYTATISGLKPGVDYTITV
YAVTRFRDYQPISINYRTEPAPAPAVSDVPRDLEVVAATPTSLLISWRHPHFPTRYYRITYGETGGNSPVQEFT
VPLQPPTATISGLKPGVDYTITVYAVTDGRNGRLLSIPISINYRTEGSGC

385A08-PA6 (SEQ ID NO: 61)-V2B (Modified Ser tail)

(SEQ ID NO: 67)

MGVSDVPRDLEVVAATPTSLLISWSARLKVARYYRITYGETGGNSPVQEFTVPKNVYTATISGLKPGVDYTITV
YAVTRFRDYQPISINYRTEPAPAPAPAPAVSDVPRDLEVVAATPTSLLISWRHPHFPTRYYRITYGETGGNS
PVQEFTVPLQPPTATISGLKPGVDYTITVYAVTDGRNGRLLSIPISINYRTEGSGS

SEQUENCE LISTING

```
385A08-PA6 (SEQ ID NO: 61)-V2B (Modified Cys tail)
                                                          (SEQ ID NO: 68)
MGVSDVPRDLEVVAATPTSLLISWSARLKVARYYRITYGETGGNSPVQEFTVPKNVYTATISGLKPGVDYTITV
YAVTRFRDYQPISINYRTEPAPAPAPAPAPAPAVSDVPRDLEVVAATPTSLLISWRHPHFPTRYYRITYGETGGNS
PVQEFTVPLQPPTATISGLKPGVDYTITVYAVTDGRNGRLLSIPISINYRTEGSGC 385A08-PA9 (SEQ ID NO: 62)-V2B (Modified Ser tail)
                                                          (SEQ ID NO: 69)
MGVSDVPRDLEVVAATPTSLLISWSARLKVARYYRITYGETGGNSPVQEFTVPKNVYTATISGLKPGVDYTITV
YAVTRFRDYQPISINYRTEPAPAPAPAPAPAPAPAPAVSDVPRDLEVVAATPTSLLISWRHPHFPTRYYRITYG
ETGGNSPVQEFTVPLQPPTATISGLKPGVDYTITVYAVTDGRNGRLLSIPISINYRTEGSGS 385A08-PA9 (SEQ ID NO: 62)-V2B (Modified Cys tail)
                                                          (SEQ ID NO: 70)
MGVSDVPRDLEVVAATPTSLLISWSARLKVARYYRITYGETGGNSPVQEFTVPKNVYTATISGLKPGVDYTITV
YAVTRFRDYQPISINYRTEPAPAPAPAPAPAPAPAPAVSDVPRDLEVVAATPTSLLISWRHPHFPTRYYRITYG
ETGGNSPVQEFTVPLQPPTATISGLKPGVDYTITVYAVTDGRNGRLLSIPISINYRTEGSGC Modified Ser tail
                                                          (SEQ ID NO: 71)
EGSGS Modified Cys tail
                                                          (SEQ ID NO: 72)
EGSGC
```

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1. Multivalent Fibronectin Scaffold Domain Proteins, Including Several V/I $^{10}$Fn3-Based Binders Various constructs of multivalent fibronectin scaffold domain proteins were generated. The following table depicts constructs described herein and their SEQ ID NOS.

| Construct | Description | SEQ ID NO: |
|---|---|---|
| 385A08-Fn-V2B | A bivalent I/V construct having the structure (SEQ ID NO: 37)-(SEQ ID NO: 20)-(SEQ ID NO: 43) | 8 |
| 385A08-Fn-V2B-Cys | A bivalent I/V construct having the structure (SEQ ID NO: 37)-(SEQ ID NO: 20)-(SEQ ID NO: 44) | 9 |
| 385A08-GS5 (SEQ ID NO: 21)-V2B | A bivalent I/V construct having the structure (SEQ ID NO: 37)-(SEQ ID NO: 21)-(SEQ ID NO: 43) | 10 |
| 385A08-GS10 (SEQ ID NO: 22)-V2B | A bivalent I/V construct having the structure (SEQ ID NO: 37)-(SEQ ID NO: 22)-(SEQ ID NO: 43) | 11 |
| V2B-Fn-385A08 | A bivalent V/I construct having the structure (SEQ ID NO: 42)-(SEQ ID NO: 20)-(SEQ ID NO: 38) | 12 |
| V2B-Fn-385A08-Cys | A bivalent V/I construct having the structure (SEQ ID NO: 42)-(SEQ ID NO: 20)-(SEQ ID NO: 39) | 13 |
| V2B-GS5 (SEQ ID NO: 21)-385A08 | A bivalent V/I construct having the structure (SEQ ID NO: 42)-(SEQ ID NO: 21)-(SEQ ID NO: 38) | 14 |
| V2B-GS10 (SEQ ID NO: 22)-385A08 | A bivalent V/I construct having the structure (SEQ ID NO: 42)-(SEQ ID NO: 22)-(SEQ ID NO: 38) | 15 |
| 385A08-GPG (SEQ ID NO: 32)-V2B | A bivalent I/V construct having the structure (SEQ ID NO: 36)-(SEQ ID NO: 32)-(SEQ ID NO: 41) | 29 |
| 385A08-GPGPGPG (SEQ ID NO: 33)-V2B | A bivalent I/V construct having the structure (SEQ ID NO: 36)-(SEQ ID NO: 33)-(SEQ ID NO: 41) | 30 |
| 385A08-GPGPGPGPG (SEQ ID NO: 34)-V2B | A bivalent I/V construct having the structure (SEQ ID NO: 36)-(SEQ ID NO: 34)-(SEQ ID NO: 41) | 31 |

-continued

| Construct | Description | SEQ ID NO: |
|---|---|---|
| V2BShort | A VEGFR2 binder having the V2B Core with a Gly at the N-terminus and the Cys tail; the structure is Gly-(SEQ ID NO: 40)-(SEQ ID NO: 18) | 28 |
| Peg-V2Bshort | V2B Short which is pegylated at position 93 | 28 |
| V2B (Ser tail) | A VEGFR2 binder having the V2B Core with a full N-terminal extension and a Ser tail; the structure is (SEQ ID NO: 45)-(SEQ ID NO: 40)-(SEQ ID NO: 17) | 16 |
| AT577 | An IGF-IR binder having the 385A08 Core with a full N-terminal extension and a Ser tail; the structure is (SEQ ID NO: 45)-(SEQ ID NO: 35)-(SEQ ID NO: 17) | 26 |
| AT580 | An IGF-IR binder having the 385A08 Core with a full N-terminal extension and a Cys tail; the structure is (SEQ ID NO: 45)-(SEQ ID NO: 35)-(SEQ ID NO: 18) | 27 |
| AT580-PEG40 | AT580 which has been pegylated with a 40 kDa PEG at position 98 | 27 |
| AT580-PEG20-AT580 | A bivalent I/I construct which has two AT580 molecules attached via a 20 kDa PEG molecule at position 98 of each molecule | 27 |
| 385A08 Core | 385A08 is an exemplary IGF-IR binder | 35 |
| | An IGF-IR binder having the 385A08 Core with Full N-terminal Extension; the structure is (SEQ ID NO: 35)-(SEQ ID NO: 45) | 36 |
| | An IGFR-IR binder having the 385A08 Core with Full N-terminal Extension and Short Tail; the structure is (SEQ ID NO: 45)-(SEQ ID NO: 35)-(SEQ ID NO: 19) | 37 |
| | An IGFR-IR binder having the 385A08 Core with N-terminal Extension and Ser Tail; the structure is (SEQ ID NO: 46)-(SEQ ID NO: 35)-(SEQ ID NO: 17) | 38 |
| | An IGFR-IR binder having the 385A08 Core with N-terminal Extension and Ser Tail; the structure is (SEQ ID NO: 46)-(SEQ ID NO: 35)-(SEQ ID NO: 18) | 39 |
| V2B Core | V2B is an exemplary VEGFR2 binder | 40 |
| | A VEGFR2 binder having the V2B Core with N-terminal Extension; the structure is (SEQ ID NO: 46)-(SEQ ID NO: 40) | 41 |
| | A VEGFR2 binder having the V2B Core with Full N-terminal Extension and Short Tail; the structure is (SEQ ID NO: 45)-(SEQ ID NO: 40)-(SEQ ID NO: 19) | 42 |
| | A VEGFR2 binder having the V2B Core with Full N-terminal Extension and Ser Tail; the structure is (SEQ ID NO: 45)-(SEQ ID NO: 40)-(SEQ ID NO: 17) | 43 |
| | A VEGFR2 binder having the V2B Core with Full N-terminal Extension and Cys Tail; the structure is (SEQ ID NO: 45)-(SEQ ID NO: 40)-(SEQ ID NO: 18) | 44 |
| 385A08-Fn-V2B (Modified Ser tail) | A bivalent I/V construct having the structure (SEQ ID NO: 36)-E-(SEQ ID NO: 20)-(SEQ ID NO: 41)-(SEQ ID NO: 71) | 63 |
| 385A08-Fn-V2B (Modified Cys tail) | A bivalent I/V construct having the structure (SEQ ID NO: 36)-E-(SEQ ID NO: 20)-(SEQ ID NO: 41)-(SEQ ID NO: 72) | 64 |
| 385A08-PA3 (SEQ ID NO: 60)-V2B (Modified Ser tail) | A bivalent I/V construct having the structure (SEQ ID NO: 36)-E-(SEQ ID NO: 60)-(SEQ ID NO: 41)-(SEQ ID NO: 71) | 65 |
| 385A08-PA3 (SEQ ID NO: 60)-V2B (Modified Cys tail) | A bivalent I/V construct having the structure (SEQ ID NO: 36)-E-(SEQ ID NO: 60)-(SEQ ID NO: 41)-(SEQ ID NO: 72) | 66 |
| 385A08-PA6 (SEQ ID NO: 61)-V2B (Modified Ser tail) | A bivalent I/V construct having the structure (SEQ ID NO: 36)-E-(SEQ ID NO: 61)-(SEQ ID NO: 41)-(SEQ ID NO: 71) | 67 |
| 385A08-PA6 (SEQ ID NO: 61)-V2B (Modified Cys tail) | A bivalent I/V construct having the structure (SEQ ID NO: 36)-E-(SEQ ID NO: 61)-(SEQ ID NO: 41)-(SEQ ID NO: 72) | 68 |
| 385A08-PA9 (SEQ ID NO: 62)-V2B (Modified Ser tail) | A bivalent I/V construct having the structure (SEQ ID NO: 36)-E-(SEQ ID NO: 62)-(SEQ ID NO: 41)-(SEQ ID NO: 71) | 69 |

-continued

| Construct | Description | SEQ ID NO: |
|---|---|---|
| 385A08-PA9 (SEQ ID NO: 62)-V2B (Modified Cys tail) | A bivalent I/V construct having the structure (SEQ ID NO: 36)-E-(SEQ ID NO: 62)-(SEQ ID NO: 41)-(SEQ ID NO: 72) | 70 |

385A08 is an exemplary IGF-IR binder. V2B is an exemplary VEGFR2 binder. The two domains are linked by either glycine-serine based linkers (e.g., GS5, SEQ ID NO: 21, and GS10, SEQ ID NO: 22) or a modified stretch of amino acids that connect the first and second human Fn3 domains (SEQ ID NO: 20). These V/I $^{10}$Fn3-based binders can be oriented in different ways—for instance, the V2B domain at the N-terminus, or the IGF-IR domain at the N-terminus. Peg-V2Bshort is a construct lacking the first eight amino acids of the fibronectin based scaffold domain of V2B and is pegylated at its single cysteine residue. AT577 is an IGF-IR binder with a C-terminal tail of SEQ ID NO: 17. AT580 is an IGF-IR binder with a C-terminal tail of SEQ ID NO: 18. Specifically, AT580 is represented by SEQ ID NO: 27. AT580-Peg20-AT580 are two IGF-IR binders connected via their single cysteine residues with a PEG linkage. AT580-PEG40 is an IGF-IR binder (SEQ ID NO: 27) that has a 40 kD peg attached. The multivalent constructs used in the following experiments generally contain a C-terminal His6 tag (SEQ ID NO: 59).

Example 2: Expression of V/I $^{10}$Fn3-Based Binders

Certain V/I $^{10}$Fn3-based binders were purified using a high throughput protein production process (HTPP) as described in the materials and methods section below. FIG. 1 depicts an exemplary SDS-PAGE analysis from several of the V/I $^{10}$Fn3-based binders, including those linked by an Fn linker, GS5 linker (SEQ ID NO: 21), and GS10 linker (SEQ ID NO: 22). FIG. 1 demonstrates acceptable expression levels for the multiple constructs that were tested. Additionally, select clones were also purified using a mid-scale purification process, which encompassed the purification of insoluble binders. An alternative method can also be used, which encompasses purification of soluble binders. These mid-scale purification processes are described in the materials and methods section below. Some specific clones were also purified using a large scale purification process, which is described in the materials and methods section below.

Example 3: Biophysical Characterization of V/I $^{10}$Fn3-Based Binders

Standard size exclusion chromatography (SEC) was performed on certain HTPP, midscale and large scale purified V/I $^{10}$Fn3-based binders. Mass spectrometry (LC-MS) and differential scanning calorimetry (DSC) analyses were also performed on certain of these constructs that were purified from midscale and large scale processes. Each of these analytical methods are described in the materials and methods section below.

Figure 2:
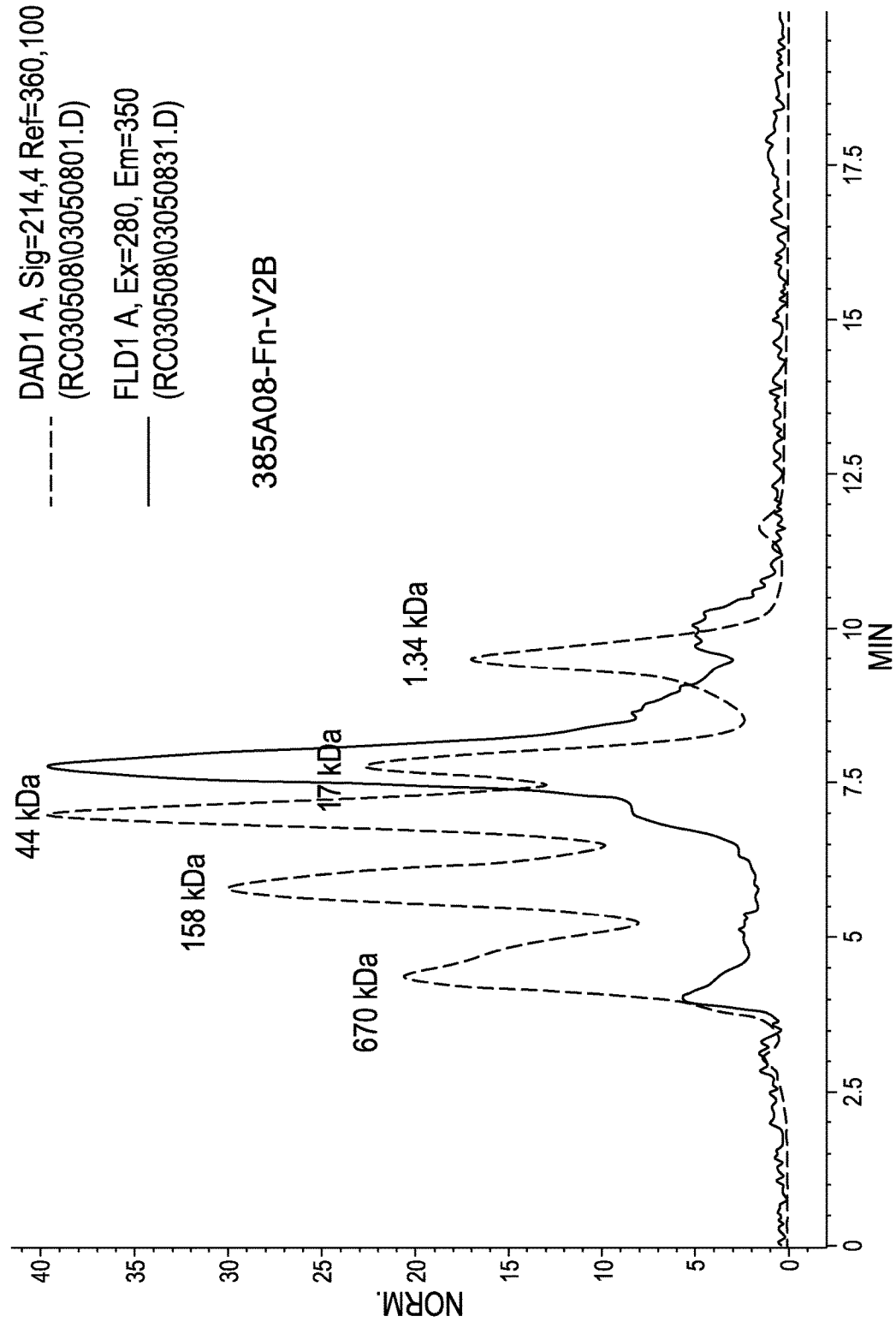
FIG. 2. SEC of HTPP purified construct 385A08-Fn-V2B demonstrates predominantly monomeric protein FIG. 3. SEC of HTPP purified construct V2B-Fn-385A08 demonstrates a mixture of monomeric and dimeric protein FIG. 4. Molecular Weight as measured by LC-MS and Tm determination by DSC for certain V/I $^{10}$Fn3-based binders. As shown: 'GS10' (SEQ ID NO: 22).
Figure 3:
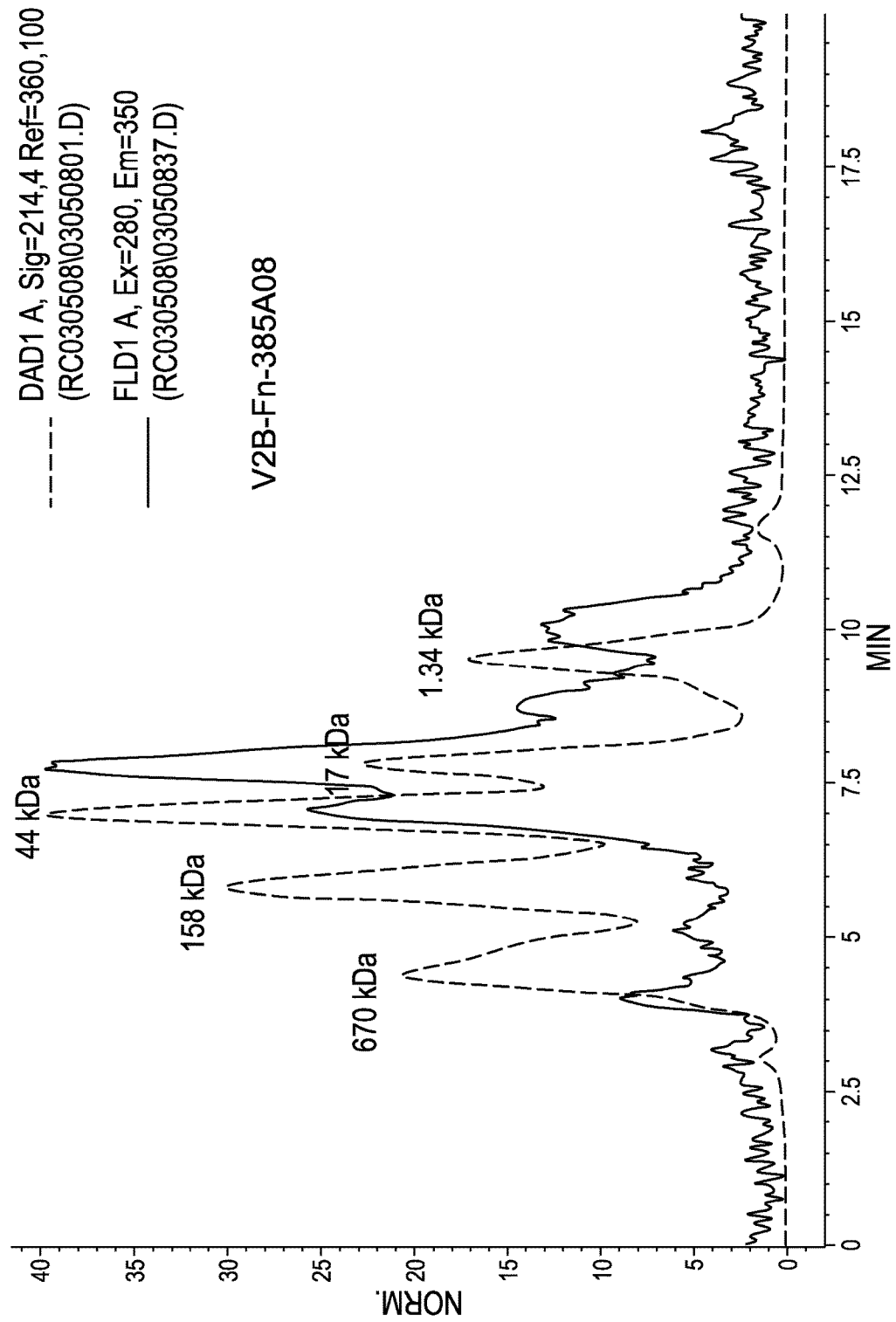

SEC results of the HTPP purified constructs varied depending on the orientation of the 385A08 (IGF-IR domain) or V2B (VEGFR-2 domain) subunits within the tandem. With the 385A08 subunit on the N-terminal side (i.e., 385A08-Fn-V2B with a his-tag), SEC showed predominantly monomeric protein (eluted in the 23 kDa range vs. globular molecular weight standards), as shown in FIG. 2. On the other hand, when the V2B subunit is on the N-terminal side (i.e., V2B-Fn-385A08 with a his-tag, SEQ ID NO: 8), this resulted in a mixture of monomer (23 kDa) and dimer (46 kDa vs. globular molecular weight standards), as shown in FIG. 3. SEC analysis of constructs where a GS5 (SEQ ID NO: 21) or GS10 linker (SEQ ID NO: 22) was used instead of an Fn linker showed similar results, depending on the orientation of the 385A08 and V2B subunits.

SECs of midscale purified constructs 385A08-Fn-V2B (SEQ ID NO: 8) and 385A08-Fn-V2B-cys (SEQ ID NO: 9) were also evaluated. For the midscale purified construct 385A08-Fn-V2B (which has a his-tag, and includes a naturally occurring serine at the C-terminus), the SEC profile was predominantly monomeric with elution in the approximate range of 23 kDa based on globular molecular weight standards. However, for the cysteine version of this construct (385A08-Fn-V2B-cys with a his-tag), the SEC demonstrated a mixture of monomeric and dimeric protein. It should be noted that the cysteine version is typically created for pegylation purposes. Equivalent results were observed for solubly expressed and purified 385A08-Fn-VB2 (with his tag) and material that was expressed in an insoluble form and refolded.

Select midscale constructs were further analyzed by LC-MS. The molecular weight measured by LC-MS for 385A08-Fn-V2B (with his tag) is 23,260 Daltons, which matches the molecular weight of the "desMet form" (a version of the tandem where the first methionine is cleaved off) calculated from amino acid composition of the tandem. The molecular weight measured by LC-MS for 385A08-Fn-V2B-Cys (with a his-tag) is 23,581 Daltons, which is +174 Daltons of the theoretical calculated molecular weight based on the amino acid composition of the tandem indicating a post translational modification most likely of the Cys residue. In addition, the LC-MS for 385A08-GS10 (SEQ ID NO: 22)-V2B (with his-tag, SEQ ID NO: 11) is 24,040, matching the theoretical molecular weight for this construct. See FIG. 4.

In addition, Differential Scanning calorimetry (DSC) analysis was performed on two of the midscale purified constructs. The experimentally determined $T_m$ of 385A08-Fn-V2B (with his tag) in 50 mM NaOAc, 150 mM NaCl, pH 4.5 is equal to 51.49° C. The DSC of 385A08-Fn-V2B-Cys (with his tag) in 50 mM NaOAc, 150 mM NaCl, pH 4.5 showed two transition states of 46.77° C. & 55.52° C. which is probably due to the presence of dimer due to disulfide bond formation between two tandems (See FIG. 4).

Figure 5:
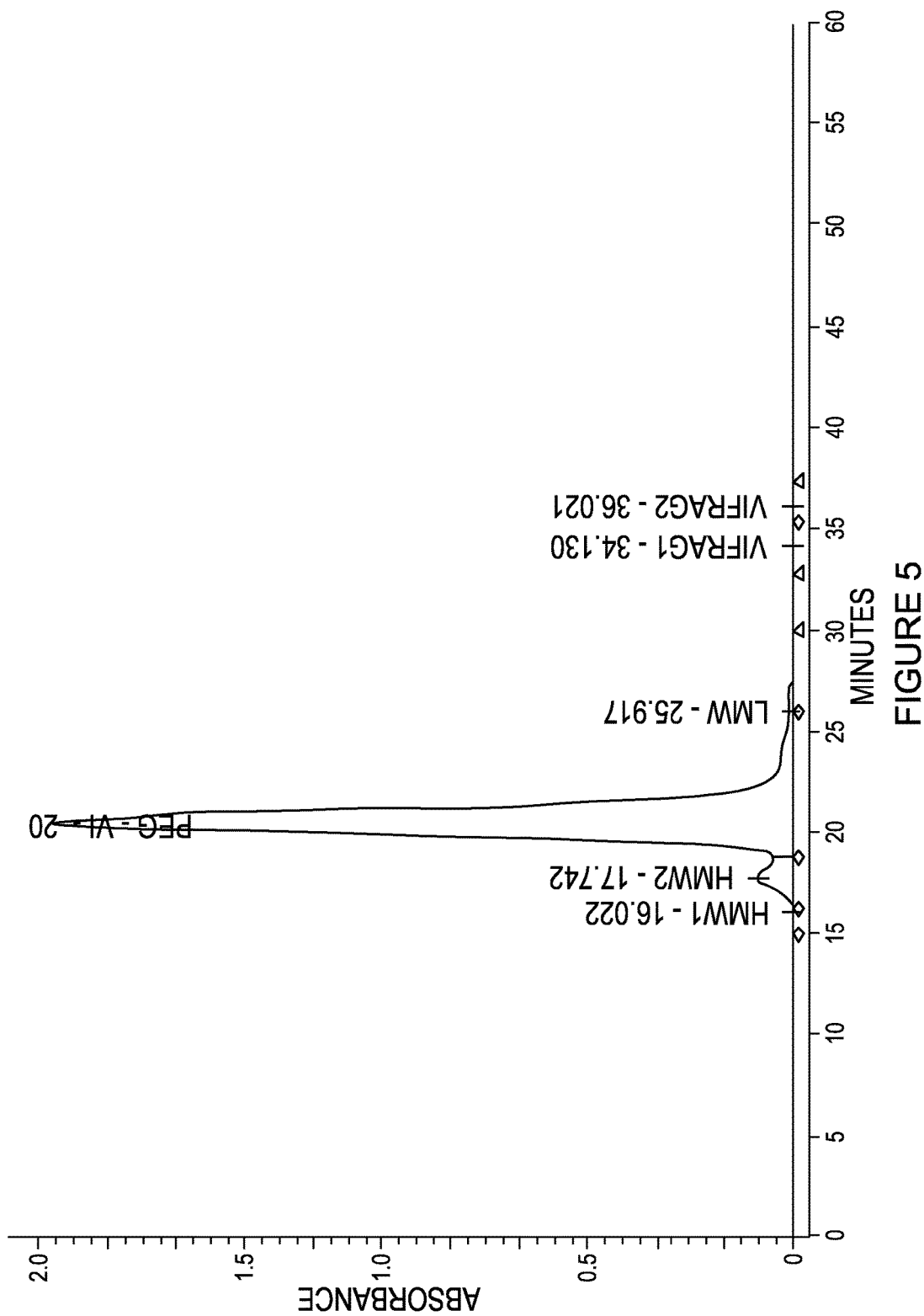
FIG. 5. SEC of 385A08-Fn-V2B-cys (pegylated, no his-tag) demonstrates that this protein is 95.1% monomeric.
Figure 6:
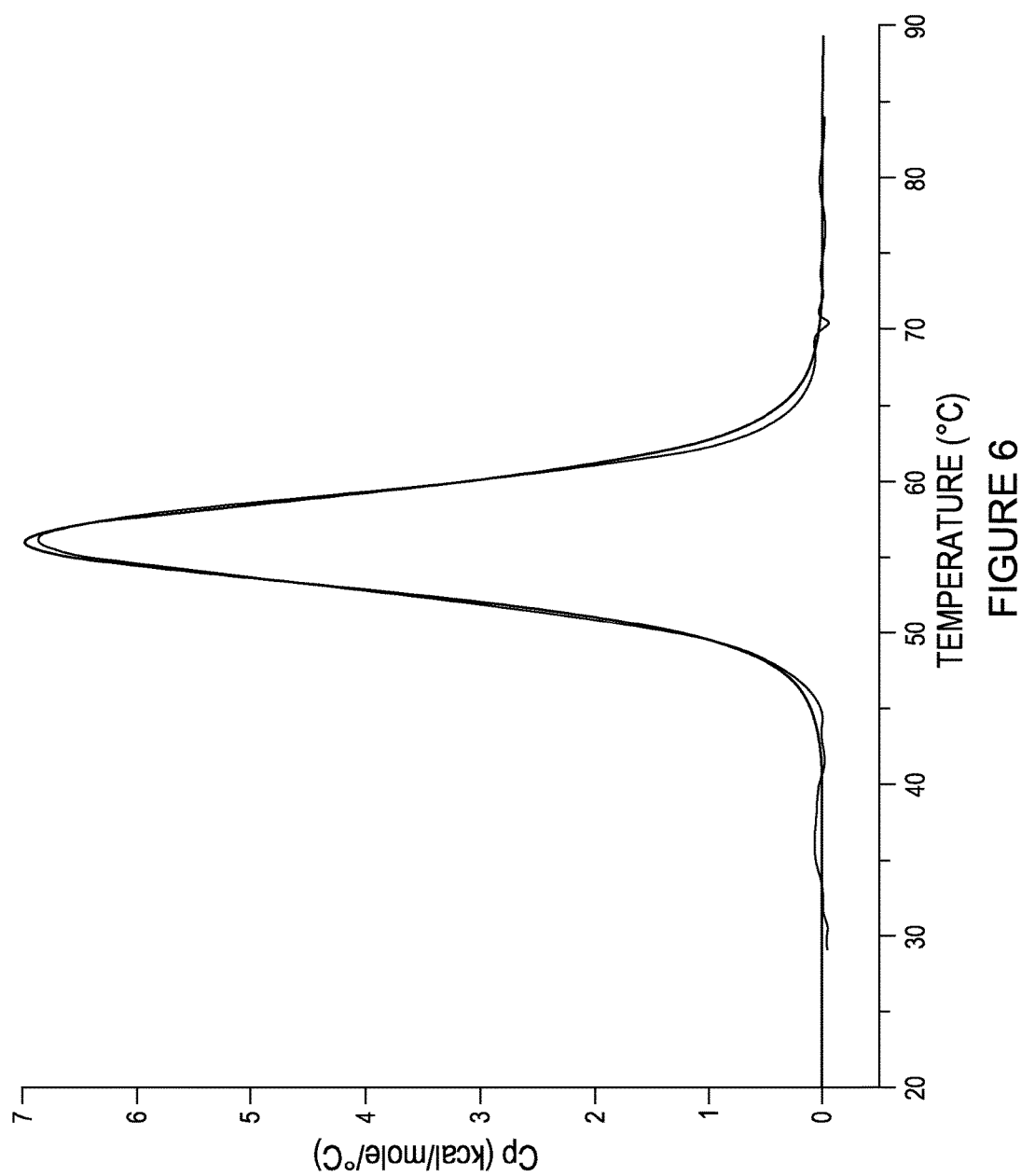
FIG. 6. DSC analysis of 385A08-Fn-V2B-cys (pegylated, no his-tag) demonstrated that the protein was half unfolded at 56° C., and no unfolding was detected up to 45° C.

SEC was also performed on large-scale purified, pegylated 385A08-Fn-V2B-cys (no his tag, SEQ ID NO: 9). SEC of this construct demonstrated material that was 95.1% monomeric as shown in FIG. 5. In addition, DSC analysis on this same construct demonstrated that it was half unfolded at a temperature of 56° C. (see FIG. 6) with no unfolding detected at up to 45° C.

Example 4: Effects of Pegylation on Multivalent Fibronectin Based Proteins

The fibronectin based scaffold proteins can be pegylated according to the method described below. Various types of PEG, such as linear or branched PEGs, and various sized PEGs can be used. In particular, midscale and large scale purified versions of the construct 385A08-Fn-V2B-Cys (SEQ ID NO: 9) were pegylated with 40 kD linear and 40 kD branched PEG.

Figure 7:
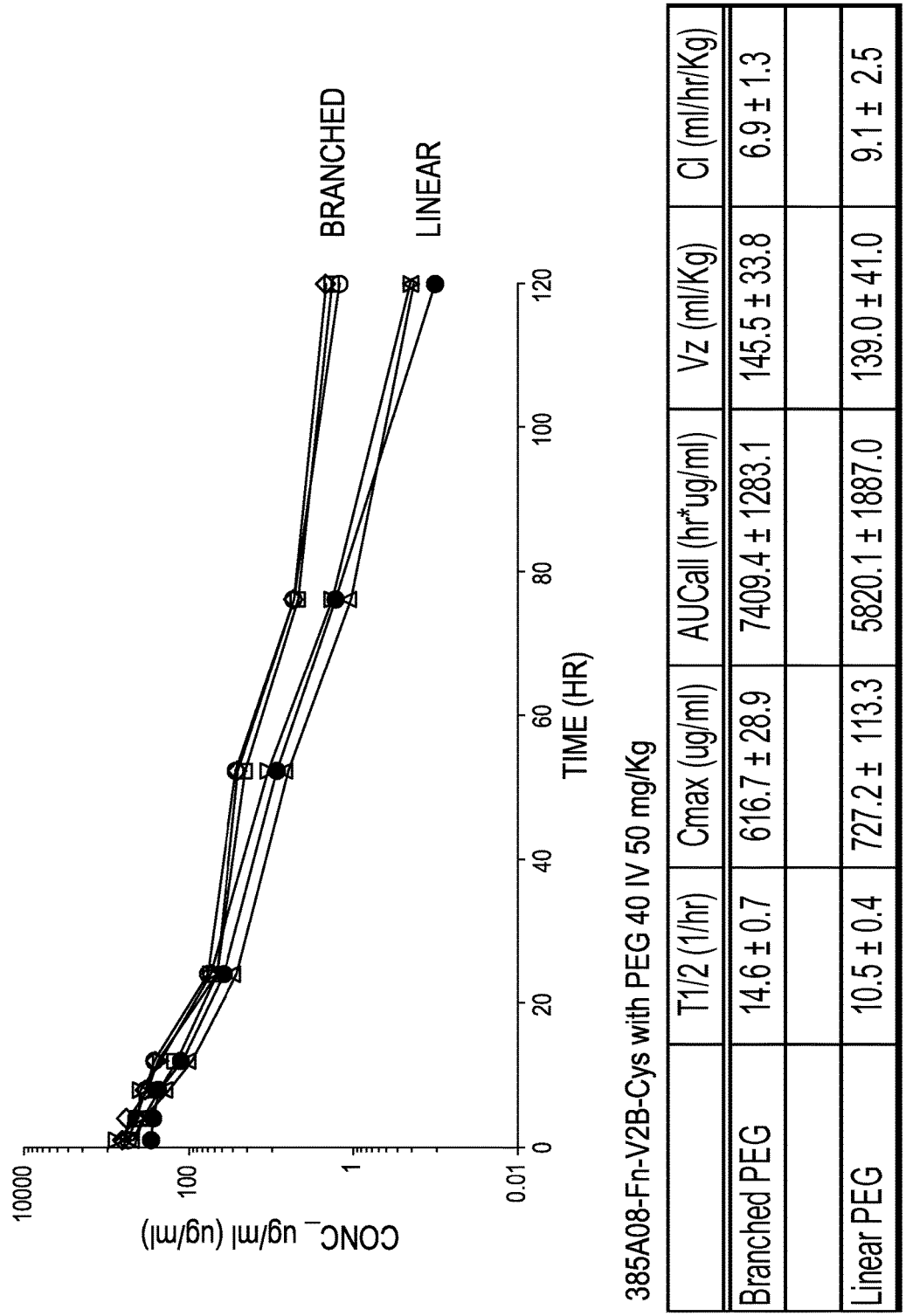
FIG. 7. Mice dosed with a 40 kD branched or linear pegylated version of construct 385A08-Fn-V2B-Cys demonstrated half life of 14.6 hours for branched vs. 10.5 hours for linear. Several individual mice were dosed with the branched or linear pegylated version of the construct as indicated in the figure.

An analysis of drug concentration over a 120 hour period in mice revealed that his-tagged 385A08-Fn-V2B-Cys with branched PEG demonstrated a half life of 14.6 hours, while the linear pegylated version of this construct (with his tag) demonstrated a half life of 10.5 hours (FIG. 7). Details of the dosing schedule and half life calculations are described in the materials and methods section below. All concentrations of Adnectin reported here and in the rest of the document are based on the protein and not the PEG portion of the compound.

Example 5. Determination of Binding Affinity Using Surface Plasmon Resonance (BIAcore) Analysis on Multivalent Fibronectin Based Proteins Selected HTPP purified fibronectin based scaffold proteins, including several V/I $^{10}$Fn3-based binders, were evaluated for their kinetic behavior towards IGF-IR using surface plasmon resonance as described in the materials and methods section below. The dissociation constant, $K_D$, for these clones is shown in the first column of FIG. 8.

A concentration series of the midscale purification of the tandem construct 385A08-Fn-V2B (non pegylated, his-tagged version, SEQ ID NO: 8) was also evaluated. The functionality of each of the domains of this construct, specifically, the V2B domain, and the IGF-IR domain, was evaluated as described in the materials and methods section below. With respect to the V2B domain, the $K_D$ of 385A08-Fn-V2B for VEGFR2-Fc was ~0.3 nM with an average on rate of $1.4 \times 10^6$ M$^{-1}$ sec$^{-1}$, the average off rate was $4.5 \times 10^{-4}$ sec$^{-1}$. With respect to the IGF-IR domain, the $K_D$ of 385A08-Fn-V2B for IGF-IR-Fc was ~20 pM with an on rate of $1.1 \times 10^7$ M$^{-1}$ sec$^{-1}$ and an off rate of $1.7 \times 10^{-4}$ sec$^{-1}$ (n of 1).

Data was also collected for midscale purified material of the tandem 385A08-GS10 (SEQ ID NO: 22)-V2B (SEQ ID NO: 11) and V2B-GS10 (SEQ ID NO: 22)-385A08 (SEQ ID NO: 15). Both constructs included a his-tag. The $K_D$ for the IGF-IR domain was 40 pM and 50 pM, respectively. The $K_D$ for the V2B domain was 0.5 nM and 0.6 nM, respectively. Additional data was collected for a linear pegylated, his-tagged midscale purified version of construct 385A08-Fn-V2B-cys (SEQ ID NO: 9). The $K_D$ for the IGF-IR domain was 1.2 nM. The $K_D$ for the V2B domain was 14 nM. These data are shown in FIG. 9.

Affinity data was also measured from midscale and large scale material, for the pegylated version of the tandem construct 385A08-Fn-V2B-cys (SEQ ID NO: 9), with and without his tag). The specific materials and methods for these calculations are described below. The results show that the various constructs tested bound to IGF1R-Fc with an average on-rate of 3.15E+05 M$^{-1}$ s$^{-1}$+/-0.94E+05 M$^{-1}$ s$^{-1}$, and an average off-rate of 2.47E-04 s$^{-1}$+/-0.18E-04 s$^{-1}$. For VEGFR2-Fc, the measured average association rate was 1.15E+04 M$^{-1}$s$^{-1}$+/-0.62E+04 M$^{-1}$s$^{-1}$, and the dissociation rate was 1.02E-04 s$^{-1}$+/-0.21E-04 s$^{-1}$. These data are shown in FIG. 10. The average calculated affinities for VEGFR2 and IGF1R using this experimental format are 10.5±0.48 nM and 0.84±0.22 nM, respectively.

Example 6: Competitive IGF1R and Competitive VEGFR-2 Blocking Assays

Figure 11:
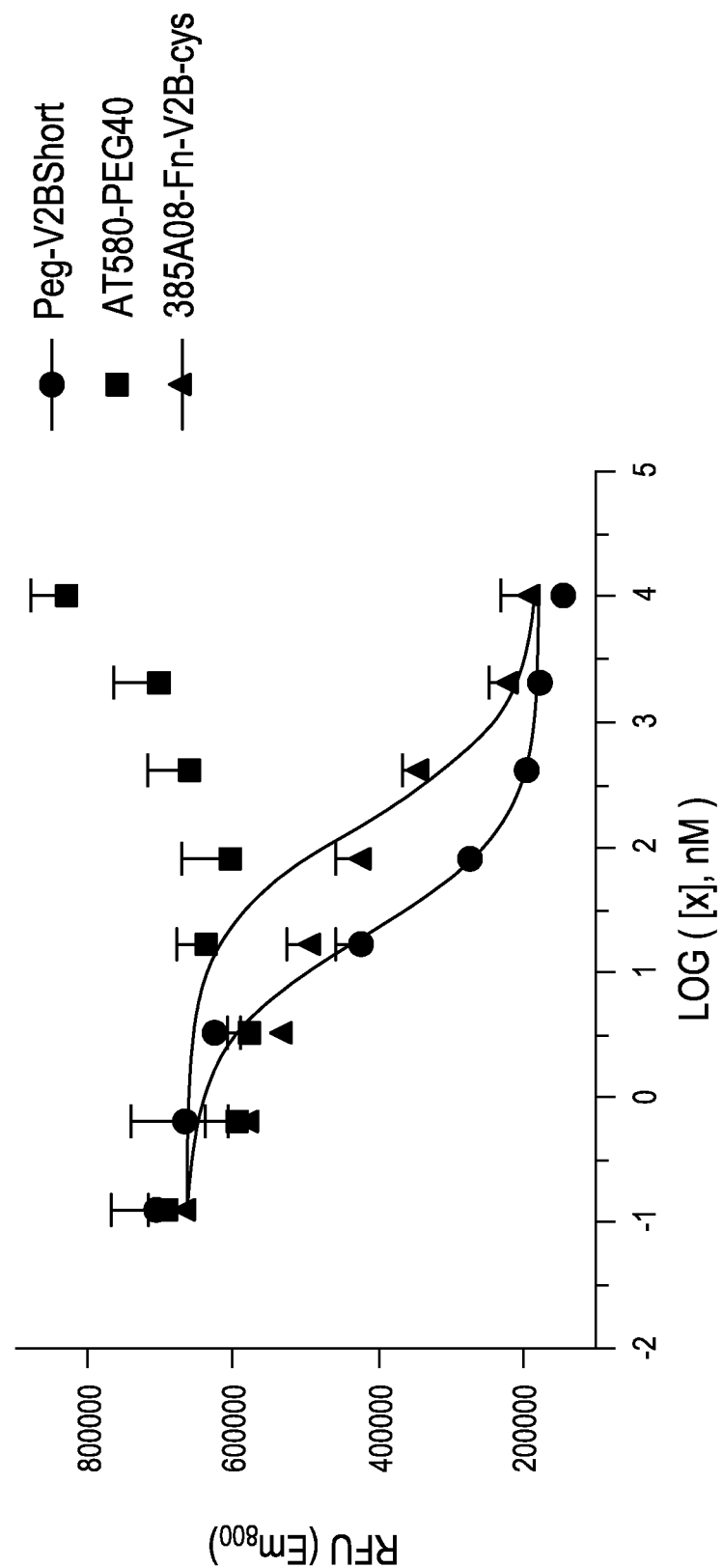
FIG. 11. The relative ability of Peg-V2BShort and 385A08-Fn-V2B-cys (with PEG and his-tag) to compete with labeled Peg-V2BShort for cell bound VEGFR-2 was evaluated on the cell line 293:KDR FIG. 12. The relative ability of AT580-PEG40 and 385A08-Fn-V2B-cys (with PEG and his-tag) to compete with labeled AT580-PEG20-AT580 for cell bound IGF-IR was evaluated on the cell line R+.

Certain tandem constructs were evaluated for their ability to compete with mono-specific IGF-IR and VEGFR-2 binders in vitro. In particular, a pegylated, his-tagged version of the construct 385A08-Fn-V2B-cys (SEQ ID NO: 9) was shown to disrupt the interaction of a mono-specific IGF-IR $^{10}$Fn3-based binder (AT580-PEG40, SEQ ID NO: 27) with cell surface IGF-IR. Using the cell line R$^+$, which overexpresses IGF-IR, we have shown that the IC$_{50}$ for blocking the interaction of a high affinity bivalent $^{10}$Fn3-based IGF1R binder (AT580-PEG20-AT580, SEQ ID NO: 27) was 900 nM for pegylated, his-tagged 385A08-Fn-V2B-cys, whereas it was 600 nM for AT580-PEG40. This suggests that pegylated, his-tagged 385A08-Fn-V2B-cys has IGF-IR affinity similar to that of AT580-PEG40. FIG. 11 demonstrates this data.

Figure 12:
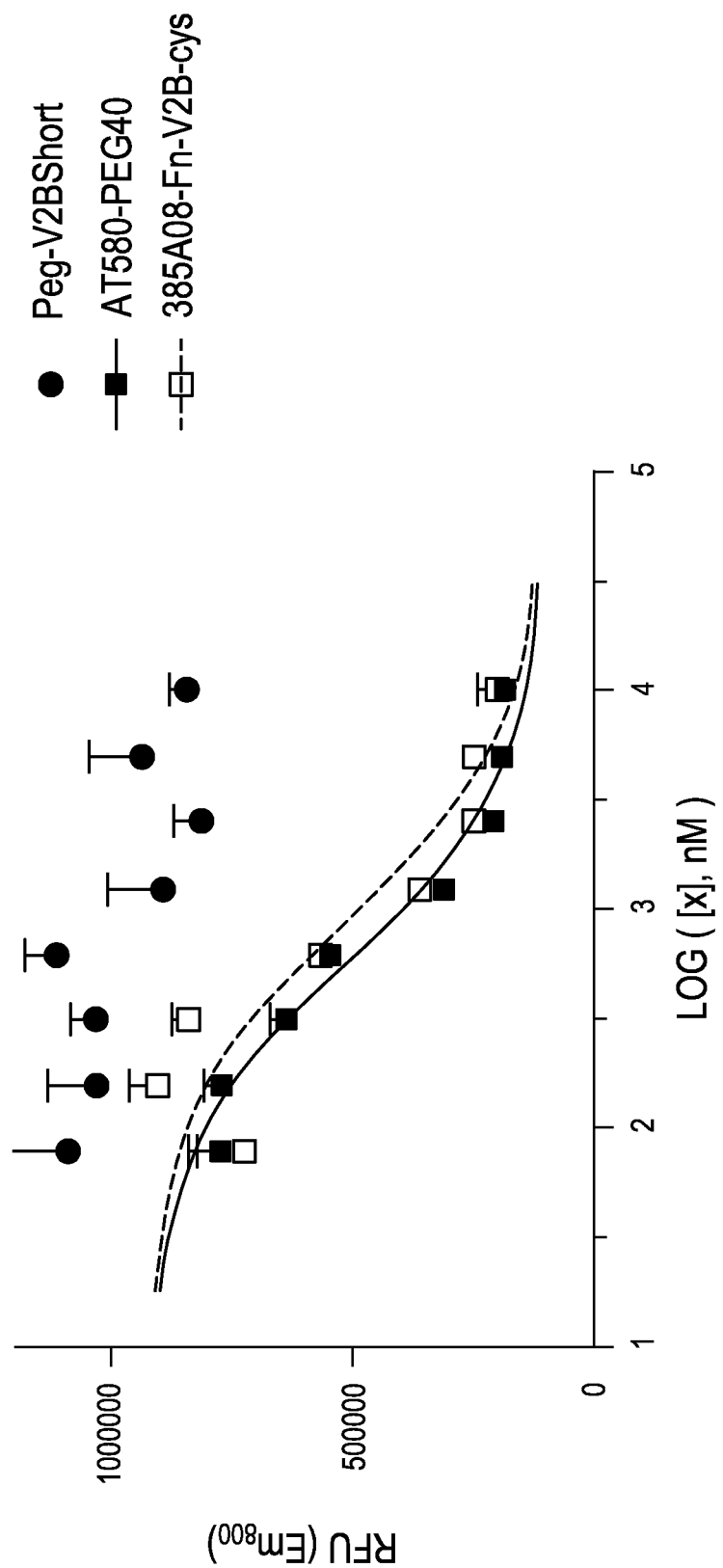

Similarly, the pegylated, his-tagged construct 385A08-Fn-V2B-cys was able to block the interaction of a mono-specific $^{10}$Fn3-based VEGFR-2 binder (Peg-V2Bshort, SEQ ID NO: 28) with VEGFR-2 present on 293:KDR cells. Results from the 293:KDR assay demonstrated an IC$_{50}$ of approximately 140 nM for the pegylated, his-tagged construct 385A08-Fn-V2B-cys, whereas that of Peg-V2Bshort is approximately 20 nM (see FIG. 12). The 7-fold difference in activity between Peg-V2Bshort and the pegylated, his-tagged construct 385A08-Fn-V2B-cys is consistent with the fact that the VEGFR-2 binding portion of 385A08-Fn-V2B-cys has approximately a 5-fold lower affinity for VEGFR-2 as compared to Peg-V2Bshort. In particular, in a Ba/F3 assay (described below), the IC$_{50}$ for the monomeric, non-pegylated VEGFR2 binder V2Bshort (SEQ ID NO: 28) is approximately 0.1-3 nM whereas the IC$_{50}$ for the monomeric, non-pegylated VEGFR2 binder having SEQ ID NO: 44 (e.g., with an N-terminal extension) is approximately 8-13 nM. Therefore, the version of the VEGFR2 binder included in the tandem construct (e.g., having SEQ ID NO: 44 which includes an N-terminal extension) has an approximately 5-fold lower affinity for VEGFR2 as compared to the monomeric VEGFR2 binder used in this assay (e.g., having SEQ ID NO: 28). Both the R$^+$ and 293:KDR cell based competitive blocking assays are described in detail in the materials and methods section below.

Example 7. In Vitro Proliferation Assays

Certain purified constructs, including several V/I $^{10}$Fn3-based binders, were evaluated in Ba/F3 and Rh41 cell-based assays in order to confirm activity. IC50s are depicted in FIG. 8 (columns 2, 3). In addition, certain purified constructs were evaluated in Rh41 and HMVEC-L proliferation assays (also described in the materials and methods section below). These constructs were compared to a mono-specific antibody directed to IGF1R (MAB391), a mono-specific antibody to VEGF (bevacizumab), another mono-specific $^{10}$Fn3-based IGF1R binder (AT-577, SEQ ID NO: 26), a mono-specific $^{10}$Fn3-based VEGFR-2 binder (Peg-V2Bshort, SEQ ID NO: 28), and a wild type $^{10}$Fn3-based protein that does not bind to a target (SGE). The data demonstrates that neither the orientation of the tandem (e.g., whether the I portion or the V portion is at the N-terminus) or the choice of linker affected the results. This data is summarized in FIG. 13. In addition, Ba/F3 and NCI-H929 cell proliferation assays were performed to compare certain his-tag and non-his-tag versions of the pegylated construct 385A08-Fn-V2B-Cys (SEQ ID NO: 9). These constructs were compared to MAB391, mono-specific $^{10}$Fn3-based IGF-IR binder AT580-PEG40 (SEQ ID NO: 27), and monospecific [10]Fn3-based VEGFR2 binder Peg-V2Bshort (SEQ ID NO: 28). These data are summarized in FIG. 14.

Figure 15:
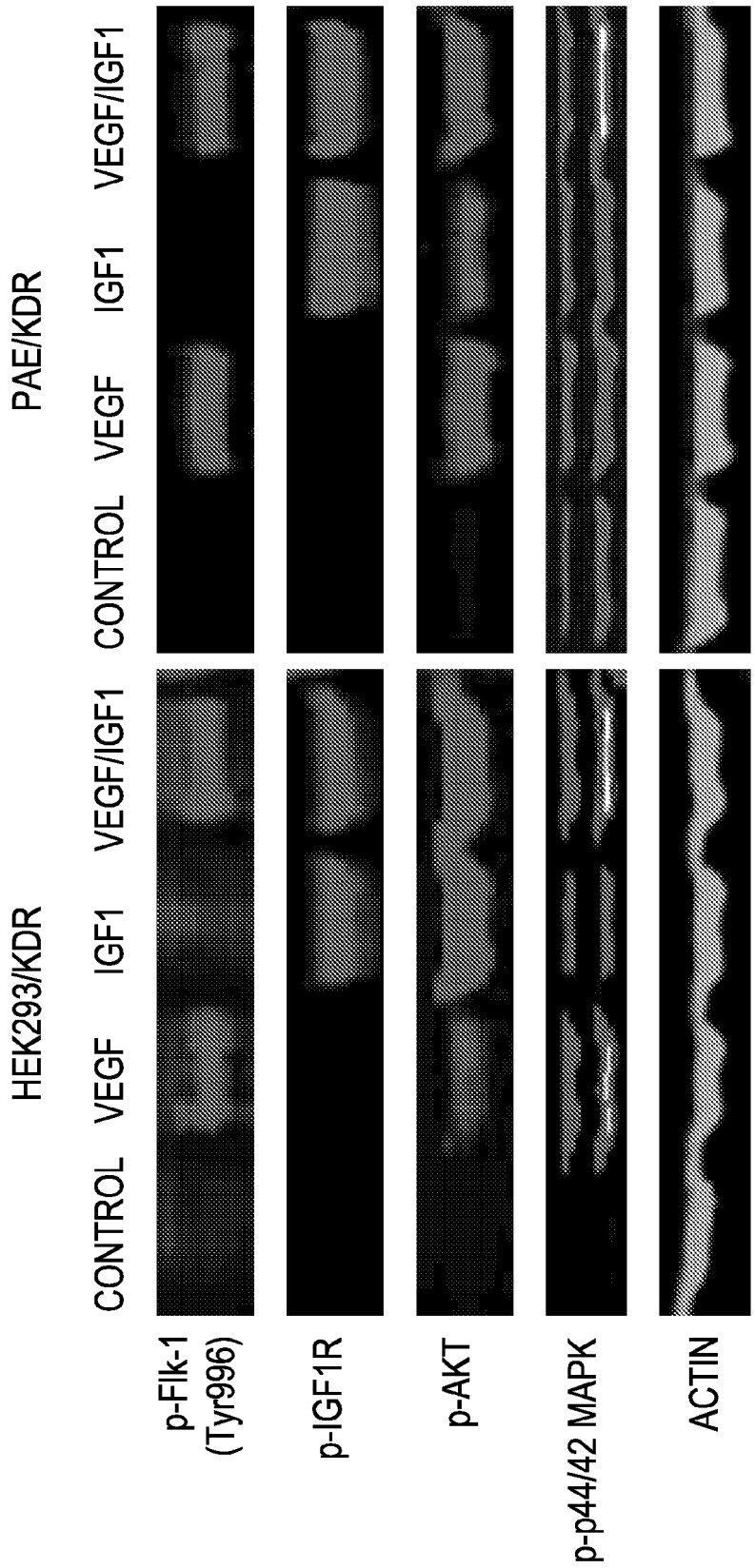
FIG. 15. HEK293/KDR and PAE/KDR cells express VEGFR2 and IGF-IR and both receptors are activated in the presence of their cognate ligands. HEK293 and PAE cells transfected with KDR (VEGFR2) were stimulated with VEGF, IGF1, or both factors (VEGF/IGF1). Western blots of the cell lysates were probed for phosphorylated VEGFR (p-Flk-1/Tyr996), phosphorylated IGF-IR, phosphorylated Akt, phosphorylated MAPK, or total actin.

Example 8. Activation and Signaling Activity of Multivalent Fibronectin Based Proteins in Cell-Based Assays Select V/I [10]Fn3-based binders were screened for the ability to directly interfere with ligand-stimulated VEGFR2 and IGF-IR activation and downstream MAP kinase signaling. HEK/293 cells and Porcine aortic endothelial (PAE) cells were transfected with VEGFR2. Stimulation by VEGF induces phosphorylation of VEGFR and downstream signaling in both cell types. Stimulation by IGF1 induces phosphorylation of IGF-IR and downstream signaling in both cell types, see FIG. 15. Further details on the PAE and HEK/293 assays are discussed in the materials and methods section below.

Figure 16:
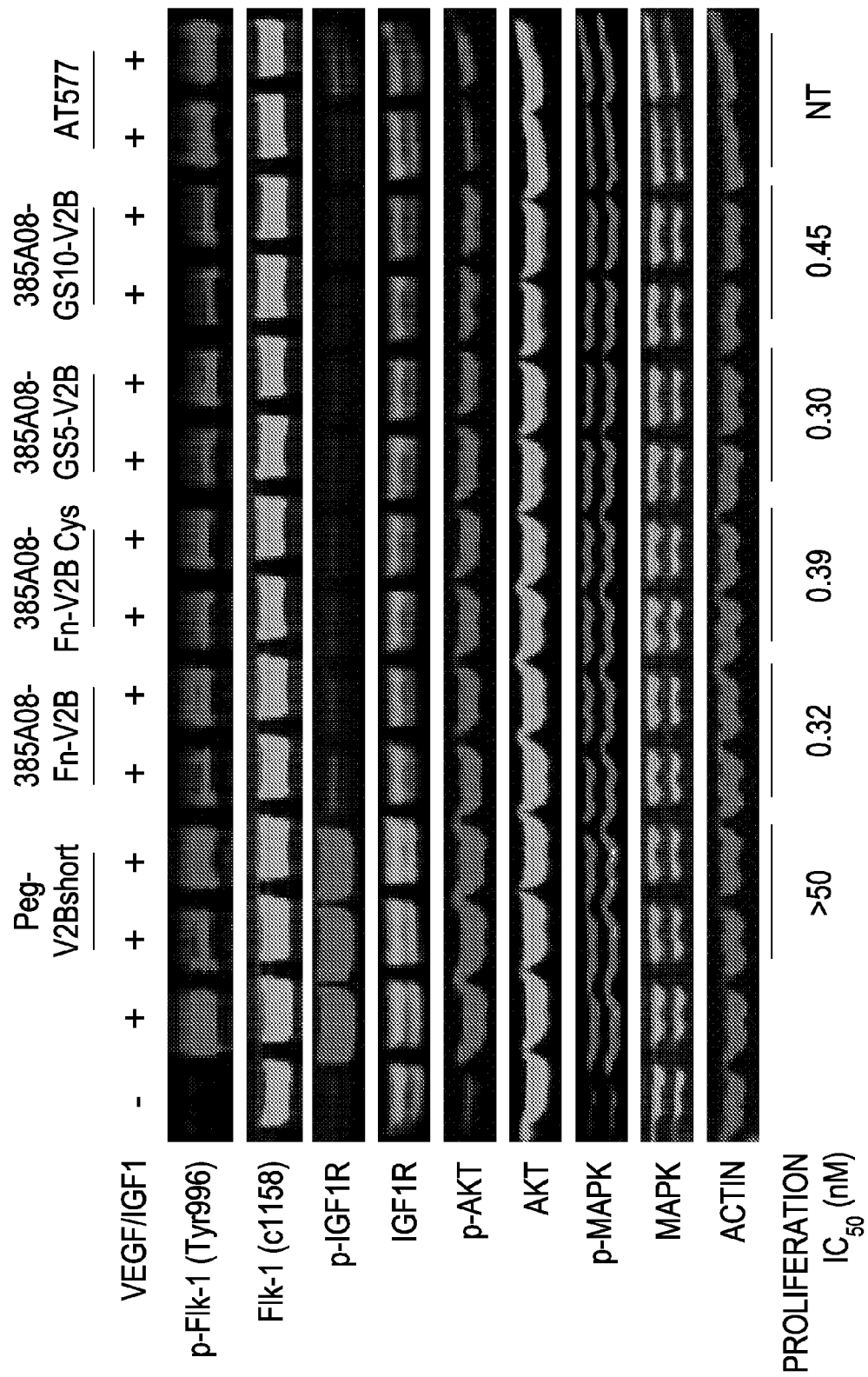
FIG. 16. Fibronectin based scaffold multimers block VEGFR2 and IGF-IR ligand induced phosphorylation and inhibit proliferation of HEK293/KDR cells. Cells were treated with VEGF and IGF1 ("-" indicates non-stimulated control) and fibronectin scaffold domain proteins as described in Example 8. Western blots of cell lysates were probed for phosphorylated VEGFR (p-Flk-1/Tyr996), total VEGFR (Flk-1), phosphorylated IGF-IR, total IGF-IR, phosphorylated Akt, total Akt, phosphorylated MAPK, total MAPK, or total actin. Cell proliferation was evaluated by [$^3$H]-thymidine incorporation after exposure to the various constructs and the results reported as IC$_{50}$. As shown: 'GS5' (SEQ ID NO: 21) and 'GS10' (SEQ ID NO: 22).

FIG. 16 depicts the effect of various multivalent proteins on HEK/293 cells. All of the multivalent proteins comprising an IGF-IR binding fibronectin scaffold domain decreased levels of phosphorylated IGF-IR to similar levels as compared to a single IGF-IR binding fibronectin scaffold domain protein (AT577). All of the multivalent proteins comprising a VEGFR2 binding fibronectin scaffold domain decreased levels of phosphorylated VEGFR to similar levels as compared to a single VEGFR2 binding fibronectin scaffold domain protein (Peg-V2Bshort). Cell proliferation was evaluated by [$^3$H]-thymidine incorporation after exposure to the various constructs.

Figure 17:
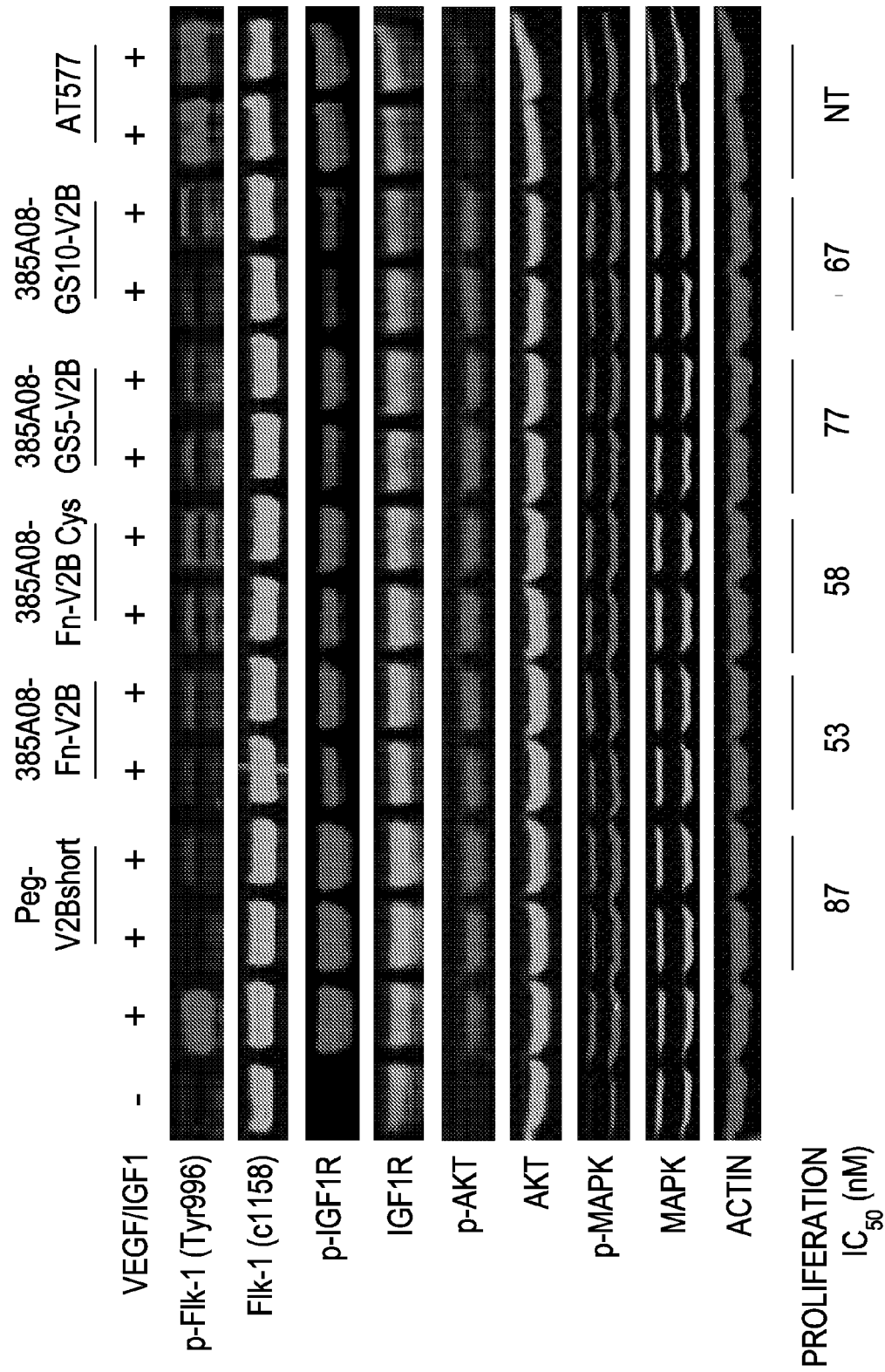
FIG. 17. Fibronectin based scaffold multimers block VEGFR2 and IGF-IR ligand induced phosphorylation and inhibit proliferation of HEK293/KDR cells. Cells were treated with VEGF and IGF1 and fibronectin scaffold domain proteins as described in Example 8. Western blots of cell lysates were probed for phosphorylated VEGFR (p-Flk-1/Tyr996), total VEGFR (Flk-1), phosphorylated IGF-IR, total IGF-IR, phosphorylated Akt, total Akt, phosphorylated MAPK, total MAPK, or total actin. Cell proliferation was evaluated by [$^3$H]-thymidine incorporation after exposure to the various constructs and the results reported as IC$_{50}$. As shown: 'GS5' (SEQ ID NO: 21) and 'GS10' (SEQ ID NO: 22).

FIG. 17 depicts the effect of various multivalent proteins on PAE cells. All of the multivalent proteins comprising an IGF-IR binding fibronectin scaffold domain decreased levels of phosphorylated IGF-IR to similar levels as compared to a single IGF-IR binding fibronectin scaffold domain protein (AT577). All of the multivalent proteins comprising a VEGFR2 binding fibronectin scaffold domain decreased levels of phosphorylated VEGFR to similar levels as compared to a single VEGFR2 binding fibronectin scaffold domain protein (Peg-V2Bshort). Cell proliferation was evaluated by [$^3$H]-thymidine incorporation after exposure to the various constructs.

These results demonstrate that the exemplary polypeptide linkers are able to link fibronectin scaffold domains in an orientation whereby their binding to ligand, and therefore their ability to inhibit receptor signaling, is retained.

Additional studies were conducted on specific varieties of the tandem construct 385A08-Fn-V2B-cys (SEQ ID NO: 9, with and without PEG; with and without a his-tag) in primary human microvascular endothelial cells from lung (HMVEC-L). Assays measuring the following were conducted in HMVEC-L: cell proliferation, inhibition of ligand-induced VEGFR-2 and IGF-1R activity (via Western blot analysis), the mobilization of intracellular calcium (Ca2$^+$ Flux) in endothelial cells, and the ability to inhibit formation of nascent capillary-like structures known as tubes. An additional study measuring the inhibition of ligand-induced VEGFR-2 and IGF-1R activity via Western blot analysis was also conducted in Rh41 cells. Each of these assays are described in further detail in the materials and methods section below.

The results from the cellular proliferation assay showed that specific varieties of the 385A08-Fn-V2B-cys constructs inhibit proliferation in HMVEC-L cells with an IC$_{50}$ ranging between 90 nM and 167 nM (see FIG. 18). In one example, a pegylated, non-his-tag version of this construct inhibited proliferation in HMVEC-L cells with an IC$_{50}$ of ~167 nM, whereas the mono-specific [10]Fn3-based VEGFR-2 binder (Peg-V2Bshort, SEQ ID NO: 28) had an IC$_{50}$ of ~47 nM.

Figure 19:
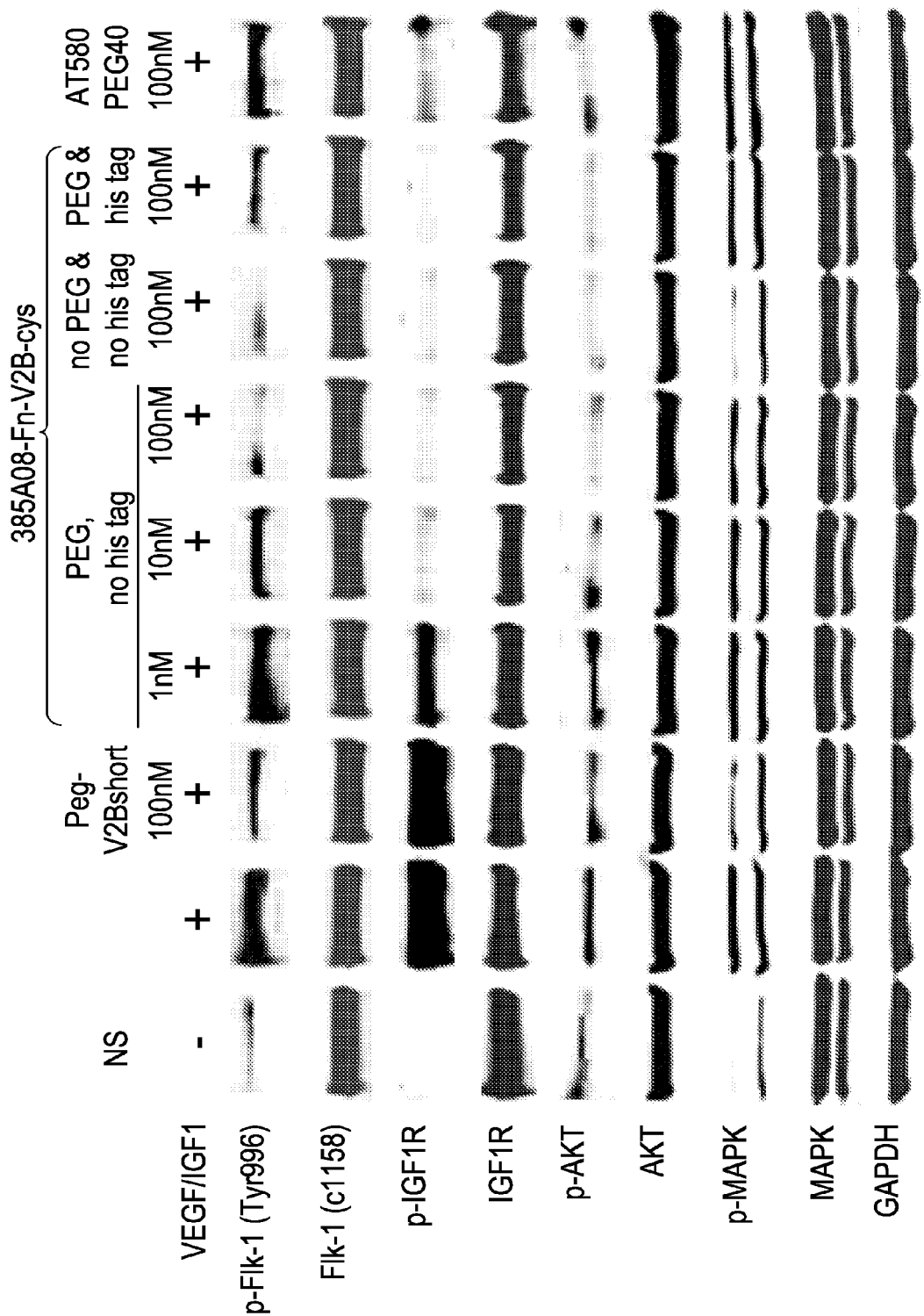
FIG. 19. Western blot analysis: HMVEC-L cells were exposed to increasing concentrations of various constructs for 1 hr followed by activation with VEGF/IGF-1 ligands (both 50 ng/ml final concentration) for 10 min at 37° C. prior to lysis. Inhibition of pIGF-1R, pAkt, and pMAPK activities were measured by comparing the ratio of phospho-signals in untreated versus treated samples, and after normalization to GAPDH which is used as a loading control.

In order to assess the ability of the 385A08-Fn-V2B-cys constructs to inhibit IGF-1R and VEGFR-2, Western blot analysis was done to measure the activity of ligand-induced VEGFR-2 and IGF-1R activity in HMVEC-L cells by autophosphorylation in the presence or absence of the test compounds. Appropriate controls included the mono-specific [10]Fn3-based VEGFR-2 binder (Peg-V2Bshort, SEQ ID NO: 28), and the mono-specific [10]Fn3-based IGF-IR binder (AT580-PEG40, SEQ ID NO: 27). The constructs generally inhibited pVEGFR-2 (pVEGFR-2 is phospho-VEGFR-2; also known as p-Flk-1), pIGF-1R, and pAKT activity (see FIG. 19). A pegylated, non-his-tag version of the 385A08-Fn-V2B-cys construct demonstrated inhibition of pVEGFR-2 activity in a dose response starting at 10 nM, with near complete inhibition being achieved at 100 nM. This same compound also potently inhibited pIGF-1R activity at between 1 nM and 10 nM as compared to AT580-PEG40 where the IC$_{50}$ for inhibition was 100 nM.

Figure 20:
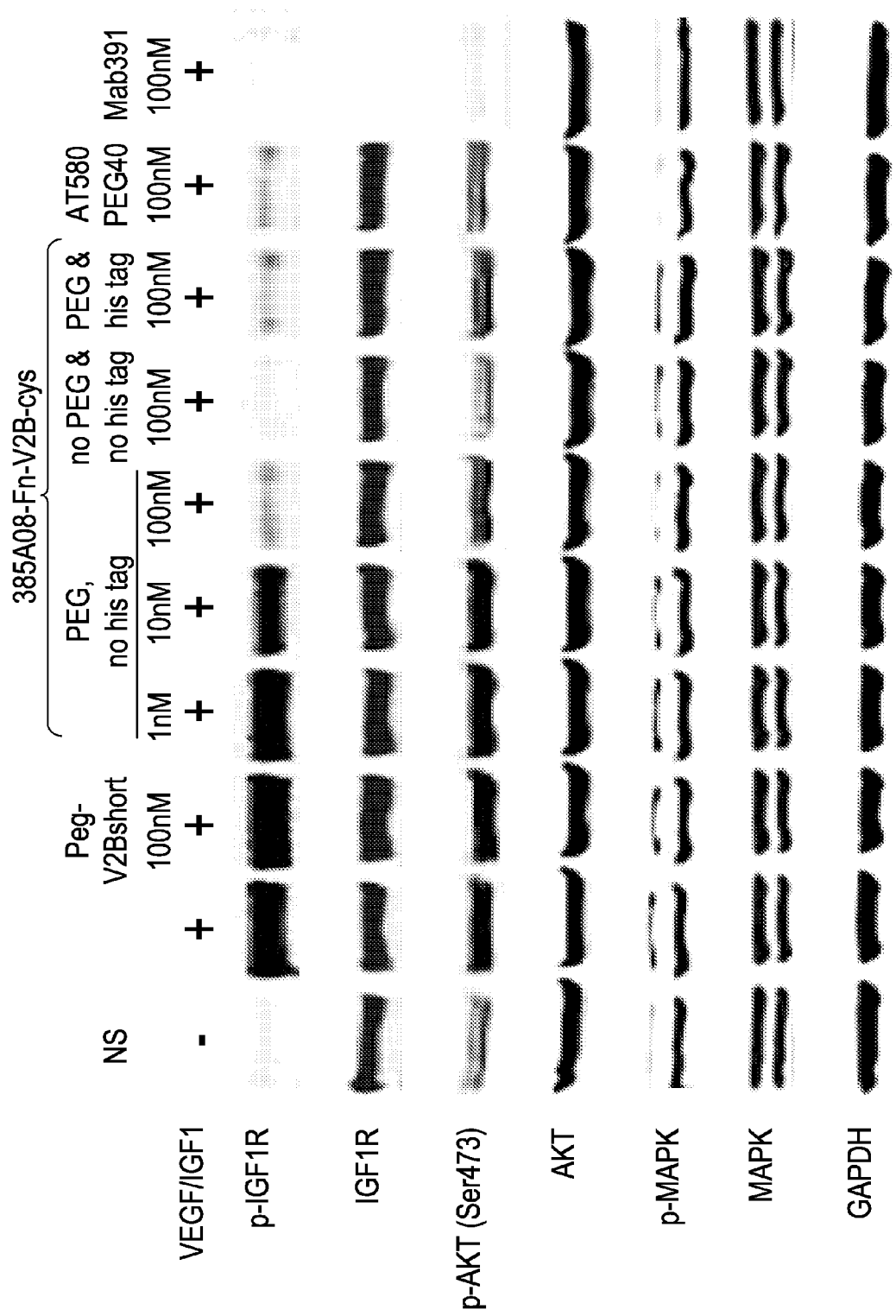
FIG. 20. Western blot analysis: Rh41 cells were exposed to increasing concentrations of compounds for 1 hr followed by activation with IGF-1 ligand (50 ng/ml) for 10 min at 37° C. prior to lyses. pIGF-1R and pAkt activities were measured by comparing the ratio of phospho-signals in untreated versus treated samples, and after normalization to GAPDH which is used as a loading control.

In order to assess the ability of the specific varieties of the 385A08-Fn-V2B-cys constructs to inhibit IGF-1R in an IGF-1R-driven tumor cell line, Western blot analysis was carried out to measure the activity of ligand-induced IGF-1R activity in Rh41 cells by autophosphorylation in the presence or absence of the test compounds. Inhibition of pIGF-1R activity was generally observed for all of the 385A08-Fn-V2B-cys constructs at the 100 nM dose. Inhibition of pAKT was observed at varying levels for all of the 385A08-Fn-V2B-cys constructs tested. In one example, the pegylated, non his-tag version of the 385A08-Fn-V2B-cys construct demonstrated inhibition of pIGF-1R activity starting at the dose response in the ~1-10 nM range and inhibition was nearly complete at 100 nM. These data are summarized in FIG. 20.

Because VEGF stimulates the mobilization of intracellular calcium in endothelial cells (as described in Ku, D. D., et al., *Vascular endothelial growth factor induces EDRF-dependent relaxation in coronary arteries*. Am J Physiol, 1993. 265(2 Pt 2): p. H586-92), the ability to inhibit calcium release (Ca$^2$) is another measure of cell-based signaling for a VEGFR-2 inhibitor. In an assay measuring calcium release in HMVEC-L cells, the specific varieties of 385A08-Fn-V2B-cys constructs demonstrated an inhibition of Ca$^{2+}$ release with an IC$_{50}$ of 4-10 nM. A similar level of inhibition was demonstrated for a mono-specific [10]Fn3-based VEGFR-2 binder (Peg-V2Bshort, SEQ ID NO: 28). The results of this study are summarized in FIG. 21.

Example 9. Tumor Xenograft Efficacy Studies on Multivalent Fibronectin Based Proteins A pegylated, his-tagged version of the construct 385A08-Fn-V2B-Cys was evaluated in multiple tumor studies using an RH-41 human rhabdomyosarcoma model, an A549 human lung model, a GEO colon tumor xenograft model, and an A673 Ewing Sarcoma xenograft tumor model. RH-41 and A673 were selected for in vivo testing with 385A08-Fn-V2B-Cys as both models had previously shown sensitivity to IGF-1R inhibition. A549 and GEO, which are not as sensitive to IGF1R inhibition, were selected to compare the potency of VEGFR2 inhibition by the multivalent constructs as compared to the monomeric VEGFR2 inhibitor, PEG-V2B-short (SEQ ID NO: 28 with PEG attached at the single cysteine residue). These models are described in more detail in the materials and methods section below.

Figures 22A, 22B:
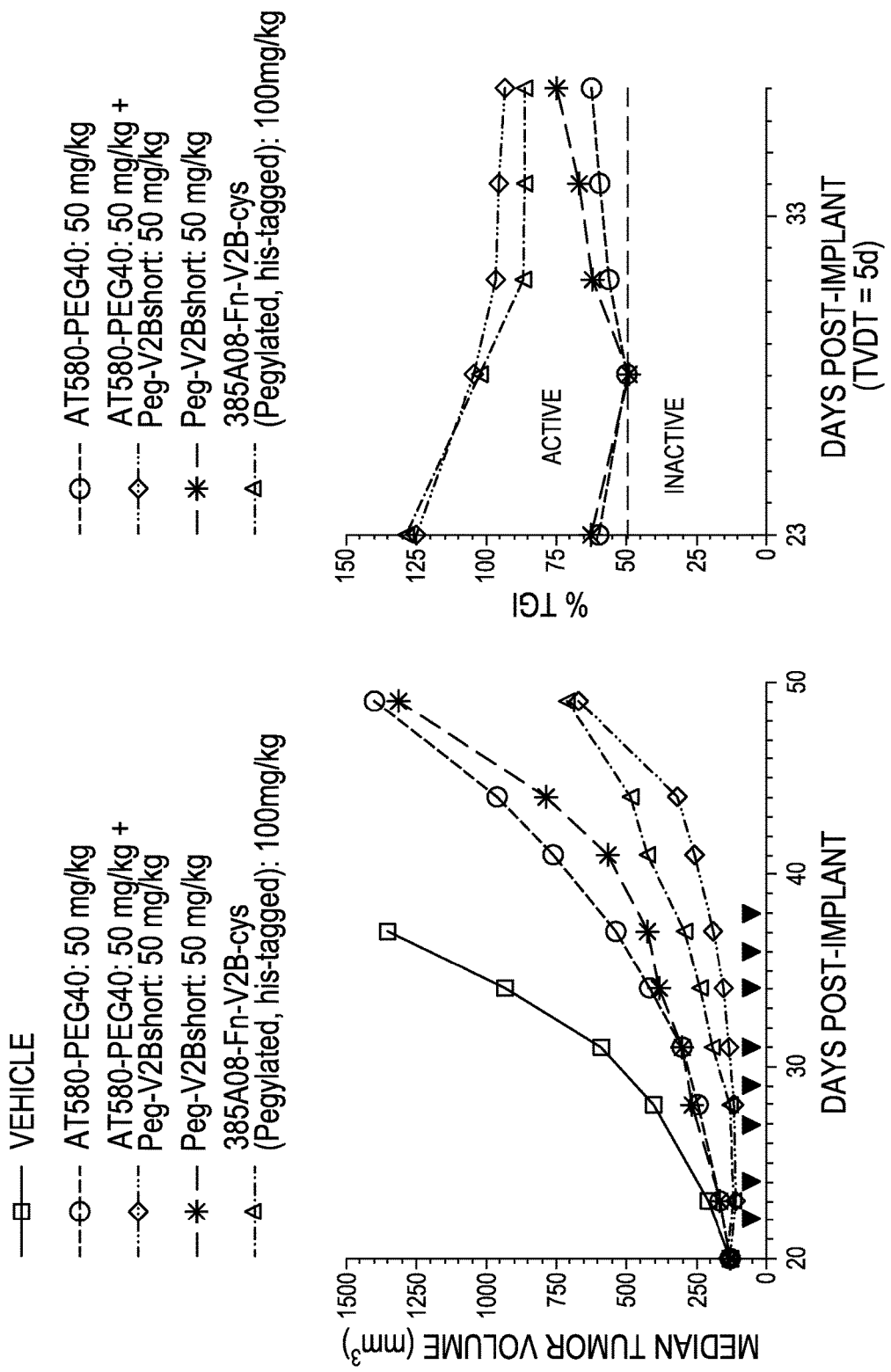
FIGS. 22A and 22B. Antitumor activity of pegylated his-tagged 385A08-Fn-V2B-cys in the RH-41 tumor xenograft model at a single dose level.

The RH-41 tumor xenograft model has been demonstrated to be sensitive to IGF-IR inhibition. Pegylated, his-tagged 385A08-Fn-V2B-Cys was administered on a 3×wk schedule using a single dose level of 100 mg/kg. As illustrated in FIG. 22, segment A, pegylated, his-tagged 385A08-Fn-V2B-Cys was effective in inducing tumor growth delay when dosed for three weeks using this regimen. When compared to a combination of a mono-specific [10]Fn3-based VEGFR-2 binder (Peg-V2Bshort, SEQ ID NO: 28) and a mono-specific [10]Fn3-based IGF-IR binder (AT580-PEG40, SEQ ID NO: 27) that should yield a comparable stoichiometry of target binding for IGFR-1 and VEGFR-2, pegylated, his-tagged 385A08-Fn-V2B-Cys resulted in similar antitumor activity. Furthermore, the antitumor activity achieved with the multivalent construct was superior to that observed when these agents were dosed individually based on percent tumor growth inhibition (% TGI). No overt toxicity was observed for any of these agents as defined by morbidity, behavioral changes or significant weight loss (e.g., >5%). As summarized in FIG. 22, Segment B, all of these agents were effective in yielding >50% TGI, however both the combination of AT580-PEG40, Peg-V2Bshort, as well as pegylated, his-tagged 385A08-Fn-V2B-Cys alone, resulted in an increased % TGI when compared to each agent alone.

The 385A08-Fn-V2B-cys (with Peg) construct binds to human IGF1R with a much higher affinity than it binds to mouse IGF1R. In particular, 385A08-Fn-V2B-cys (with Peg) binds to human IGF1R with a Kd of 277 pM, to monkey IGF1R with a Kd of 213 pM, to rat IGF1R with a Kd of 92,000 pM and to mouse IGF1R with a Kd of 86,000 pM. The tumor xenograft models used in this study involve human tumors displaying human IGF1R but also involve mouse endothelial cells expressing mouse IGF1R. Since the binding affinity for 385A08-Fn-V2B-cys (with Peg) to mouse IGF1R is so much lower than that for human IGF1R, the effects seen in this model may underestimate the effects of 385A08-Fn-V2B-cys (with Peg) on tumor inhibition. In particular, tumor growth inhibition could be more significant if the binding affinity for the IGF1R expressed on the endothelial cells was higher.

Figures 23A, 23B:
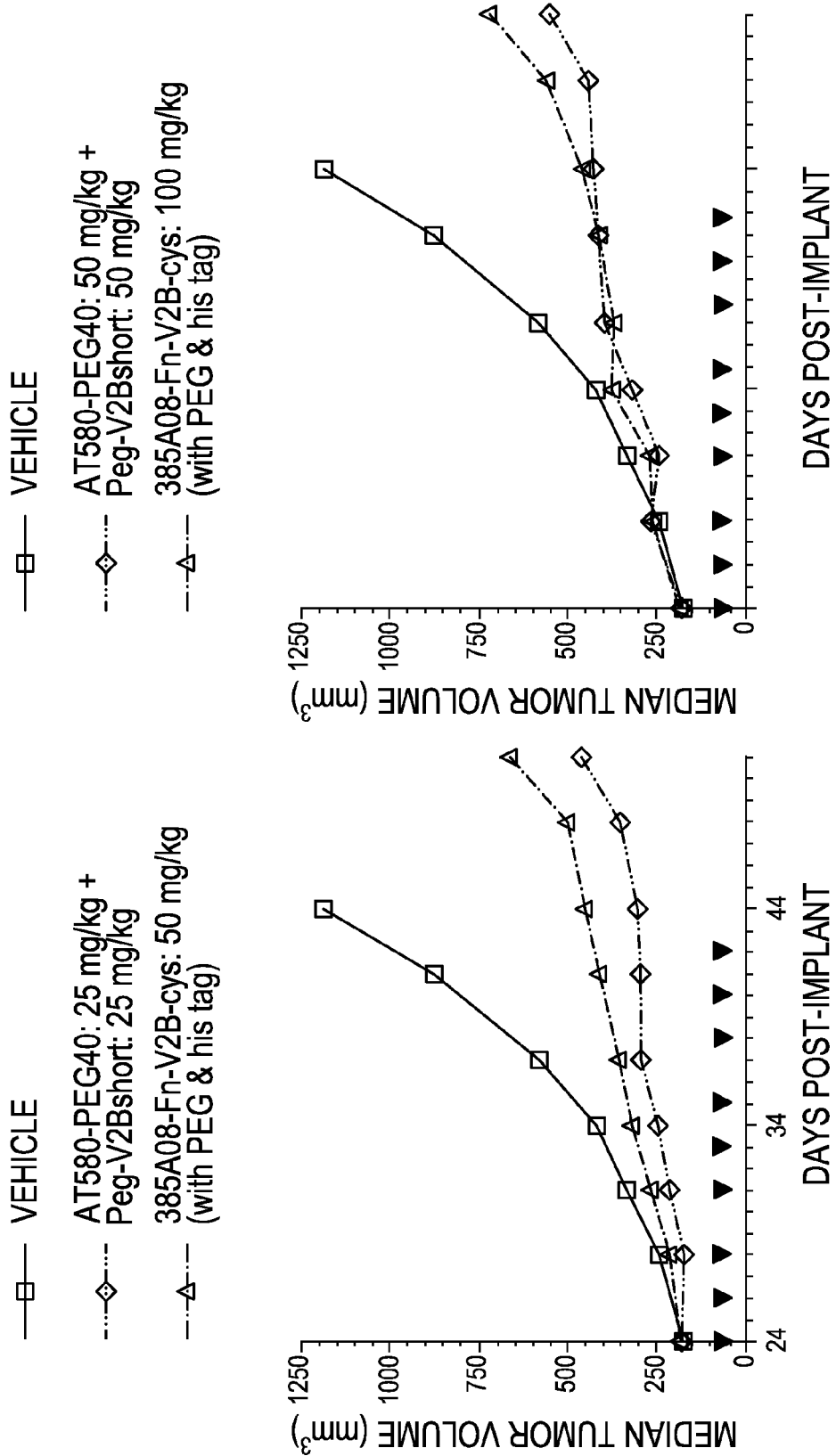

In a second study using the RH-41 tumor xenograft model, pegylated, his-tagged 385A08-Fn-V2B-Cys was evaluated over several dose levels including 50 mg/kg, 100 mg/kg and 200 mg/kg. These levels were also compared to the combined equivalent API (active pharmaceutical ingredient) dose level of each of the individually targeted mono-specific binders, e.g., a mono-specific [10]Fn3-based VEGFR-2 binder (Peg-V2Bshort, SEQ ID NO: 28) and a mono-specific [10]Fn3-based IGF-IR binder (AT580-PEG40, SEQ ID NO: 27). The results of this study are illustrated in FIG. 23 where, for the purpose of clarity, each dose level of pegylated, his-tagged 385A08-Fn-V2B-Cys is shown individually in comparison to the corresponding combination dose levels of the individual AT580-PEG40 and Peg-V2Bshort. The combination of AT580-PEG40 and Peg-V2Bshort compared favorably with pegylated, his-tagged 385A08-Fn-V2B-Cys, resulting in similar % TGI. Furthermore, all dose levels of pegylated, his-tagged 385A08-Fn-V2B-Cys resulted in similar antitumor activity (as illustrated in FIG. 23, Segment D), ranging from 75-83% TGI. As a result, further titration at lower dose levels of pegylated, his-tagged 385A08-Fn-V2B-Cys will be required in order to generate a definitive antitumor dose response curve and to determine the minimum efficacious dose level in this tumor model.

Figures 24A, 24B:
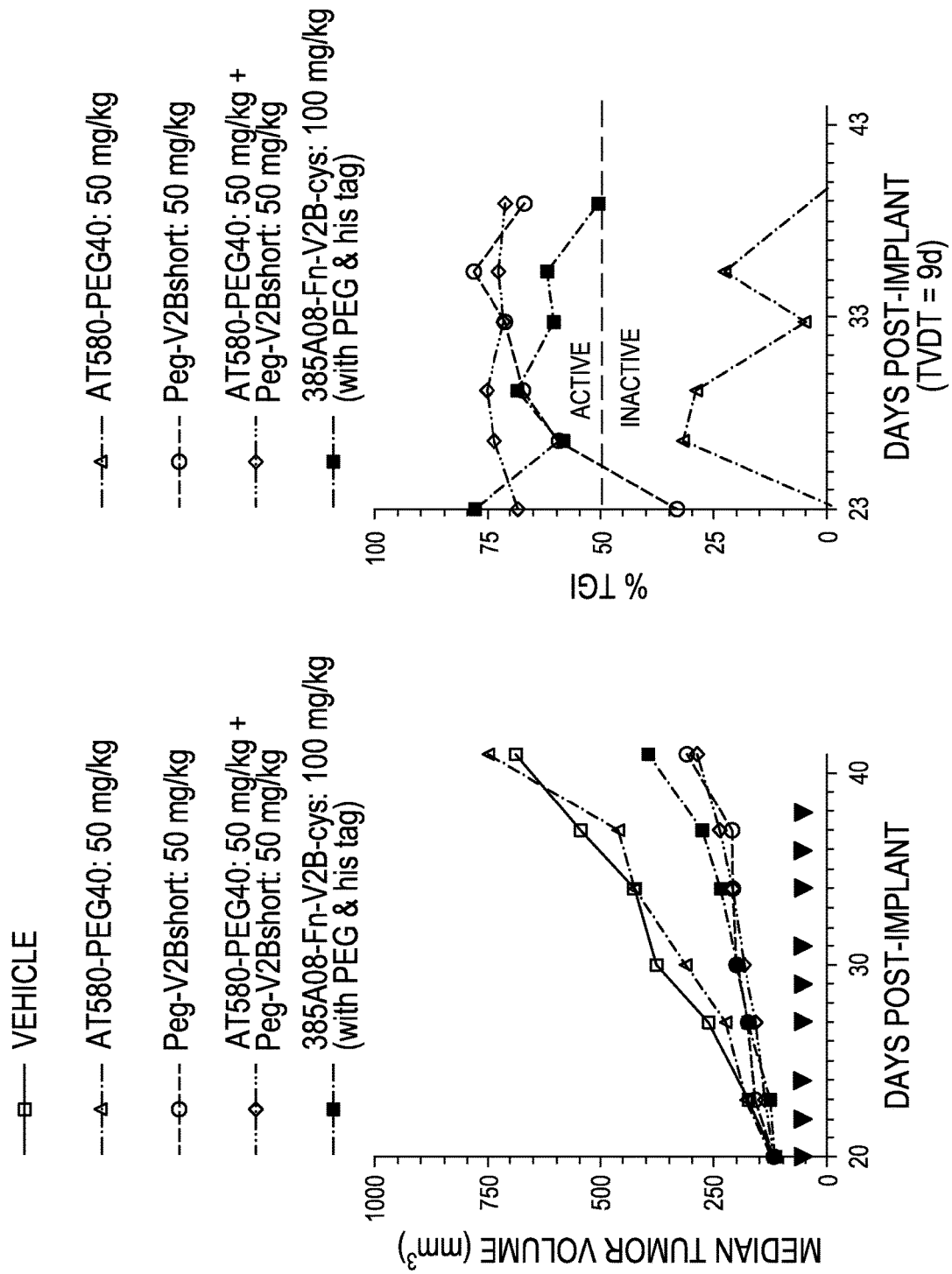

The antitumor activity of pegylated, his-tagged 385A08-Fn-V2B-Cys was also evaluated in the A549 tumor model in comparison to a mono-specific [10]Fn3-based VEGFR-2 binder (Peg-V2Bshort, SEQ ID NO: 28) and a mono-specific [10]Fn3-based IGF-IR binder (AT580-PEG40, SEQ ID NO: 27), as well as a combination treatment with these two mono-specific binders (see FIG. 24). Given the lack of an antitumor response to AT580-PEG40 at the two dose levels tested (FIG. 26, Segments A & C) and based on less than 50% TGI (FIG. 26, Segments B & D), this model appears to be insensitive to inhibition of IGF-1R. Further, the combination of AT580-PEG40 and Peg-V2Bshort, did not result in enhanced antitumor activity when compared to dosing of Peg-V2Bshort alone, which was active at both dose levels tested. The observation that the level of tumor growth inhibition achieved with pegylated, his-tagged 385A08-Fn-V2B-Cys was comparable to that seen with Peg-V2Bshort dosed alone suggests that the antitumor activity observed in this model appears to reside with the anti-VEGFR-2 activity of pegylated, his-tagged 385A08-Fn-V2B-Cys and Peg-V2Bshort.

Figures 25A, 25B:
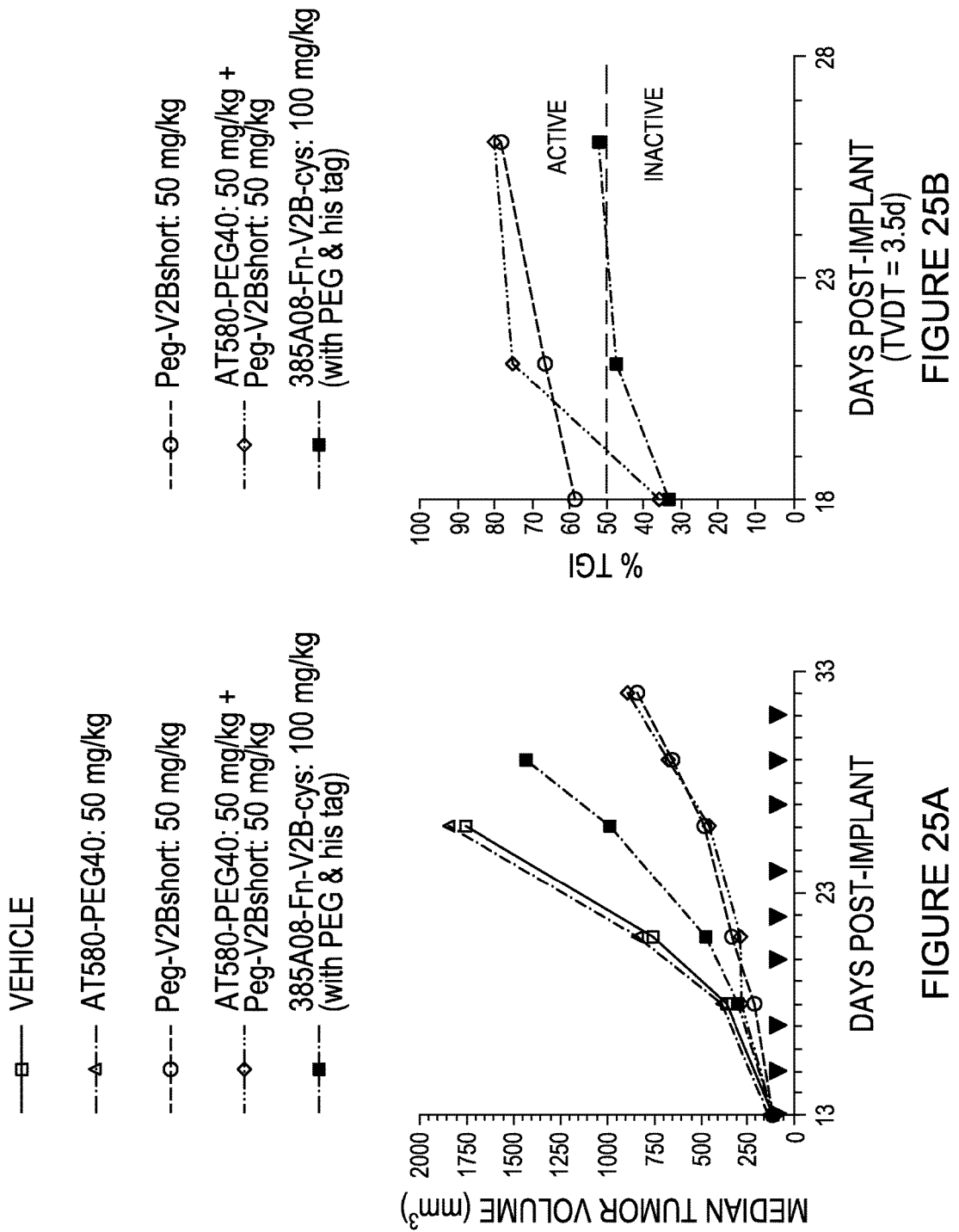

Comparable results were also obtained when these agents were evaluated in the GEO human colon xenograft model, which also appears to be insensitive to inhibition of IGF-1R (FIG. 25). In this model, pegylated, his-tagged 385A08-Fn-V2B-Cys was inactive at 100 mg/kg (FIG. 27, Segments A and B) and the mono-specific [10]Fn3-based IGF-IR binder (AT580-PEG40, SEQ ID NO: 27) was inactive at both dose levels tested (FIG. 25, Segments A, B, C, & D). At the higher dose level of 200 mg/kg, pegylated, his-tagged 385A08-Fn-V2B-Cys was active and demonstrated antitumor activity based on >50% TGI (FIG. 25, Segments C and D). Similar to the observations made using the A549 model, the mono-specific [10]Fn3-based VEGFR-2 binder (Peg-V2Bshort, SEQ ID NO: 28) was active against the GEO model, suggesting that the antitumor activity observed with pegylated, his-tagged 385A08-Fn-V2B-Cys in this model may be solely dependent on the anti-VEGFR-2 component and that the GEO model is insensitive to IGF-IR inhibition. The increased antitumor activity observed with Peg-V2Bshort (as compared to pegylated, his-tagged 385A08-Fn-V2B-Cys) in this model (illustrated in FIG. 25, Segments A and B) may potentially be a reflection of the higher binding affinity for VEGFR-2 by the monomeric Peg-V2Bshort as compared to the VEGFR2 binding subunit included in the pegylated, his-tagged 385A08-Fn-V2B-Cys construct (see Example 6 above).

Figure 26:
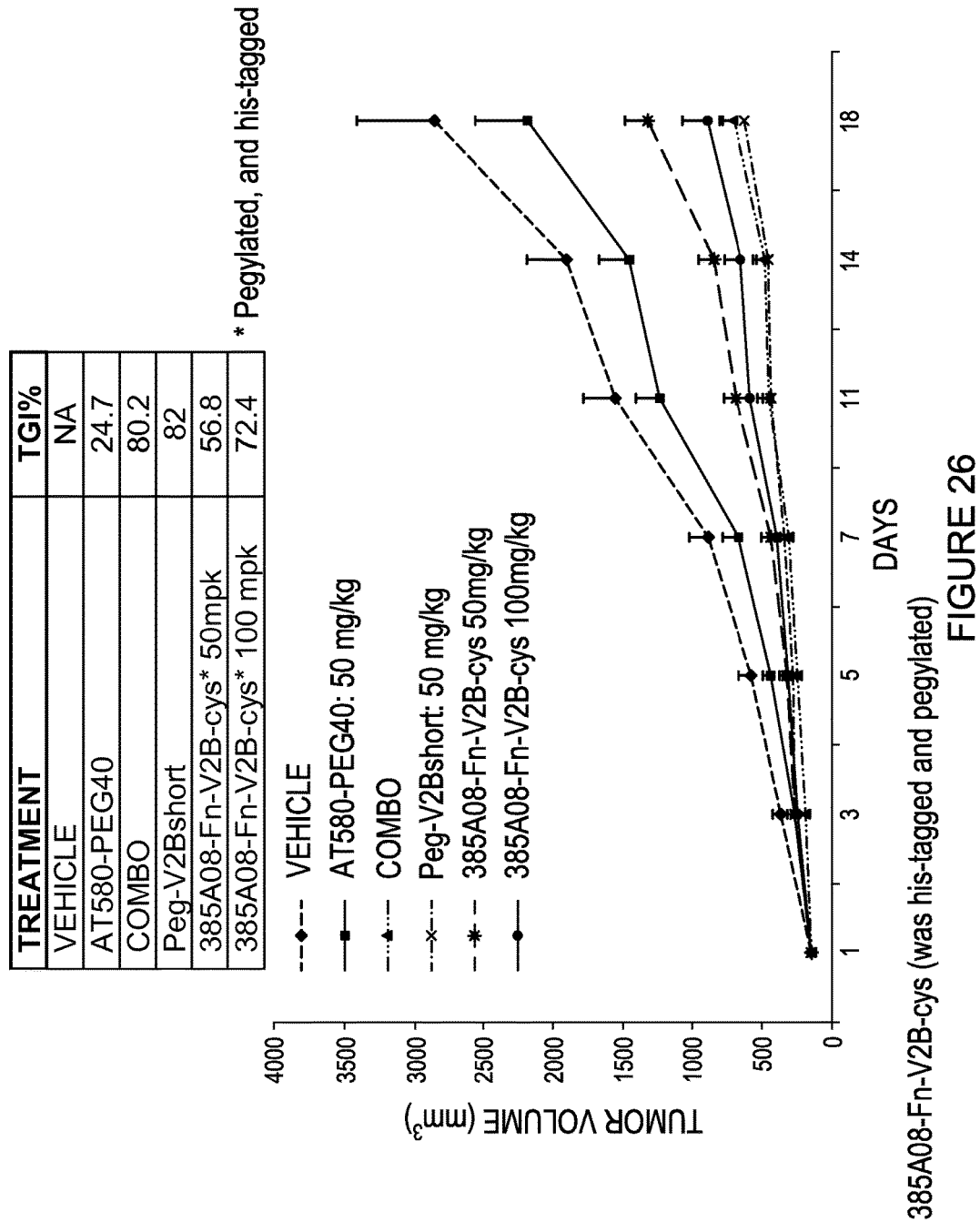
FIG. 26. pegylated, his-tagged 385A08-Fn-V2B-cys mediated Tumor Growth Inhibition in A673 Ewing Sarcoma Xenograft Tumors is comparable to that of the mononectin PEG-V2B-short, a pegylated anti-VEGFR-2 adnectin.

In the A673 Ewing Sarcoma xenograft model, pegylated, his-tagged 385A08-Fn-V2B-Cys showed antitumor activity that was slightly weaker than mono-specific [10]Fn3-based VEGFR-2 binder (Peg-V2Bshort, SEQ ID NO: 28) (TGI=72.4% vs 82%, respectively), as shown in FIG. 26. This is likely a consequence of the lower affinity (approximately 4-5 fold lower) of the anti-VEGFR2 domain of pegylated, his-tagged 385A08-Fn-V2B-Cys as compared to Peg-V2Bshort (see Example 6 above). On the other hand, the antitumor activity in the combo group was comparable to that of Peg-V2Bshort (TGI=80.2 vs 82%, respectively), suggesting that the A673 Ewing Sarcoma xenograft model is insensitive to IGF-IR inhibition because the IGF-IR inhibition contribution to the overall antitumor activity was rather marginal, as evidenced by the response to the mono-specific [10]Fn3-based IGF-IR binder (AT580-PEG40, SEQ ID NO: 27) administration (TGI=24.7%). Antitumor activities from pegylated, his-tagged 385A08-Fn-V2B-Cys at 100 mg/kg, as well as Peg-V2Bshort and the combination of Peg-V2Bshort+AT580-PEG40 were significantly different from vehicle. Additionally, there appeared to be a dose response between the two different doses tested for pegylated, his-tagged 385A08-Fn-V2B-Cys (50 vs 100 mg/kg) at the end of study (Day 18, TGI=56.8% vs 72.4%, respectively), but without reaching statistically significant differences between the two (FIG. 26).

Pegylated, his-tagged 385A08-Fn-V2B-Cys dose response was also evaluated in the A673 Ewing Sarcoma model. The antitumor activity of doses between 20 mg/kg and 200 mg/kg were compared; this dose range was selected to maximize the likelihood to differentiate minimum vs. maximum efficacious doses. The different doses of pegylated, his-tagged 385A08-Fn-V2B-Cys did not display a dose-dependent antitumor response. In fact, doses of 20, 60, and 100 mg/kg were not distinguishable from each other (TGI=58.3, 67.1, 63.1, respectively) and 200 mg/kg had the maximum inhibitory activity (TGI=80.5%).

Example 10: PK/PD Studies on Multivalent Fibronectin Based Proteins

Single-Dose Pharmacokinetic Study with his-Tagged 385A08-Fn-V2B-Cys in Mice.

FIG. 27 summarizes the pharmacokinetic parameters of his-tagged 385A08-Fn-V2B-Cys in mice. Following a single IV dose of 5 or 50 mg/kg, his-tagged 385A08-Fn-V2B-Cys serum concentrations exhibited a slightly bi-exponential decline. The CLTp of his-tagged 385A08-Fn-V2B-Cys was 0.11-0.12 mL/min/kg. The Vss (0.10-0.12 L/kg) was greater than plasma volume but lower than the volume of extracellular fluid (0.2 L/kg). The MRT and T½ of his-tagged 385A08-Fn-V2B-Cys were 15.2-16.8 and 13.0-21.4 h, respectively.

After a single IP dose of 5 or 50 mg/kg, his-tagged 385A08-Fn-V2B-Cys was rapidly absorbed (Tmax=1.4-3.0 h), with a serum concentration-time profile parallel to that after IV dosing. The absorption was nearly complete, with an absolute IP bioavailability of 83.1-105.8%. The average Cmax at 5 and 50 mg/kg was 1.5 and 14.4 µM, respectively.

Single-Dose Pharmacokinetic/Pharmacodynamic Study with his-Tagged 385A08-Fn-V2B-Cys in Nude Mice Bearing the Rh41 Tumor.

Figures 28A, 28B:
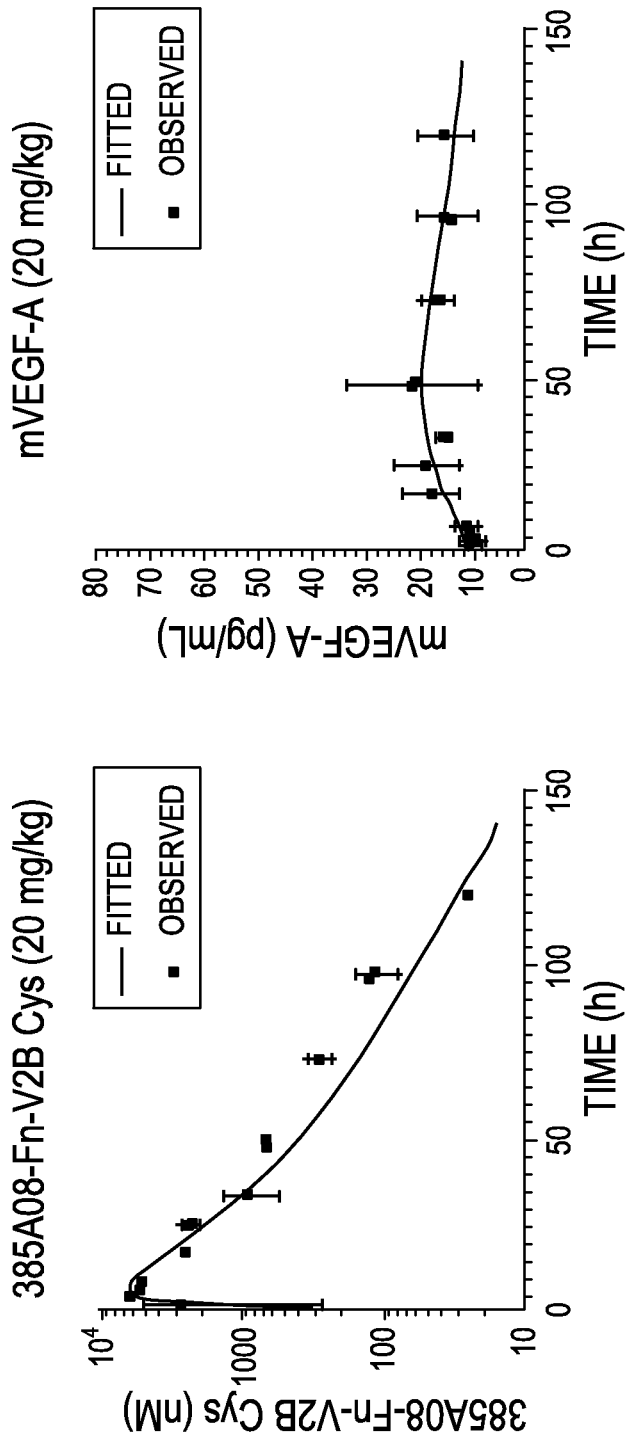

Following IP doses of 20 and 200 mg/kg of his-tagged 385A08-Fn-V2B-Cys to nude mice bearing the Rh41 tumor, the mVEGF-A levels showed dose- and time-dependent increases in plasma (FIG. 28). Using an indirect-response PD model, the plasma IC50 of his-tagged 385A08-Fn-V2B-Cys that inhibited the clearance of mVEGF-A from plasma by blocking its binding to VEGFR-2 was estimated to be 13.8 µM at 200 mg/kg. At 20 mg/kg, the dynamic range of mVEGF-A concentrations may be too low to yield meaningful estimates of PD parameters.

Single-Dose Pharmacokinetic/Pharmacodynamic Study with 385A08-Fn-V2B-Cys (Non-his Tagged) in Nude Mice Bearing the A673 Tumor.

Figures 29A, 29B:
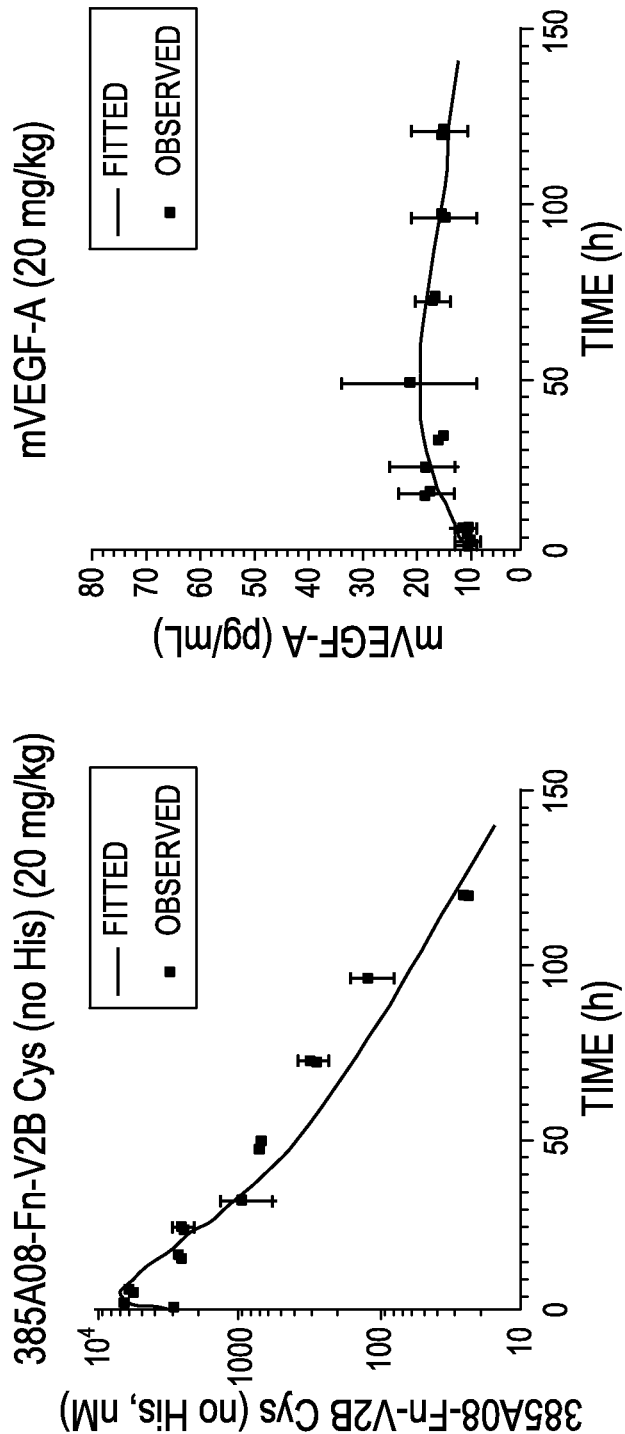
Figure 31B:
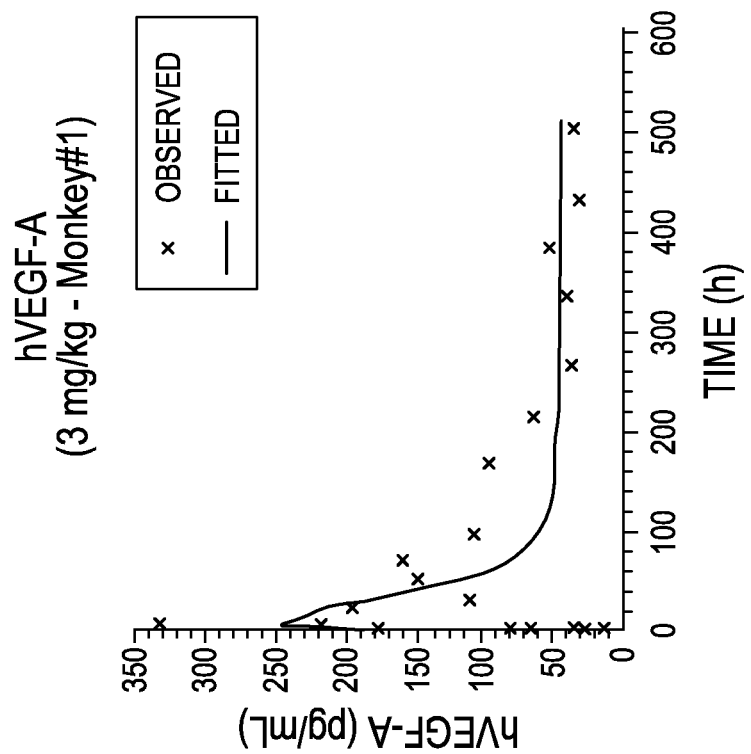
FIGS. 31A-31H. Fitted vs. observed plasma concentration-time profiles of 385A08-Fn-V2B-cys (with his) and hVEGF-A after IV administration of 3 and 30 mg/kg to monkeys.
Figure 31A:
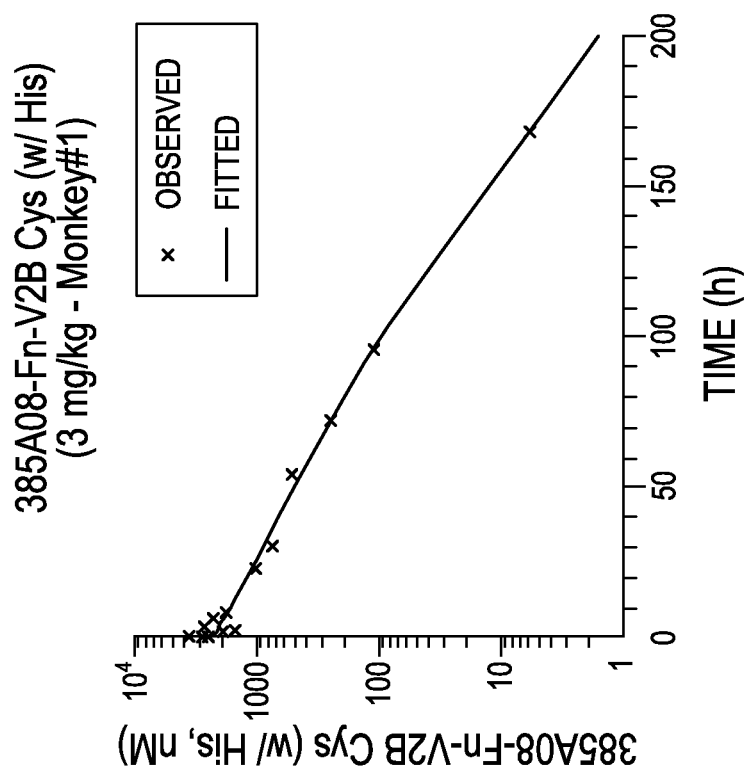
Figure 31D:
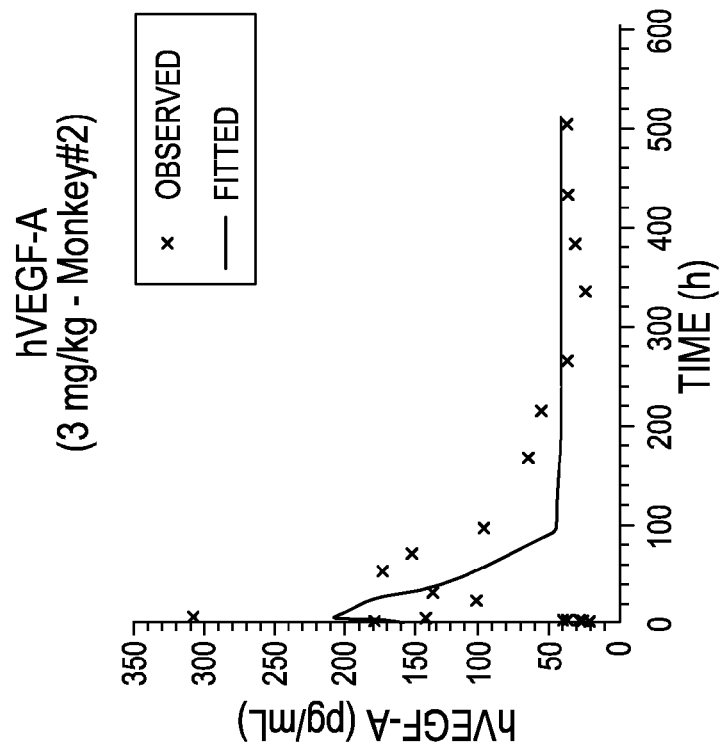
Figure 31C:
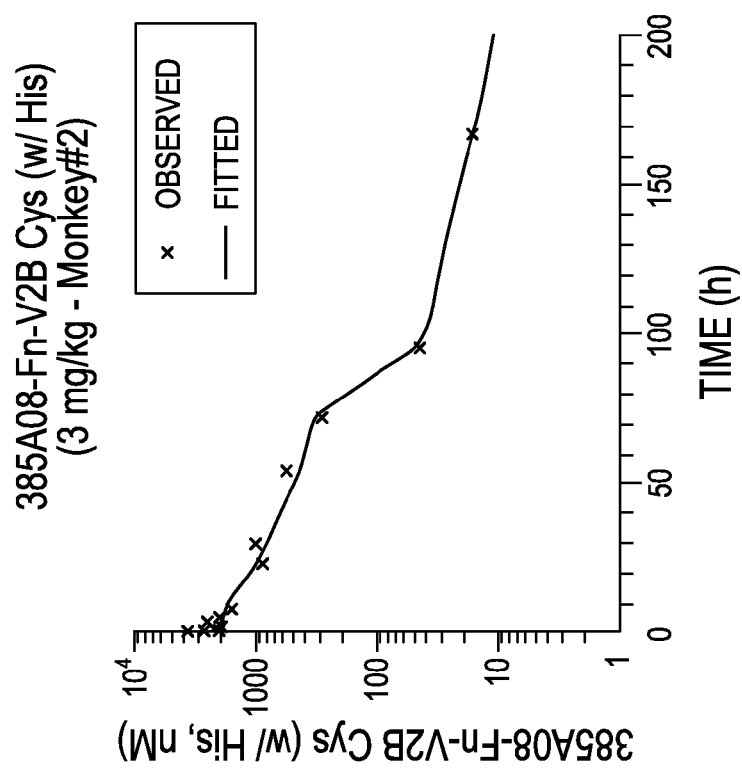
Figure 31F:
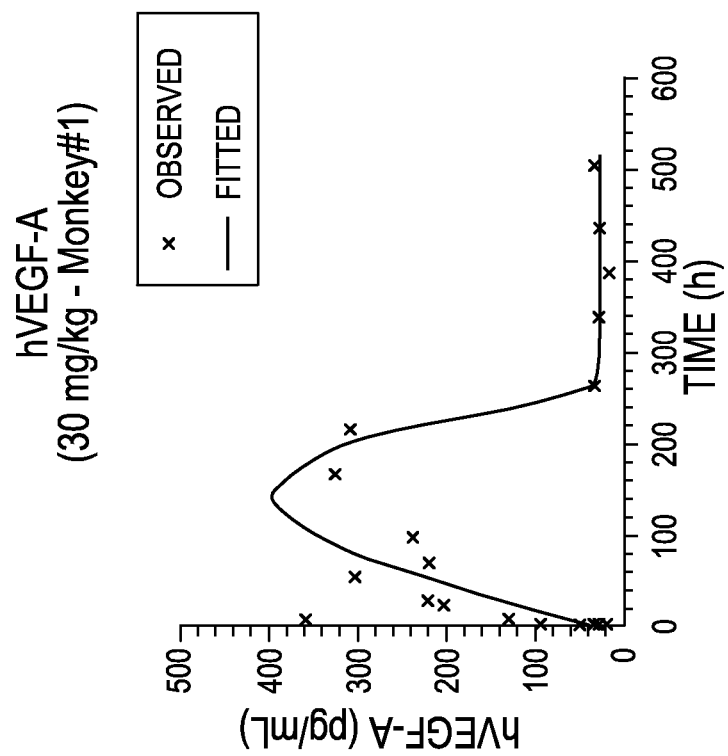
Figure 31E:
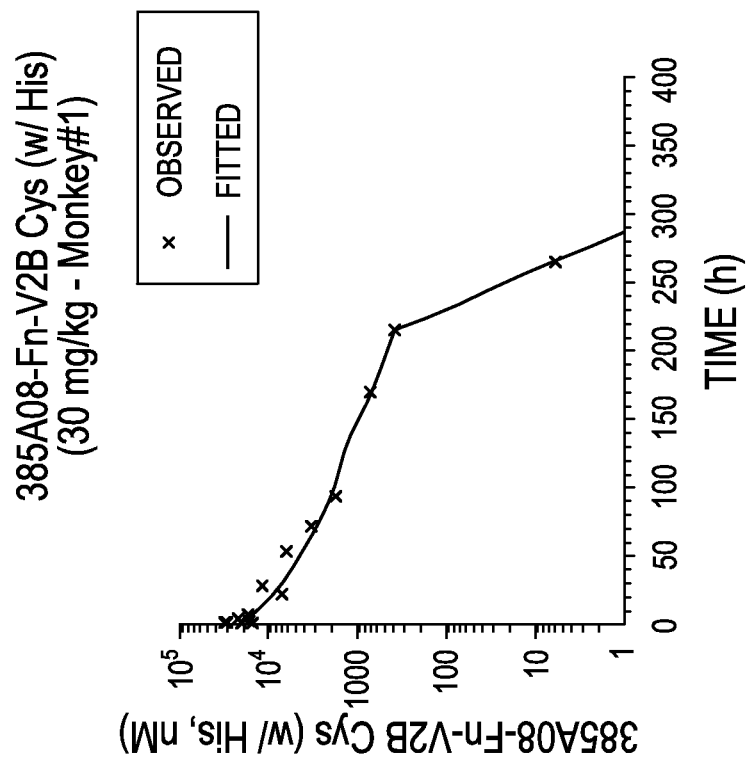
Figure 31H:
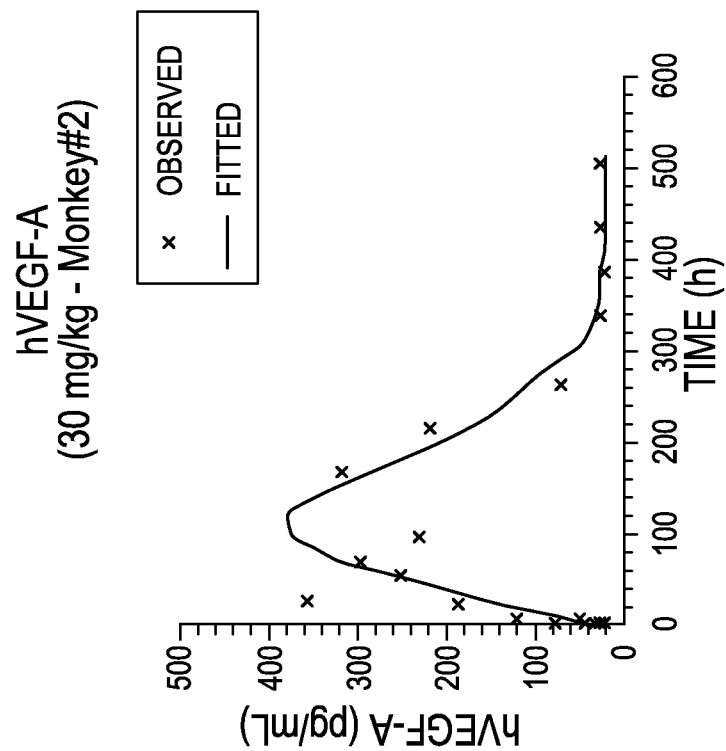
Figure 31G:
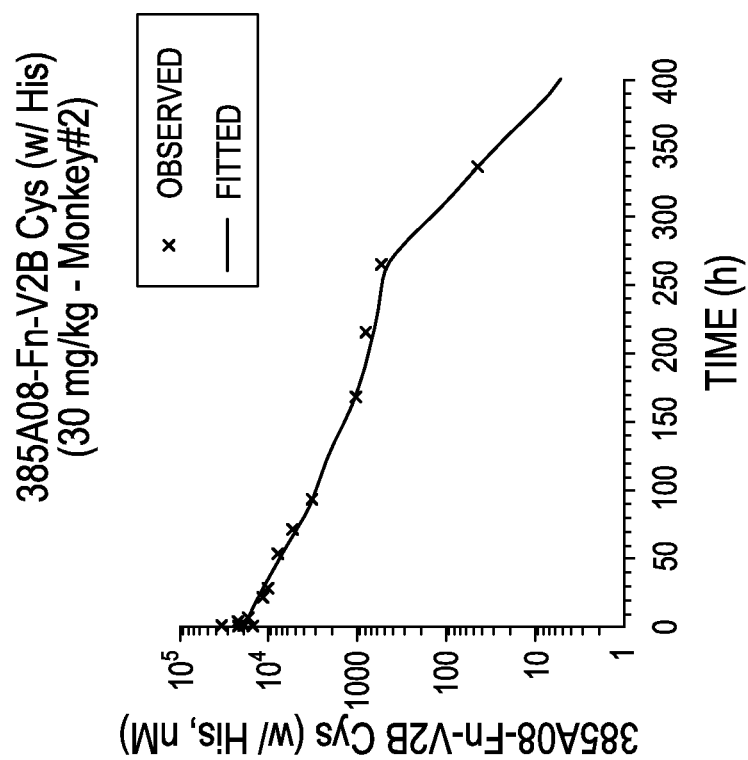
Figure 33B:
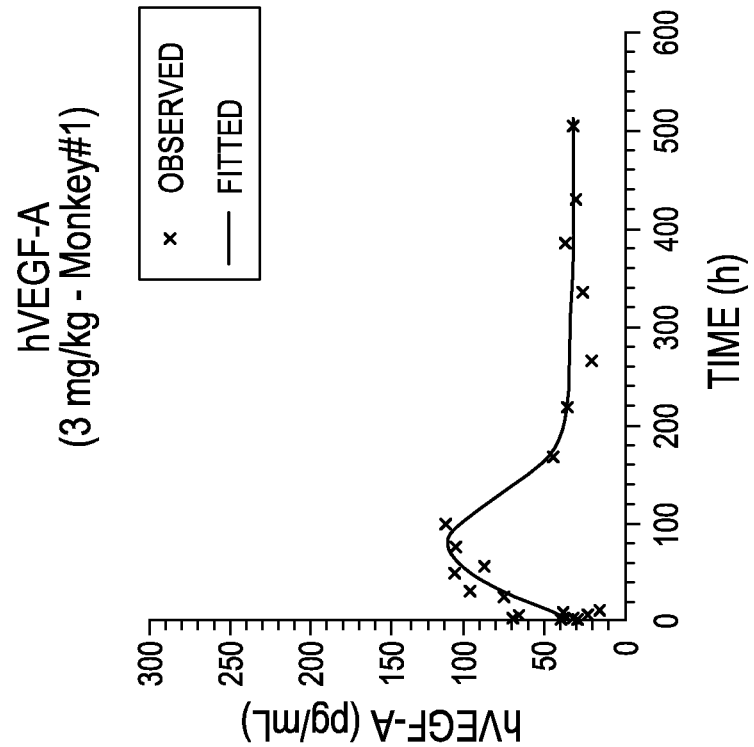
FIGS. 33A-33F. Fitted vs. observed plasma concentration-time profiles of 385A08-Fn-V2B-cys (no his) and hVEGF-A after IV administration of 3 mg/kg to monkeys (1st Dose).
Figure 33A:
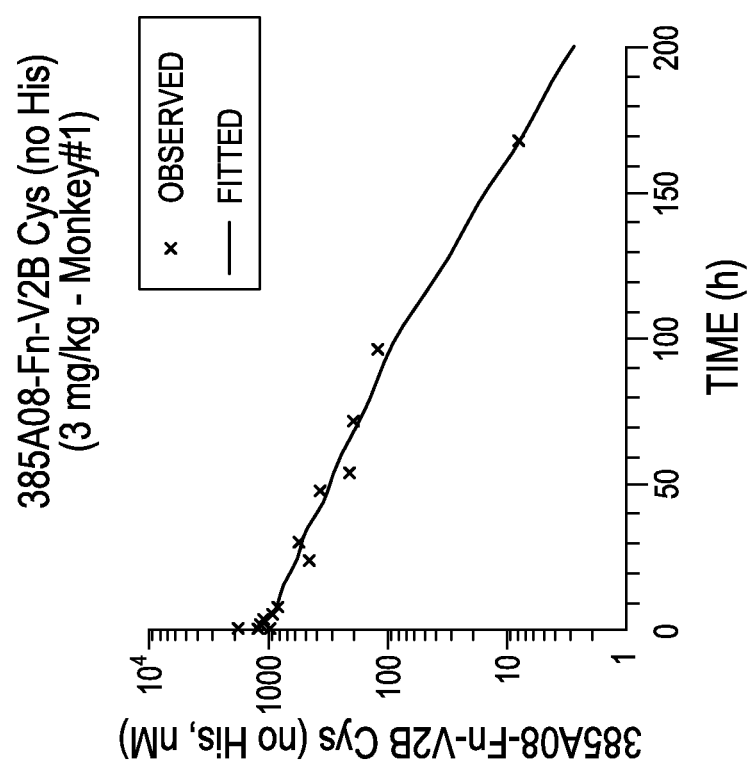
Figure 33D:
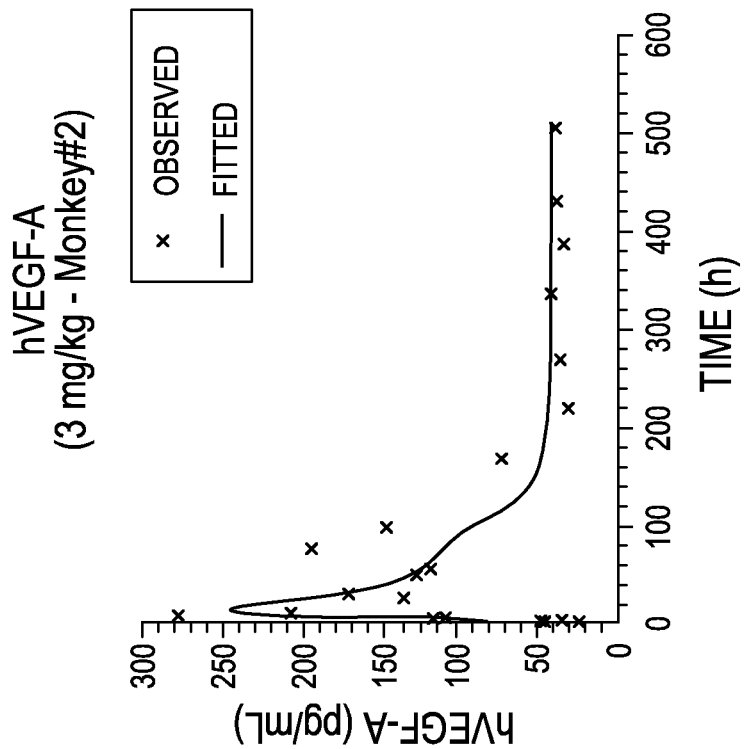
Figure 33C:
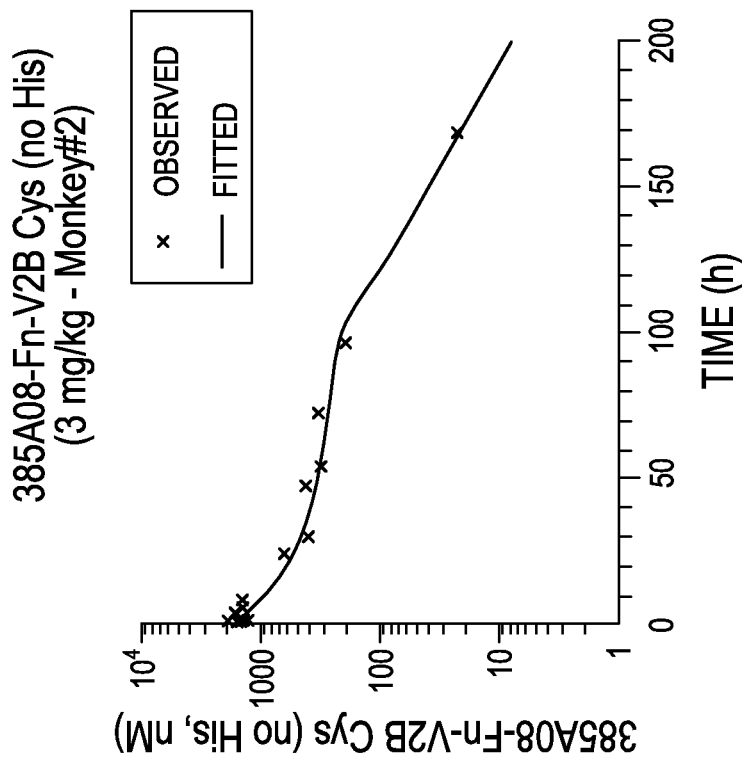
Figure 33F:
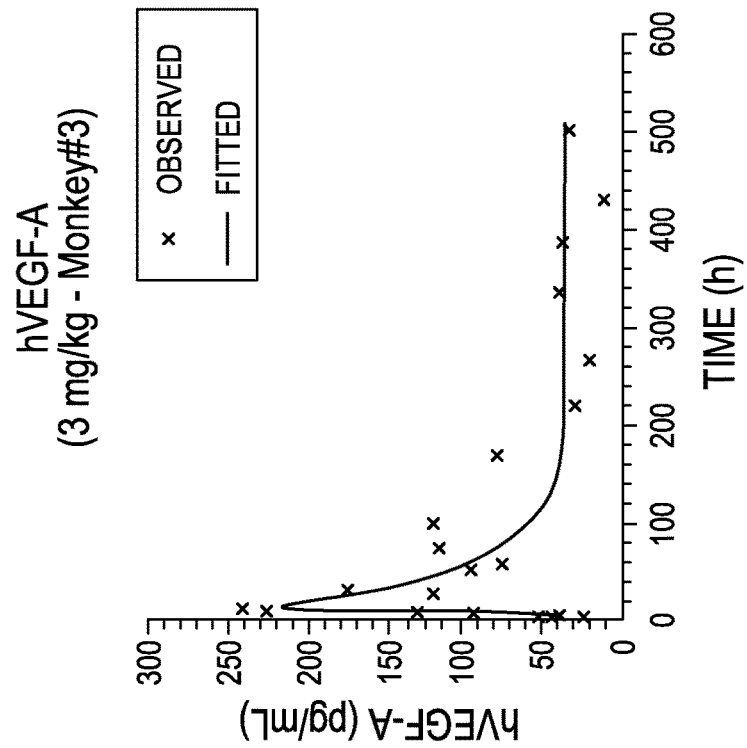
Figure 33E:
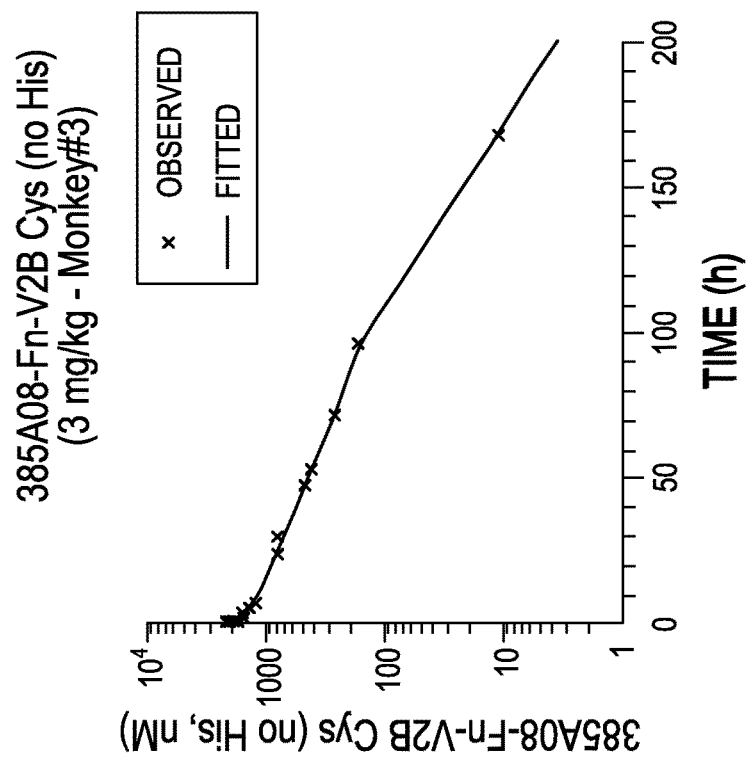

Consistent with findings observed in nude mice bearing the Rh41 tumor, the mVEGF-A levels showed dose- and time-dependent increases in plasma following IP doses of 20 and 200 mg/kg of 385A08-Fn-V2B-Cys (non-his tagged) to nude mice bearing the A673 tumor FIG. 29. Using an indirect-response PD model, the plasma IC50 of 385A08-Fn-V2B-Cys (non-his tagged) that inhibited the clearance of mVEGF-A from plasma by blocking its binding to VEGFR-2 was estimated to be 7.0 µM at 200 mg/kg. At 20 mg/kg, the dynamic range of mVEGF-A concentrations may be too low to yield meaningful estimates of PD parameters.

Single-Dose Pharmacokinetic/Pharmacodynamic Study with his-Tagged 385A08-Fn-V2B-Cys in Monkeys.

FIG. 30 summarizes the pharmacokinetic parameters of his-tagged 385A08-Fn-V2B-Cys in the monkey following a single IV dose of 3 or 30 mg/kg. His-tagged 385A08-Fn-V2B-Cys plasma concentrations exhibited a mono- or bi-exponential decline after the IV dose, with a significant drop in concentrations at the terminal phase. The drop in plasma concentrations of his-tagged 385A08-Fn-V2B-Cys was presumably due to the formation of neutralizing antibodies that were detected in plasma samples of the study. As a result, the plasma concentrations at the last time point were not included in the non-compartmental analysis.

In monkeys, his-tagged 385A08-Fn-V2B-Cys exhibited a slight dose-dependency in pharmacokinetics between 3 and 30 mg/kg. The CLTp at 3 and 30 mg/kg was 0.029 and 0.023 mL/min/kg, respectively. The Vss ranged from 0.056 to 0078 L/kg, greater than plasma volume. The MRT and T½ of his-tagged 385A08-Fn-V2B-Cys at 30 mg/kg were 57.9 and 42.7 h, respectively, slightly longer than those observed at 3 mg/kg (34.5 and 23.2 h, respectively).

PK/PD modeling was conducted to understand the relationship between the plasma concentrations of his tagged 385A08-Fn-V2B-Cys and the elevation of circulating hVEGF-A levels. To fit the drop of plasma concentrations of his tagged 385A08-Fn-V2B-Cys in the terminal phase, an added clearance mechanism due to neutralizing antibodies was included in the PK model. The fitted vs. observed PK profiles are shown in FIG. 31. The plasma IC50 of his tagged 385A08-Fn-V2B-Cys that inhibited the clearance of hVEGF-A from plasma by blocking its binding to VEGFR-2 was estimated to be 77-349 nM in monkeys, with a grand mean of 228 nM.

Single-Dose Pharmacokinetic/Pharmacodynamic Study with 385A08-Fn-V2B (Non-his Tagged) in Monkeys.

FIG. 32 summarizes the pharmacokinetic parameters of 385A08-Fn-V2B (non-his tagged) in the monkey following a 3 mg/kg IV dose as well as re-dosing the same monkeys at the same dose. Similar to his tagged 385A08-Fn-V2B-Cys, there was a drop in the plasma concentrations of 385A08-Fn-V2B (non-his tagged) at the terminal phase after the first dose. As a result, the plasma concentrations at the last time point were not included in the non-compartmental analysis. However, when 385A08-Fn-V2B (non-his tagged) was re-dosed to the same monkeys, the effect of antibodies on the pharmacokinetics of 385A08-Fn-V2B (non-his tagged) appeared not to be significant (FIG. 32). In addition, the pharmacokinetics 385A08-Fn-V2B (non-his tagged) was comparable to that of his tagged 385A08-Fn-V2B-Cys in monkeys.

Similar to what was done to his tagged 385A08-Fn-V2B-Cys, PK/PD modeling was also conducted to understand the relationship between the plasma concentrations of 385A08-Fn-V2B (non-his tagged) and the elevation of circulating hVEGF-A levels. The fitted vs. observed PK profiles are shown in FIG. 33. The plasma IC50 of 385A08-Fn-V2B (non-his tagged) that inhibited the clearance of hVEGF-A from plasma by blocking its binding to VEGFR-2 was estimated to be 68-231 nM in monkeys, with a grand mean of 159 nM. These results are consistent with those observed with his tagged 385A08-Fn-V2B-Cys.

Materials and Methods

High Throughput Protein Production (HTPP).

Selected binders containing a $His_6$ tag (SEQ ID NO: 59) were cloned into the pET9d vector, transformed into *E. coli* HMS 174 cells, inoculated into 5 ml LB medium containing 50 µg/mL kanamycin in a 24-well format and grown at 37° C. overnight. Fresh 5 ml LB medium (50 µg/mL kanamycin) cultures were prepared for inducible expression by aspirating 200 μl from the overnight culture and dispensing it into the appropriate well. The cultures were grown at 37° C. until $A_{600}$ 0.6-0.9. After induction with 1 mM isopropyl-β-thiogalactoside (IPTG), the culture was expressed for 6 hours at 30° C. and harvested by centrifugation for 10 minutes at 2,750× g at 4° C. Cell Pellets were frozen at −80° C.

Cell pellets (in a 24-well format) were lysed by resuspension in 450 μl of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM Imidazole, 1 mg/ml lysozyme, 30 ug/ml DNAse, 2 ug/ml aprotonin, pH 8.0) and shaken at room temperature for 1-3 hours. Lysates were clarified and re-racked into a 96-well format by transfer into a 96-well Whatman GF/D Unifilter fitted with a 96-well, 1.2 mL catch plate and filtered by positive pressure. The clarified lysates were transferred to a 96-well Ni-Chelating Plate that had been equilibrated with equilibration buffer (50 mM $NaH_2PO_4$, 0.5 M NaCl, 40 mM Imidazole, pH 8.0) and were incubated for 5 min. Unbound material was removed by vacuum. The resin was washed 2×0.3 ml/well with Wash buffer #1 (50 mM $NaH_2PO_4$, 0.5 M NaCl, 5 mM CHAPS, 40 mM Imidazole, pH 8.0) with each wash removed by vacuum. Next, the resin was washed with 3×0.3 ml/well with PBS with each wash step removed by vacuum. Prior to elution, each well was washed with 50 μl Elution buffer (PBS+20 mM EDTA), incubated for 5 min, and the wash discarded by vacuum. Protein was eluted by applying an additional 100 ul of Elution buffer to each well. After a 30 minute incubation at room temperature, the plate(s) were centrifuged for 5 minutes at 200 g. Eluted protein was collected in 96-well catch plates containing 5 μl of 0.5 M $MgCl_2$ added to the bottom of the elution catch plate prior to elution. Eluted protein was quantified using a BCA assay with SGE as the protein standard.

Midscale Expression and Purification of Insoluble Fibronectin-Based Scaffold Protein Binders.

For expression, selected clone(s), followed by the $His_6$ tag (SEQ ID NO: 59), were cloned into a pET9d (EMD Biosciences, San Diego, Calif.) vector and were expressed in *E. coli* HMS174(DE3) cells. Twenty ml of an inoculum culture (generated from a single plated colony) was used to inoculate 1 liter of LB medium containing 50 μg/mL kanamycin. The culture was grown at 37° C. until $A_{600}$ 0.6-1.0. After induction with 1 mM isopropyl-β-thiogalactoside (IPTG) the culture was grown for 6 hours at 30° C. and was harvested by centrifugation for 30 minutes at ≥10,000 g at 4° C. Cell Pellets were frozen at −80° C. The cell pellet was resuspended in 25 mL of lysis buffer (20 mM $NaH_2PO_4$, 0.5 M NaCl, 1× Complete™ Protease Inhibitor Cocktail-EDTA free (Roche), 1 mM PMSF, pH 7.4) using an Ultra-turrax homogenizer (IKA works) on ice. Cell lysis was achieved by high pressure homogenization (≥18,000 psi) using a Model M-110S Microfluidizer (Microfluidics). The insoluble fraction was separated by centrifugation for 30 minutes at 23,300×g at 4° C. The insoluble pellet recovered from centrifugation of the lysate was washed with 20 mM Sodium Phosphate/500 mM NaCl, pH 7.4. The pellet was resolubilized in 6.0 M Guanidine Hydrochloride in 20 mM Sodium Phosphate/500 mM NaCl, pH 7.4 with sonication followed by incubation at 37 degrees for 1-2 hours. The resolubilized pellet was filtered to 0.45 urn and loaded onto a HisTrap column equilibrated with the 20 mM Sodium Phosphate/500 mM NaCl/6.0 M Guanidine, pH 7.4 buffer. After loading, the column was washed to baseline UV A280 absorbance with 20 column volumes (CV) of equilibration buffer, followed by washing for an additional 25 CV with the same buffer. Bound protein was eluted with 500 mM Imidazole in 20 mM Sodium Phosphate/500 mM NaCl/6.0 M Guan-HCl, pH 7.4. The purified protein was refolded by dialysis against 50 mM Sodium Acetate/150 mM NaCl pH 4.5.

Midscale Expression and Purification of Soluble Fibronectin-Based Scaffold Protein Binders.

As an alternative to purification of insoluble binders, the purification of soluble binders may also be used. For expression, selected clone(s), followed by the $His_6$ tag (SEQ ID NO: 59), are cloned into a pET9d (EMD Biosciences, San Diego, Calif.) vector and are expressed in *E. coli* HMS174 (DE3) cells. Twenty ml of an inoculum culture (generated from a single plated colony) is used to inoculate 1 liter of LB medium containing 50 μg/mL kanamycin. The culture is grown at 37° C. until $A_{600}$ 0.6-1.0. After induction with 1 mM isopropyl-β-thiogalactoside (IPTG) the culture is grown for 6 hours at 30° C. and is harvested by centrifugation for 30 minutes at ≥10,000×g at 4° C. Cell Pellets are frozen at −80° C. The cell pellet is resuspended in 25 mL of lysis buffer (20 mM $NaH_2PO_4$, 0.5 M NaCl, 1× Complete™ Protease Inhibitor Cocktail-EDTA free (Roche), 1 mM PMSF, pH 7.4) using an Ultra-turrax homogenizer (IKA works) on ice. Cell lysis is achieved by high pressure homogenization (≥18,000 psi) using a Model M-110S Microfluidizer (Microfluidics).

The soluble fraction is separated by centrifugation for 30 minutes at 23,300 g at 4° C. The supernatant is clarified via 0.45 μm filter. The clarified lysate is loaded onto a HisTrap column (GE) pre-equilibrated with 20 mM $NaH_2PO_4$, 0.5 M NaCl, pH 7.4. The column is then washed with 25 column volumes of 20 mM $NaH_2PO_4$, 0.5 M NaCl, pH 7.4, followed by 20 column volumes of 20 mM $NaH_2PO_4$, 0.5 M NaCl, 25 mM imidazole pH 7.4, and then 35 column volumes of 20 mM $NaH_2PO_4$, 0.5 M NaCl, 40 mM imidazole pH 7.4. Protein is eluted with 15 column volumes of column volumes of 20 mM $NaH_2PO_4$, 0.5 M NaCl, 500 mM imidazole pH 7.4, fractions are pooled based on absorbance at $A_{280}$ and are dialyzed against 1×PBS, 50 mM Tris, 150 mM NaCl, pH 8.5 or 50 mM NaOAc; 150 mM NaCl; pH4.5. Any precipitate is removed by filtering at 0.22 μm.

Large scale expression and purification of the fibronectin-based scaffold protein binders was also used. Other than the quantities produced, this method is substantially similar to the insoluble midscale purification methods.

Biophysical Characterization of Fibronectin-Based Scaffold Protein Binders

Size Exclusion Chromatography (SEC).

Standard size exclusion chromatography (SEC) was performed on the proteins purified from the HTPP, midscale processes, and large scale processes (0.1 to 1 μg of protein for HTPP and 10-50 μg for midscale). SEC of HTPP derived material was performed using a Superdex 200 5/150 column (GE Healthcare) or on a Superdex 200 10/30 column (GE Healthcare) for midscale material on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, pH 6.8 at appropriate flow rate of the SEC column was employed. Gel filtration standards (Bio-Rad Laboratories, Hercules, Calif.) were used for molecular weight calibration.

Mass Spectrometry.

The midscale and large scale purified $^{10}$Fn3-based binders were further analyzed by LC-MS (Water's 2695 liquid chromatography HPLC system coupled with Waters Q-TOF API mass spectrometer, Waters Corporation, Milford, Mass.). Samples were diluted to approximately 0.5 mg/ml with HPLC grade water. Approximately 5 μl of diluted sample was injected onto a Jupiter C18 column (Catalog number 00G-4053-80, Phenomenex). Buffer A: 0.02% TFA+0.08% formic acid in HPLC grade water. Buffer B: 0.02% TFA+0.08% formic acid in HPLC grade acetonitrile. Sample was eluted with gradient (Table 1) at a flow rate of 0.2 ml/minutes.

Differential Scanning Calorimetry (DSC).

Differential Scanning calorimetry (DSC) analysis of the midscale and large scale purified $^{10}$Fn3-based binders was performed to determine the $T_m$. A 1 mg/ml solution was scanned in a N-DSC II calorimeter (calorimetry Sciences Corp) by ramping the temperature from 5° C. to 95° C. at a rate of 1 degree per minute under 3 atm pressure. The data was analyzed versus a control run of the appropriate buffer using a best fit using Origin Software (OriginLab Corp).

Determination of Binding Affinity Using Surface Plasmon Resonance (BIAcore) Analysis Selected HTPP purified fibronectin based scaffold proteins, and selected midscale and large scale versions of the tandem construct 385A08-Fn-V2B (pegylated and non-pegylated versions; his-tag and non-his-tag versions) were evaluated for their kinetic behavior towards IGF-IR using surface plasmon resonance. A capture assay was developed utilizing a human IGF-IR-Fc fusion. A similar reagent had been described by Forbes et al. (Forbes et al. 2002, European J. Biochemistry, 269, 961-968). The extracellular domain of human IGF-IR (aa 1-932) was cloned into a mammalian expression vector containing the hinge and constant regions of human IgG1. Transient transfection of the plasmid produced a fusion protein, IGF-IR-Fc as described next. 293T cells (a human embryonic kidney cell line expressing SV40 large T antigen) were obtained from Genehunter (Nashville, Tenn.) and maintained according to the manufacturer's instructions. Briefly, 12×10$^6$ cells were seeded in T175 flasks (Falcon) for transfection with the appropriate DNA preparations (Qiagen, Valencia, Calif.) and Lipofectamine 2000 (Invitrogen, Carlsbad, Calif.) and Optimem (Invitrogen, Carlsbad, Calif.). Conditioned media was collected at 72 hrs and expression verified by Western blotting using anti-human IgG-HRP (Pierce, Rockford, Ill.) and anti-IGF-IR polyclonal antibody (R&D Systems, Minneapolis, Minn.). This IGF-IR-Fc fusion protein was subsequently purified by Protein A chromatography.

One method of obtaining kinetic measurements, which was used for the HTPP purified constructs (non-pegylated, his tag versions) was to capture the IGF-IR-Fc on Protein A/G immobilized on Biacore CM5 chips (GE, Piscataway, N.J.) by amine coupling. The kinetic analysis involved the capture of IGF-IR-Fc on Protein A/G followed by injection of a concentration series of the fibronectin based scaffold proteins in solution and regeneration of the Protein A/G surface by glycine pH 2.0. Protein concentrations from HTPP material are approximate, therefore $K_D$ determinations are also approximate. Sensorgrams were obtained at each concentration and fitted via Biaevaluation to determine the rate constants $k_a$ ($k_{on}$) and $k_d$ ($k_{off}$). The dissociation constant, $K_D$, was calculated from the ratio of rate constants $k_{off}/k_{on}$.

An alternative method is to capture the IGF-IR-Fc on Protein A. This method was used for calculating the affinity and kinetics of certain versions of the construct 385A08-Fn-V2B-cys (both pegylated and non-pegylated and with or without his tag) from midscale and large scale materials. Specifically, IGF-IR-Fc was captured on Protein A immobilized on a Biacore CM5 sensor chip by amine coupling. VEGFR2-Fc was immobilized directly on a CM5 chip by amine coupling. The affinity and kinetic analysis involved the capture of IGF-IR-Fc on Protein A followed by injection of the tandem adnectin in solution over IGF-IR-Fc and VEGFR2-Fc. The analytical surface was regenerated between samples with glycine pH 1.5. Sensorgrams were obtained at each concentration and were evaluated using Biacore T100 evaluation software to determine the rate constants $k_a$ ($k_{on}$) and $k_d$ ($k_{off}$).

Another method to assess the functionality of the IGF-IR domain is to capture the IGF-IR-Fc on anti-human IgG (GE, Piscataway, N.J.). This was done for the midscale purified construct 385A08-Fn-V2B (non-pegylated, his-tag) as described in Example 5 above. The anti-human IgG was immobilized on flow cells 1 and 2 of a CM5 chip surface according the manufacturer's instructions. 100 nM human IGF-IR-Fc was injected for 2 minutes at 10 ul/min on flow cell 2. Subsequently a concentration series of the midscale prep was injected across both flow cell surfaces at 50 uL/min. Two injections of 50 mM Glycine pH 1.7 were used to regenerate the surface.

The functionality of the V2B domain was assessed by evaluating a concentration series of the midscale and large scale purification of the tandem construct 385A08-Fn-V2B (pegylated, and non-pegylated versions, his-tag and non-his-tag versions) vs. VEGFR2-Fc that was directly immobilized on a CM5 chip surface (GE, Piscataway, N.J.). VEGFR2-Fc (R&D Systems, MN) was diluted to 12 ug/mL in 50 mM Acetate pH 5.0 for an immobilization level of ~1300 RU. Varying concentrations of 385A08-Fn-V2B in the solution phase were monitored for association (2 minutes) and dissociation (10 minutes) kinetics at a flow rate of 50 uL/min. Two 30 second injections of 50 mM glycine pH 1.7 were used to regenerate the surface.

Pegylation

Multi-valent fibronectin based scaffold proteins, such as V/I $^{10}$Fn3-based binders, can be pegylated with various sizes and types of PEG. To allow for pegylation, the protein is typically modified near the C-terminus by a single point mutation of an amino acid, typically a serine, to a cysteine. PEGylation of the protein at the single cysteine residue is accomplished by conjugating various maleimide-derivatized PEG forms, combining the PEG reagent with the protein solution and incubating. Confirmation of the PEGylation of the protein can be confirmed by SDS-Page and/or SE-HPLC methods that can separate the non-PEGylated protein from the PEGylated protein.

For example, the construct 385A08-Fn-V2B was pegylated by replacing a serine that was at position 203 with a cysteine. The resulting construct, 385A08-Fn-V2B-Cys, was then conjugated with a 40 kD PEG. The PEG reagent was mixed with the protein construct (385A08-Fn-V2B-Cys) in solution and incubated. Studies to confirm the pegylation were also conducted as described in the paragraph above. Studies were also conducted on the tandem construct with linear PEG. In addition, this type of pegylation can also be done with a his-tagged protein.

Additionally, the linear and branched pegylated versions of the construct 385A08-Fn-V2B-Cys were used to conduct certain pharmacokinetic studies in mice to assess the difference between linear vs. branched PEG. Both were 40 kD PEGs, and the linear version of this construct also included a his-tag.

V/I $^{10}$Fn3-based binders may also be pegylated using an alternative method. Five ml of an inoculum culture of BL21(DE3) E. coli cells containing a T7 ploymerase driven pET29 plasmid encoding a V/I $^{10}$Fn3-based binder is generated from a single plated colony and used to inoculate 1 liter of auto-induction media ("ONE" medium, EMD Biosciences, San Diego, Calif.) containing 50 μg/mL kanamycin. Expression is carried out at 18° C. after initial growth at 37° C. and harvested by centrifugation for 10 minutes at ~10,000×g at 4° C. Cell pellets are frozen at 80° C. The cell pellet is resuspended in 10 mL of lysis buffer (20 mM $NaH_2PO_4$, 0.5 M NaCl, 5 mM Immidazole, pH 7.4) and mechanically lysed using an Avestin homgenizer. The soluble fraction is separated by centrifugation for 15 minutes at 23,300×g at 4° C. The supernatant is decanted and the pellet is solubilized in Lysis buffer (above) supplemented with 4 M to 6 M guanidine hydrochloride (GdnHCl). Solubilized protein is then purified on a suitably sized NiNTA column (Qiagen, Inc.) pre-equilibrated with the GdnHCL supplemented Lysis Buffer. The column is then washed with 5 to 10 column volumes of the same buffer, followed by elution with the same buffer supplemented with 300 mM Immidazole. The fractions eluted off the column containing the protein of interest are diluted to 2-3 mgs/mL protein and then combined with a 1.2-1.5 molar excess of solid NEM-PEG (40 kDa branched or other). The mixture is allowed to react at room temperature for 30 minutes or until the reaction is complete. The entire reaction volume is then placed into a dialysis bag (5,000 Da Molecular Weight cutoff) and the mixture is subjected to a dialysis refolding process. The dialysate from this procedure contains properly folded, PEGylated materials plus excess reactants. The mixture of products and excess reactants from the PEGylation reaction are clarified via centrifugation or filtration prior to loading them onto a cation exchange chromatography column (SP Sepharose or Resource S, GE Healthcare). The column is developed with 150 mM to 1 M NaCl gradient in the NaOAc background buffer. Studies to confirm the pegylation are conducted as described above.

Competitive Blocking Assays

R+ Competitive Blocking Assay.

R+, a gift from Renato Baserga (Thomas Jefferson University, Philadelphia, Pa.), is a mouse embryo fibroblast overexpressing human IGF-IR in the context of a deletion in the mouse IGF-IR gene. Cells were plated in 96 well plates at a concentration of 20,000 cells per well in DMEM (Invitrogen, Carlsbad, Calif.) containing 5% calf serum (Hyclone, Logan, Utah). The following day, cells were washed twice in serum free DMEM containing 0.1% BSA (Invitrogen, Carlsbad, Calif.). After the washes, the cells were incubated at 4° C. for 10 minutes in binding buffer (serum free DMEM+0.1% BSA) containing increasing concentrations of IGF-IR antagonists or controls. Typical controls included the mono-specific $^{10}$Fn3-based IGF-IR binder (AT580-PEG40, SEQ ID NO: 27) (positive control) or the mono-specific $^{10}$Fn3-based VEGFR2 binder (Peg-V2Bshort, SEQ ID NO: 28) (negative control). Following this brief exposure to antagonists, R+ cells were additionally exposed to 200 nM of a bi-valent $^{10}$Fn3-based IGF-IR binder (AT580-PEG20-AT580, SEQ ID NO: 27) labeled with IRDye 800CW according to the manufacturer instructions (Li-Cor Biosciences, Lincoln, Nebr.). After incubation for 4 hours at 4° C., cells were washed twice in binding buffer and visualized on the Odyssey Infrared Imaging System (Li-Cor Biosciences, Lincoln, Nebr.). The resulting data was analyzed using GraphPad Prism (GraphPad Software, La Jolla, Calif.).

293:KDR Competitive Blocking Assay.

293:KDR (Sibtech, Brookfield, Conn.) were plated in 96 well plates at a concentration of 25,000 cells per well in DMEM (Invitrogen, Carlsbad, Calif.) containing 10% fetal bovine serum (Hyclone, Logan, Utah). The following day, cells were washed twice in serum free DMEM containing 0.1% BSA (Invitrogen, Carlsbad, Calif.). After the washes, the cells were incubated at 4° C. for 10 minutes in binding buffer (serum free DMEM+0.1% BSA) containing increasing concentrations of VEGFR-2 antagonists or controls. Typical controls included the mono-specific $^{10}$Fn3-based VEGFR2 binder (Peg-V2Bshort, SEQ ID NO: 28) (positive control) or the mono-specific $^{10}$Fn3-based IGF-IR binder (AT580-PEG40, SEQ ID NO: 27) (negative control). Following this brief exposure to antagonists, 293:KDR cells were additionally exposed to 200 nM Peg-V2Bshort labeled with IRDye 800CW according to the manufacturer instructions (Li-Cor Biosciences, Lincoln, Nebr.). After incubation for 4 hours at 4° C., cells were washed twice in binding buffer and visualized on the Odyssey Infrared Imaging System (Li-Cor Biosciences, Lincoln, Nebr.). The resulting data was analyzed using GraphPad Prism (GraphPad Software, La Jolla, Calif.).

In Vitro Proliferation Assays

RH41. RH41 cells were grown in RPMI medium supplemented with 10% fetal bovine serum, 10 mM Hepes, glutamax, penicillin and streptomycin. Cell proliferation was evaluated by [$^3$H]-thymidine incorporation or colorimetric methods. For evaluation of [$^3$H]-thymidine incorporation, cells were plated at an optimized density (4K cells/well) in 96-well plates, incubated overnight at 37° C., then exposed to a serial dilution of the fibronectin based scaffold proteins. After 72 hours incubation, cells were pulsed with 4 μC/ml [$^3$H]-thymidine (Amersham Pharmacia Biotech, UK) for 3 hours, trypsinized, harvested onto UniFilter-96 GF/B plates (PerkinElmer, Boston, Mass.) and scintillation was measured on a TopCount NXT (Packard, Conn.). Results were expressed as an IC50, which is the drug concentration required to inhibit cell proliferation by 50% compared to untreated control cells. The mean IC50 and standard deviation from multiple tests for each cell line were calculated. For colorimetric evaluation, cells were plated in 96 well plates at a concentration of 5,000 cells per well in 90 ul/well of RPMI-glutamax (Invitrogen, Carlsbad, Calif.) containing 10% fetal bovine serum (Hyclone, Logan, Utah) and incubated for 24 hours, 37° C., 5% $CO_2$. 10 ul of 10× concentrations of $^{10}$Fn3-based IGF-IR antagonists were added to the wells and incubated for 72 hours at 37° C., 5% $CO_2$. After the proliferation period, cells were exposed to Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data was analyzed using Softmax Pro 5 software (Molecular Devices, Sunnyvale, Calif.).

Ba/F3.

Murine Ba/F3 cells stably expressing a VEGFR2 fusion protein (comprising the extracellular domain of hVEGFR2 and the intracellular domain of hEpoR) were plated in 96-well plates at 25,000 cells/well in 90 uL growth media containing 15 ng/mL VEGF-A. Serial dilutions of fibronectin scaffold domain proteins were prepared at 10× final concentration, and 10 uL of the protein was added to each well. Plates were incubated at 37° C./5% $CO_2$ for 48-72 hours. Cell proliferation assay reagent (CellTiter 96, Promega) was added to each well (20 μL/well), and the plates were further incubated for 3-4 hours. At the end of the incubation period, absorbance was read (A490) in a 96-well plate reader.

HMVEC-L.

Primary human microvascular endothelial cells from Lung (HMVEC-L), were purchased from Lonza (Cat# CC-2527; Walkersville, Md.) and maintained in EGM-2 MV Singlequots (Lonza, Cat# CC-3202), then switched to RPMI-1640+Glutamax supplemented with 2% Heat Inactivated fetal calf serum (FCS), 10 mM Hepes, 15 ng/ml recombinant Human VEGF (Biosource), and 50 ng/ml recombinant Human IGF-1 (PeproTech) for the growth assay. Proliferation was evaluated by incorporation of [$^3$H]-thymidine into DNA after exposure of cells to compounds in the presence of 10% Fetal Calf Serum (FCS). Typical controls included the following: IGF-IR monoclonal antibody mAB391 (R & D Systems, Minneapolis, Minn.), a mono-specific $^{10}$Fn3-based IGF-IR binder (AT580-PEG40, SEQ ID NO: 27), a mono-specific $^{10}$Fn3-based VEGFR-2 binder (Peg-V2Bshort, SEQ ID NO: 28), and a wild type $^{10}$Fn3-based protein that does not bind to a target (SGE). HMVEC-L cells were plated at 1,500 cells/well in 96-well microtiter Falcon plates (cell density was optimized for this cell type). After 72 hours incubation at 37° C., cells were pulsed with 4 µCi/ml [6-$^3$H] thymidine (Amersham Pharmacia Biotech, UK) for 3 hours, trypsinized, harvested onto UniFilter-96 GF/B plates (PerkinElmer, Boston, Mass.), and scintillation counts were measured on a TopCount NXT (Packard, Conn.). Results are expressed as the drug concentration required for inhibition of cellular proliferation by 50% to that of untreated control cells ($IC_{50}$).

NCI-H929.

NCI-H929 (ATCC, Manassas, Va.), an IGF-dependent human plasmacytoma cell line, was plated in 96 well plates at a concentration of 25,000 cells per well in DMEM (Invitrogen, Carlsbad, Calif.) containing 10% fetal bovine serum (Hyclone, Logan, Utah) in the presence of IGF-IR antagonists or controls. Typical controls included the following: IGF-IR monoclonal antibody MAB391 (R&D Systems, Minneapolis, Minn.), a mono-specific $^{10}$Fn3-based IGF-IR binder (AT580-PEG40, SEQ ID NO: 27), a mono-specific $^{10}$Fn3-based VEGFR-2 binder (Peg-V2Bshort, SEQ ID NO: 28), and a wild type $^{10}$Fn3-based protein that does not bind to a target (SGE). Cells were allowed to proliferate for 72 hours at 37° C., 5% $CO_2$ After the proliferation period, cells were exposed to Cell Titer 96 Aqueous Proliferation Reagent (Promega, Madison, Wis.) and allowed to incubate for an additional four hours. Absorbance at 490 nm was measured on a Spectramax Plus 384 (Molecular Devices, Sunnyvale, Calif.), and the resulting data was analyzed using GraphPad Prism (GraphPad Software, La Jolla, Calif.).

Cell-Based Signal Transduction Assays

HEK293/KDR and PAE/KDR Assays.

HEK293/KDR and PAE/KDR cells (Sibtech, Inc) were cultured in DMEM with GlutaMAX™-1 (Gibco, Carlsbad, Calif.) containing 10% fetal bovine serum (FBS), penicillin, streptomycin, HEPES and puromycin, and grown to ~70% confluency. Cells were placed into starvation medium (DMEM-GlutaMAX, 0.5% FBS, penicillin, streptomycin, HEPES and puromycin) overnight at 37° C., then stimulated with VEGF or IGF-1 (50 ng/ml, PeproTech, Rocky Hill, N.J.) for 10 min at 37° C. Unstimulated cells were included as controls. Cells were rinsed twice with ice-cold PBS on ice and extracts were prepared in TTG lysis buffer (1% Triton X-100, 5% glycerol, 0.15 M NaCl, 20 mM Tris-HCl pH 7.6, Complete tablet (Roche, Indianapolis, Ind.) and Phosphatase Inhibitor Cocktail 2 (Sigma, Milwaukee, Wis.). Protein concentrations of total cell lysates were determined using a BCA assay kit (Pierce, Rockford, Ill.). Lysates (30 µg) were resolved by SDS-PAGE (Invitrogen, Carlsbad, Calif.), transferred to nitrocellulose membranes (Bio-Rad Laboratories, Hercules, Calif.) and immunoblotted with antibodies to phospho VEGFR (Tyr 996) (Santa Cruz Biotechnology, Carlsbad, Calif.), phospho IGF1R/IR (Tyr1135/1136)/Insulin Receptor (Tyr1150/1151), phospho Akt (Ser 473), phospho p44/42 MAPK (Thr202/Tyr204) (Cell Signaling Technology, Beverly, Mass.) or total Actin (Chemicon International, Temecula, Calif.) in Odyssey Blocking Buffer with 0.1% Tween 20 (Li-Cor Biosciences, Lincoln, Nebr.). Membranes were incubated with the appropriate infrared-labeled secondary antibodies from Rockland Immunochemicals, Inc. (Gilbertsville, Pa.) and Molecular Probes (Carlsbad, Calif.). Protein visualization was performed using Li-Cor Biosciences Odyssey Infrared Imaging System.

HEK293/KDR cells (Sibtech, Inc) were cultured as described above. VEGFR-IGF-IR multivalent fibronectin scaffold domains were diluted in starvation media and added to cells at a final concentration of 100 and 10 nM for 1 hour at 37° C. Cells were stimulated with VEGF-IGF-1 ligand combination (both 50 ng/ml final concentration, PeproTech, Rocky Hill, N.J.) for 10 min at 37° C. Unstimulated cells were included as controls. Cell lysates were prepared as described above. Lysates (30 µg) were resolved by SDS-PAGE (Invitrogen, Carlsbad, Calif.), transferred to nitrocellulose membranes (Bio-Rad Laboratories, Hercules, Calif.) and probed with antibodies to total VEGFR, phospho VEGFR (Tyr 996), total IGF-1R (Santa Cruz Biotechnology, Carlsbad, Calif.), phospho IGF1R/IR (Tyr1135/1136)/Insulin Receptor (Tyr1150/1151), total Akt, phospho Akt (Ser 473), total MAPK, phospho 44/42 MAPK (Thr202/Tyr204) (Cell Signaling Technology, Beverly, Mass.) or Actin (Chemicon International, Temecula, Calif.). Antibodies were detected after incubation with infrared-labeled secondary antibodies using Li-Cor Biosciences Odyssey Infrared Imaging System.

PAE/KDR cells (Sibtech, Inc) were cultured as described above. VEGFR-IGF-IR multivalent fibronectin scaffold domains were diluted in starvation media and added to cells at a final concentration of 100 and 10 nM for 1 hour at 37° C. Cells were stimulated with VEGF-IGF-1 ligand combination (both 50 ng/ml final concentration, PeproTech, Rocky Hill, N.J.) for 10 min at 37° C. Unstimulated cells were included as controls. Cell lysates were prepared as described above. Lysates (30 µg) were resolved by SDS-PAGE (Invitrogen, Carlsbad, Calif.), transferred to nitrocellulose membranes (Bio-Rad Laboratories, Hercules, Calif.) and probed with antibodies to total VEGFR, phospho VEGFR (Tyr 996), total IGF-1R (Santa Cruz Biotechnology, Carlsbad, Calif.), phospho IGF1R/IR (Tyr1135/1136)/Insulin Receptor (Tyr1150/1151), total Akt, phospho Akt (Ser 473), total MAPK, phospho 44/42 MAPK (Thr202/Tyr204) (Cell Signaling Technology, Beverly, Mass.) or Actin (Chemicon International, Temecula, Calif.). Antibodies were detected after incubation with infrared-labeled secondary antibodies using Li-Cor Biosciences Odyssey Infrared Imaging System.

Western Blot Analysis to Measure Signaling Pathways Inhibited in HMVEC-L Cells or Rh41 Cells HMVEC-L cells were cultured in EGM-2MV Singlequots complete media (Lonza, Cat# CC-3202), and grown to ~70% confluence. Cells were placed into starvation medium (Basal EBM-2 media, 0.3% BSA) for 6 hrs, 37° C., 5% $CO_2$. Test reagents were diluted in starvation media and added to cells at a final concentration of 100 nM for 1 hr at 37° C. Cells were stimulated with a combination of VEGF and IGF-1 ligands (50 ng/ml each), (VEGF, R&D Systems, #293-VE/CF; IGF1, PeproTech, Rocky Hill, N.J., #100-11) for 10 min at 37° C. Unstimulated cells served as controls.

Rh41 cells were cultured in RPMI (Invitrogen, Carlsbad, Calif.) containing 10% fetal bovine serum (FCS), penicillin, streptomycin, and HEPES, and grown to ~70% confluence. Rh41 is a human rhabdomyosarcoma tumor cell line which was obtained from Dr. Lee Helman (NIH), and maintained in RPMI-1640+Glutamax, in the presence of 10% FCS, 10 mM HEPES; Rh41 cells are IGF-dependent and are very sensitive to inhibition by antagonists of IGF-1R (i.e., small molecules, mononectins, and mAB391). Rh41 cells were placed into starvation medium (RPMI, 0.3% BSA) overnight at 37° C. Test reagents were diluted in starvation media and added to cells at a final concentration of 100 nM for 1 hour at 37° C. Cells were stimulated with a combination of VEGF and IGF-1 ligands (50 ng/ml each), for 10 min at 37° C. Typical controls included the following: Unstimulated cells, IGF-1R monoclonal antibody mAB391 (R & D Systems, Minneapolis, Minn.), a mono-specific $^{10}$Fn3-based IGF-IR binder (AT580-PEG40, SEQ ID NO: 27), or a mono-specific $^{10}$Fn3-based VEGFR-2 binder (Peg-V2Bshort, SEQ ID NO: 28).

HMVEC-L or Rh41 cells were rinsed twice with ice-cold PBS on ice and extracts were prepared in TTG lysis buffer (1% Triton X-100, 5% glycerol, 0.15 M NaCl, 20 mM Tris-HCl pH 7.6, Complete Tablet (Roche, Indianapolis, Ind.) and Phosphatase Inhibitor Cocktail 2 (Sigma, Milwaukee, Wis.). Protein concentrations of total cell lysates were determined using a BCA assay kit (Pierce, Rockford, Ill.). Equal amounts of protein from each lysate (40 ug) were added to each well of a gel (NuPAGE 4-12% Bis-Tris Gel, Invitrogen, Carlsbad, Calif.). Proteins were separated on a NuPAGE gel, transferred to nitrocellulose membranes (Bio-Rad Laboratories, Hercules, Calif.) and incubated in Odyssey Blocking buffer (Li-Cor Biosciences) for 1 hr at room temperature. Inhibition of phosphorylation was measured by probing Western blots with antibodies specific for IGF-1R (Phospho-IGF-1Rβ, (Tyr1135/1136)/IR, (Tyr1150/1151) (19H7) Antibody, (Cell Signaling #3024)), IGF-1Rβ (Santa Cruz Biotechnology, Inc. sc-713), Akt (pAkt (Ser473) (Cell Signaling #4051)), Akt (Cell Signaling #9272), MAPK (p-p44/42) MAPK (Thr202/Tyr2040) (E10) (Cell Signaling #9106), (MAPK Cell Signaling #9102), and VEGFR-2 (pFlk-1) (Tyr996)-R, (Santa Cruz Biotechnology, Inc. sc-16629R), VEGFR-2 (Flk-1) (C-1158), (Santa Cruz Biotechnology, Inc. sc-504), total GAPDH (Cell Signaling #2118) in Odyssey Blocking Buffer with 0.1% Tween 20 (Li-Cor Biosciences, Lincoln, Nebr.), for 3 hrs at room temperature. Membranes were washed 3 times in TBS with 0.1% Tween-20 and then incubated with IR-labeled secondary antibodies for 1 hr at room temperature. Protein analysis was performed utilizing the Odyssey Infrared Imaging System (Li-Cor Biosciences) which enables simultaneous and independent detection of fluorescent signals.

Ca2+ Flux Assays

HMVEC-L cells were plated at $2.5 \times 10^4$ cells/well on poly-D-Lysine-coated 96-well plates (Falcon #356640) in EGM2-MV Singlequots complete media (Lonza, Cat# CC-3202). Cells were starved overnight in basal EBM media (Lonza). The day of the assay, test reagents were serial diluted in HHP buffer (10 mM HEPES, 2.5 mM probenecid [Sigma #P8761] in HBSS [GibcoBRL #14025-076]+0.1% BSA) and added to the cells after aspirating EBM media. Calcium-4 dye kit (Molecular Devices, #R8142) was added at the same time as the HHP buffer, and cells were incubated for 1 hour at 37° C. $Ca^{2+}$ release was triggered by the addition of 50 ng/ml VEGF (Invitrogen #PHG0145). $Ca^{2+}$ flux was monitored by measurement on a FLIPR (Molecular Devices).

Human Microvascular Endothelial Cell Tube Formation

Matrigel™ plates were prepared by thawing Matrigel™ (BD Biosciences, #356237) overnight at 4° C. Matrigel™ (300 μl/well) was added to a 24-well plate and subsequently incubated at 37° C. for 30 minutes in order for the gel to polymerize. HMVEC-L cells were cultured in EGM-2MV complete media (Lonza, Cat# CC-3202), and grown to ~70% confluence. The cells were resuspended ($1 \times 10^5$ cells/ml) with test compounds (100 nM) or without compounds in EGM-2MV complete media. 1 ml of the cell suspension was added to each well. Plates were incubated for 12 hrs at 37° C., in 5% $CO_2$. The growth medium was aspirated and 1 ml of 0.3% Glutaraldehyde (VWR, #GX015305-1) was added to each well at room temperature for 30 minutes. The media was aspirated and cells were washed with 1 ml wash buffer (Cell Spreading Reagent Kit, Pierce, #K0600011). 500 μl of permeabilization solutions were added followed by incubation at room temperature for 15 minutes. The media was aspirated and cells were washed with 1 ml wash buffer. 500 μl of stain solution was added to each well and incubated at room temperature in the dark for 1 hr. The solution was removed by aspiration and washed 3× with wash buffer. The plates were sealed, and imaged on an ArrayScan HCS Reader. The angiogenic index, which is a measure of the imaged area occupied by microvascular tubes, was automatically calculated and reported for each well.

Single-Dose PK in Mice

The pharmacokinetics of 385A08-Fn-V2B-Cys (SEQ ID NO: 9) pegylated with 40 kD linear or 40 kD branched PEG was studied in mice. Two groups of non-fasted animals (N=3-4 per group, 20-25 g) received Adnectin as an intravenous (IV) bolus doses via the tail vein (5 mL/kg). The dose was 50 mg/kg. Prior to dosing, the compound was diluted from a stock solution to an appropriate dosing solution concentration in phosphate buffered saline (PBS). Serial blood samples (~0.05 mL) were obtained by nicking the lateral tail vein. For the IV route, the sampling time points were 0.08, 0.5, 1, 2, 6, 12, 24, 48, 96, and 171 h post dose. Plasma samples were harvested by diluting blood sample into a citrate phosphate dextrose solution in a 1:1 ratio and were stored at −20° C. until analysis.

Single-Dose PK/PD Study in Rh41-Tumored Mice

Pharmacodynamic studies were conducted in Rh41 tumored-mice using increasing concentrations after a single dose of a pegylated, his-tag version of construct 385A08-Fn0V2B-Cys (50, 100, 200 mpk), or a combination of a mono-specific $^{10}$Fn3-based IGF-IR binder (AT580-PEG40, SEQ ID NO: 27) and a mono-specific $^{10}$Fn3-based VEGFR-2 binder (Peg-V2Bshort, SEQ ID NO: 28) at equivalent doses (25+25, 50+50, 100+100). Tumors were harvested at 1, 6, and 24 hrs after dosing and processed. Equal amounts of protein from each tumor lysate (60 μg) were added to each well of a gel (NuPAGE 4-12% Bis-Tris Gel, Invitrogen, Carlsbad, Calif.). Proteins were separated on a NuPAGE gel, transferred to nitrocellulose membranes (Bio-Rad Laboratories, Hercules, Calif.) and incubated in Odyssey Blocking buffer (Li-Cor Biosciences) for 1 hr at room temperature. Inhibition of phosphorylation of proteins was measured by probing Western blots with phospho-specific antibodies as described above.

Tumor Xenograft Studies RH-41, A549 and GEO, in Mice

Female Balb/c athymic mice (nu/nu), 5-6 weeks of age were purchased from Harlan Sprague-Dawley Co. (Indianapolis, Ind.). Animals were maintained in an ammonia and pathogen-free environment and fed water and food ad libitum. Mice were maintained in quarantine for 7 days prior to tumor implantation and efficacy testing. All animal studies were performed under the approval of the BMS Animal Care and Use committee and in accordance with the American Association for Accreditation of Laboratory Animal Care (AAALAC).

Human tumors Rh-41 (rhabdomyosarcoma), A549 (lung) and GEO (colon) were implanted subcutaneously (sc) as small fragments generally no larger than 0.1 to 0.2 mm$^3$ using a 16 g trocar. All tumors that were evaluated were allowed to grow to an approximate size of 125 mm$^3$ prior at the initiation of treatment. The treatment and control group sizes consisted of 6-8 mice. Tumor size was measured twice weekly. Tumor volume was calculated by measuring perpendicular tumor diameters using Vernier scale calipers and using the formula for an ellipsoid: ½ (length×(width)). Mice were euthanized if the tumor size surpassed 1,500 mm$^3$, if animal weight loss was greater than 20% of the starting weight or if extensive tumor necrosis occurred. All compounds were obtained internally and dosed by intraperitoneal (i.p.) delivery using a 25 g sterile hypodermic needle. Vehicle control solution was generally phosphate buffered saline (PBS) while a mono-specific $^{10}$Fn3-based VEGFR-2 binder (Peg-V2Bshort, SEQ ID NO: 28) was dosed in a formulation of 10 mM Sodium Acetate, 150 mM NaCl, pH 4.5; a mono-specific $^{10}$Fn3-based IGF-IR binder (AT580-PEG40, SEQ ID NO: 27) was formulated in PBS and pegylated, his-tagged construct 385A08-Fn-V2B-cys (SEQ ID NO: 9) was formulated in 50 mM Sodium Acetate, 150 mM NaCl, pH, 4.5.

Anti-tumor efficacy is expressed as percent tumor growth inhibition (% TGI) and calculated as follows:

$$\% \text{ TGI} = \{1 - [(T_t - T_o)/(C_t - C_0)]\} \times 100$$

where $C_t$=the median tumor volume (mm$^3$) of vehicle control (C) mice at time, t; $T_t$=median tumor volume (mm$^3$) of treated mice (T) at time t; $C_0$=median tumor volume (mm$^3$) of vehicle control (C) mice at time 0; $T_t$=median tumor volume (mm$^3$) of treated mice (T) at time 0. Greater than or equal to 50% TGI over one tumor volume doubling time (TVDT) is considered an active anti-tumor response. TVDT is measured over the linear growth range of the tumor, generally between 250 mm$^3$-1000 mm$^3$ tumor size.

Tumor Xenograft Study in A673 Model.

(1) Tumor Cell Line.

Human A673 Ewing Sarcoma cells (CRL-1598) were cultured following the instructions recommended by ATCC. Briefly, cells were maintained in base medium Dulbecco's Modified Eagle's Medium, (Invitrogen, Carlsbad, Calif.), supplemented with 10% fetal bovine serum (Invitrogen, Carlsbad, Calif.) at 37° C. under a 5% CO$_2$ atmosphere.

(2) Xenograft Model.

10×10$^6$ cells resuspended in 0.1 ml of PBS were injected subcutaneously in the dorsal flank region of female, seven to eight-week old, female athymic NCr nude mice (Taconic Farms, Hudson, N.Y.). Mice were housed in microisolator cages under HEPA filtered-air and temperature controlled barrier racks. They were maintained on a 12 h light/dark cycle, fed with irradiated food and autoclaved water available ad libitum, and allowed to adapt to their new environment. Mice were manipulated using aseptic protocols and all experimental procedures and end point of tumor studies followed institutional guidelines. Tumor implantation was monitored using caliper measurements to establish tumor growth rate before randomization and mice were randomized when tumors reached an average of 150-200 mm$^3$. Mice were euthanized when tumors reached a volume of 3,000 mm$^3$.

(3) Treatments.

Mice from each study were assigned to treatment groups described below and received intraperitoneal administration at the regimens indicated below. The vehicle group received a mono-specific $^{10}$Fn3-based VEGFR-2 binder (Peg-V2Bshort, SEQ ID NO: 28) in reconstitution buffer: 10 mM Sodium Acetate, 150 mM NaCl, pH 4.5. A mono-specific $^{10}$Fn3-based IGF-IR binder (AT580-PEG40, SEQ ID NO: 27) was formulated in PBS and pegylated, his-tagged 385A08-Fn-V2B-cys (SEQ ID NO: 9) was formulated in 50 mM Sodium Acetate, 150 mM NaCl, pH, 4.5. For the study described in FIG. 26, there were six treatment groups, each consisting of 9 mice that were dosed on a three times a week (TIW) schedule of either vehicle, 50 mg/kg (mpk) of Peg-V2Bshort, 50 mpk of AT580-PEG40, 50 mpk of pegylated, his-tagged 385A08-Fn-V2B-cys, 100 mpk of pegylated, his-tagged 385A08-Fn-V2B-cys, or a co-dose of 50 mpk of AT580-PEG40 and 50 mpk of Peg-V2Bshort. In the dose response study discussed above (data not shown), there were five treatment groups, each consisting of 9 mice that were dosed on a TIW schedule of either vehicle, or 20, 60, 100, or 200 mpk of pegylated, his-tagged 385A08-Fn-V2B-cys.

(4) Tumor Volume Measurements.

Tumor volume measurements were performed twice a week using Vernier scale calipers and tumor volumes (mm$^3$) were calculated using the ellipsoid formula [$\pi/6$ (L×W$^2$)], where L represents the largest tumor diameter (mm) and W represents the smallest tumor diameter (mm). Tumor measurements were noted as absolute values. Animal body weights were recorded twice a week during the course of the experiment.

(5) Tumor Growth Inhibition (TGI).

TGI was calculated as the percent tumor growth of treated (T) groups from control group (vehicle, C). Tumor growth was calculated by subtracting initial tumor volume (at day 0) from the final tumor volume at the end of the experiment. TGI=(1−[T−T$_0$]/[C−C$_0$])*100.

PK/PD Study Methods for Mouse and Monkey Models
Determination of Concentration in Serum or Plasma A quantitative electrochemiluminescence assay was developed to detect the concentration of 385A08-Fn-V2B-Cys (with and without his tag) in serum or plasma samples. In this assay, a mouse monoclonal antibody specific to the VEGFR2 portion of the molecule was adsorbed to a standard Meso Scale Discovery plate to capture the adnectin overnight at 4° C. The serum/plasma sample was added to the plate for one hour incubation at room temperature. The captured adnectin was detected by a rabbit polyclonal antibody specific to the scaffold region of the adnectin which was co-mixed with a goat anti-rabbit antibody linked with a SULFO-TAG, and added to the plate simultaneously. Following a wash to remove any unbound SULFO-TAG reagent, a read buffer is added to each well and electrochemiluminescense detection is used to detect binding events. 385A08-Fn-V2B-Cys (with and without his tag) plasma/serum concentrations in samples were calculated based on the signal of the sample compared to a 4 parameter fit of a standard curve of 385A08-Fn-V2B-Cys (with and without his tag).

Determination of VEGF-A Concentrations in Mice and Monkeys

A quantitative electrochemiluminescence assay for human and murine VEGF-A from Meso Scale Discovery (Gaithersburg, Md.) was employed to detect VEGF-A plasma concentration according to the manufacturer's instructions. Specific anti-VEGF-A monoclonal antibodies are pre-coated onto Meso Scale Discovery (MSD) plates. The plate is blocked overnight at 4° C. and VEGF-A present in the standards, QCs and samples are captured during a 2 hour incubation step by the immobilized antibody. After washing away any unbound substances, a SULFO-TAG linked polyclonal detection antibody is added to the wells for 2 hours. Following a wash to remove any unbound SULFO-Tag reagent, a read buffer is added to each well and electrochemiluminescense detection is used to detect binding events. Plasma VEGF-A concentrations in samples were calculated based on the signal of the sample compared to a 4 parameter fit of a standard curve.

In Vivo Methods—Mouse

Single-Dose Pharmacokinetics in Mice.

The pharmacokinetics of his-tagged version of 385A08-Fn-V2B-Cys was studied in nude mice. Four groups of non-fasted animals (N=3-4 per group, 20-25 g) received his-tagged version of 385A08-Fn-V2B-Cys either as an intravenous (IV) bolus dose via the tail vein (5 mL/kg) or as an intraperitoneal (IP) dose (10 mL/kg). The doses were 5 and 50 mg/kg for both routes. Prior to dosing, the compound was diluted from a stock solution to an appropriate dosing solution concentration in phosphate buffered saline (PBS). Serial blood samples (~0.05 mL) were obtained by nicking the lateral tail vein. For the IV route, the sampling time points were 0.08, 0.5, 1, 2, 6, 12, 24, 48, 96, and 171 h post dose. For the IP route, the sampling time points were 0.5, 1, 2, 6, 12, 24, 48, 96, 124, and 171 h post dose. Plasma samples were harvested by diluting blood sample into a citrate phosphate dextrose solution in a 1:1 ratio and were stored at −20° C. until analysis.

Single-Dose Pharmacokinetic/Pharmacodynamic Study in Nude Mice Bearing the Rh41 Tumor.

His-tagged version of 385A08-Fn-V2B-Cys was dosed intraperitoneally to non-fasted nude mice (20-25 g) bearing the Rh41 tumor at doses of 20 and 200 mg/kg along with a vehicle group. Prior to dosing, the drug candidate was diluted from a stock solution to an appropriate dosing solution concentration in phosphate buffered saline (PBS). Blood samples were obtained by cardiac puncture at 1, 3, 6, 16, 24, 32, 48, and 80 h post dose in the drug-treated groups and 1, 24, and 36 post dose in the vehicle group. Serum samples were obtained after coagulation and stored at −20° C. until analysis for drug and VEGF-A concentrations.

Single-Dose Pharmacokinetic/Pharmacodynamic Study in Nude Mice Bearing the A673 Tumor.

385A08-Fn-V2B-Cys (non-his tagged) was dosed intraperitoneally to non-fasted nude mice (20-25 g) bearing the A673 tumor at doses of 20 and 200 mg/kg. Prior to dosing, the drug candidate was diluted from a stock solution to an appropriate dosing solution concentration in PBS. Plasma samples were harvested by cardiac puncture into sodium heparin coated BD vacutainer tubes at 1, 3, 6, 16, 24, 32, 48, 72, 96, and 120 h post dose, and were stored at −20° C. until analysis for drug and VEGF-A concentrations.

In Vivo Methods—Monkey

Single-Dose Pharmacokinetic/Pharmacodynamic Study in Monkeys.

The pharmacokinetics of his-tagged version of 385A08-Fn-V2B-Cys was evaluated in male cynomolgus monkeys. Following an overnight fast, 2 animals (~4 kg) received his-tagged version of 385A08-Fn-V2B-Cys at doses of 3 and 30 mg/kg by a constant-rate IV infusion (5 mL/kg) for 10 min via the femoral vein. Prior to dosing, the drug candidate was diluted from a stock solution to an appropriate dosing solution concentration in PBS. Blood samples (~1 mL) were collected into $K_2$EDTA tubes from the femoral artery at predose and 0.17, 0.25, 0.5, 1, 2, 4, 6, 8, 24, 30, 54, 72 (day 3), 96 (day 4), 168 (day 7), 216 (day 9), 264 (day 11), 336 (day 14), 384 (day 16), 432 (day 18), 504 h (day 21) post dose. Plasma samples were obtained after centrifugation at 4° C. (1500-2000×g) and stored at −20° C. until analysis for drug and VEGF-A concentrations.

Using the same study design, 385A08-Fn-V2B-Cys (non-his tagged) was studied at 3 mg/kg following IV administration to male cynomolgus monkeys (N=3, ~4 kg). After the 3-week study and additional 3-week washout period, 385A08-Fn-V2B-Cys (non-his tagged) was re-dosed to the same monkeys at the same dose, with blood samples collected up to a week post dose.

Data Analysis

The data are expressed as mean±standard deviation (SD).

The pharmacokinetic parameters of 385A08-Fn-V2B-Cys (his tagged and non-his tagged) were obtained by non-compartmental analysis of plasma (serum) concentration vs. time data (KINETICA™ software, Version 4.2, InnaPhase Corporation, Philadelphia, Pa.). The peak concentration (Cmax) and time for Cmax were recorded directly from experimental observations. The area under the curve from time zero to the last sampling time (AUC(0-T)) and the area under the curve from time zero to infinity (AUC(INF)) were calculated using a combination of linear and log trapezoidal summations. The total plasma clearance (CLTp), steady-state volume of distribution (Vss), terminal half-life (T½) and mean residence time (MRT) were estimated after IV administration. Estimations of AUC and T½ were made using a minimum of 3 time points with quantifiable concentrations.

The pharmacokinetic (PK) and pharmacodynamic (PD) data of 385A08-Fn-V2B-Cys (his tagged and non-his tagged) generated in mice and monkeys were modeled using the SAAM II (version 1.2.1, Seattle, Wash.). For the mouse PK data obtained after IV and IP doses of 5 and 50 mg/kg, the naive-pooled serum concentration-time data were simultaneously fitted using a two-compartment model coupled with first-order absorption kinetics.

The PD response, measured as either mVEGF-A or hVEGF-A concentrations in plasma or serum, was modeled using an indirect response model, with the assumptions that the production of VEGF-A was not altered in the presence of 385A08-Fn-V2B-Cys (his tagged and non-his tagged) and binding of VEGF-A to VEGFR-2, as its major clearance pathway, was blocked by 385A08-Fn-V2B-Cys (his tagged and non-his tagged).

We claim:

1. A polypeptide comprising:
   (I) (a) an N-terminal domain comprising a first fibronectin type III tenth domain ($^{10}$Fn3) which binds to IGF-1R, wherein the $^{10}$Fn3 domain comprises BC, DE, and FG loops comprising the amino acid sequence set forth in SEQ ID NOs: 2, 3, and 4, respectively; and
   (b) a C-terminal domain comprising a second $^{10}$Fn3 domain which binds to vascular endothelial growth factor receptor 2 (VEGFR2), wherein the second $^{10}$Fn3 domain comprises BC, DE, and FG loops comprising the amino acid sequence set forth in SEQ ID NOs: 5, 6, and 7, respectively; or
   (II) (a) an N-terminal domain comprising a first $^{10}$Fn3 domain which binds to VEGFR2, wherein the $^{10}$Fn3 domain comprises BC, DE, and FG loops comprising the amino acid sequence set forth in SEQ ID NOs: 5, 6, and 7, respectively; and
   (b) a C-terminal domain comprising a second $^{10}$Fn3 domain which binds to IGF-1R, wherein the second $^{10}$Fn3 domain comprises BC, DE, and FG loops comprising the amino acid sequence set forth in SEQ ID NOs: 2, 3, and 4, respectively.

2. The polypeptide of claim 1, wherein the first and/or second $^{10}$Fn3 domain comprises an N-terminal extension sequence selected from the group consisting of M, MG, G, or SEQ ID NO: 45, 46, or 48.

3. The polypeptide of claim 1, wherein the first and/or second $^{10}$Fn3 domain is linked at its C-terminus to the amino acid sequence of E, EI, ES, EC, EGS, EGC, EID, SEQ ID NO: 17, SEQ ID NO: 18, SEQ ID NO: 19, SEQ ID NO: 50, SEQ ID NO: 51, SEQ ID NO: 52, SEQ ID NO: 71, or SEQ ID NO: 72.

4. The polypeptide of claim 1, further comprising one or more pharmacokinetic (PK) moieties selected from the group consisting of: a polyoxyalkylene moiety, a human serum albumin binding protein, sialic acid, human serum albumin, IgG, an IgG binding protein, transferrin, and an Fc fragment.

5. The polypeptide of claim 4, wherein the PK moiety and the polypeptide are linked via at least one disulfide bond, a peptide bond, a polypeptide, a polymeric sugar, or a polyethylene glycol moiety.

6. The polypeptide of claim 1, wherein said polypeptide has been deimmunized to remove one or more T-cell epitopes.

7. A pharmaceutically acceptable composition comprising the polypeptide of claim 1.

8. The polypeptide of claim 1, wherein the IGF-IR binding $^{10}$Fn3 domain binds to IGF-IR with a $K_D$ of less than 500 nM.

9. The polypeptide of claim 1, wherein the VEGFR2 binding $^{10}$Fn3 domain binds to VEGFR2 with a $K_D$ of less than 500 nM.

10. The polypeptide of claim 1, wherein the first $^{10}$Fn3 domain and second $^{10}$Fn3 domain are linked via a polypeptide selected from a glycine-serine based linker, a glycine-proline based linker, a proline-alanine based linker, or a polypeptide comprising the amino acid sequence of SEQ ID NO: 20.

* * * * *

SEQUENCE LISTING

```
<160> NUMBER OF SEQ ID NOS: 72

<210> SEQ ID NO 1
<211> LENGTH: 94
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Trp Ser Ala Arg Leu Lys Val Ala Arg
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Lys Asn Val Tyr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Arg Phe Arg Asp Tyr Gln Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Trp Arg His Pro His Phe Pro Thr Arg
1               5                   10
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Leu Gln Pro Pro Thr
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Asp Gly Arg Asn Gly Arg Leu Leu Ser Ile Pro
1               5                   10

<210> SEQ ID NO 8
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Thr Ser Thr Ser Thr Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
    130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr Glu Ile Asp Lys Pro Ser Gln
        195                 200

```
<210> SEQ ID NO 9
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Thr Ser Thr Ser Thr Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
    130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr Glu Ile Asp Lys Pro Cys Gln
        195                 200

<210> SEQ ID NO 10
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Val Ser Asp Val Pro Arg
```

```
                    100                 105                 110
Asp Leu Glu Val Val Ala Ala Thr Pro Thr Ser Leu Leu Ile Ser Trp
            115                 120                 125

Arg His Pro His Phe Pro Thr Arg Tyr Tyr Arg Ile Thr Tyr Gly Glu
        130                 135                 140

Thr Gly Gly Asn Ser Pro Val Gln Glu Phe Thr Val Pro Leu Gln Pro
145                 150                 155                 160

Pro Thr Ala Thr Ile Ser Gly Leu Lys Pro Gly Val Asp Tyr Thr Ile
                165                 170                 175

Thr Val Tyr Ala Val Thr Asp Gly Arg Asn Gly Arg Leu Leu Ser Ile
            180                 185                 190

Pro Ile Ser Ile Asn Tyr Arg Thr Glu Ile Asp Lys Pro Ser Gln
        195                 200                 205

<210> SEQ ID NO 11
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Arg His Pro His Phe Pro
    130                 135                 140

Thr Arg Tyr Tyr Arg Ile Thr Tyr Gly Glu Thr Gly Gly Asn Ser Pro
145                 150                 155                 160

Val Gln Glu Phe Thr Val Pro Leu Gln Pro Pro Thr Ala Thr Ile Ser
                165                 170                 175

Gly Leu Lys Pro Gly Val Asp Tyr Thr Ile Thr Val Tyr Ala Val Thr
            180                 185                 190

Asp Gly Arg Asn Gly Arg Leu Leu Ser Ile Pro Ile Ser Ile Asn Tyr
        195                 200                 205

Arg Thr Glu Ile Asp Lys Pro Ser Gln
    210                 215

<210> SEQ ID NO 12
<211> LENGTH: 204
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 12

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Asp Lys Pro Ser Thr Ser Thr Ser Thr Val Ser Asp Val Pro
            100                 105                 110

Arg Asp Leu Glu Val Val Ala Ala Thr Pro Thr Ser Leu Leu Ile Ser
        115                 120                 125

Trp Ser Ala Arg Leu Lys Val Ala Arg Tyr Tyr Arg Ile Thr Tyr Gly
    130                 135                 140

Glu Thr Gly Gly Asn Ser Pro Val Gln Glu Phe Thr Val Pro Lys Asn
145                 150                 155                 160

Val Tyr Thr Ala Thr Ile Ser Gly Leu Lys Pro Gly Val Asp Tyr Thr
                165                 170                 175

Ile Thr Val Tyr Ala Val Thr Arg Phe Arg Asp Tyr Gln Pro Ile Ser
            180                 185                 190

Ile Asn Tyr Arg Thr Glu Ile Asp Lys Pro Ser Gln
        195                 200

<210> SEQ ID NO 13
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Asp Lys Pro Ser Thr Ser Thr Ser Thr Val Ser Asp Val Pro
            100                 105                 110

Arg Asp Leu Glu Val Val Ala Ala Thr Pro Thr Ser Leu Leu Ile Ser
        115                 120                 125

```
Trp Ser Ala Arg Leu Lys Val Ala Arg Tyr Tyr Arg Ile Thr Tyr Gly
        130                 135                 140

Glu Thr Gly Gly Asn Ser Pro Val Gln Glu Phe Thr Val Pro Lys Asn
145                 150                 155                 160

Val Tyr Thr Ala Thr Ile Ser Gly Leu Lys Pro Gly Val Asp Tyr Thr
                165                 170                 175

Ile Thr Val Tyr Ala Val Thr Arg Phe Arg Asp Tyr Gln Pro Ile Ser
                180                 185                 190

Ile Asn Tyr Arg Thr Glu Ile Asp Lys Pro Cys Gln
            195                 200

<210> SEQ ID NO 14
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
                20                  25                  30

Tyr Tyr Arg Ile Thr Tyr Gly Glu Thr Gly Gly Asn Ser Pro Val Gln
            35                  40                  45

Glu Phe Thr Val Pro Leu Gln Pro Pro Thr Ala Thr Ile Ser Gly Leu
50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Asp Lys Gly Ser Gly Ser Gly Ser Gly Ser Gly Ser Val Ser
                100                 105                 110

Asp Val Pro Arg Asp Leu Glu Val Val Ala Ala Thr Pro Thr Ser Leu
            115                 120                 125

Leu Ile Ser Trp Ser Ala Arg Leu Lys Val Ala Arg Tyr Tyr Arg Ile
        130                 135                 140

Thr Tyr Gly Glu Thr Gly Gly Asn Ser Pro Val Gln Glu Phe Thr Val
145                 150                 155                 160

Pro Lys Asn Val Tyr Thr Ala Thr Ile Ser Gly Leu Lys Pro Gly Val
                165                 170                 175

Asp Tyr Thr Ile Thr Val Tyr Ala Val Thr Arg Phe Arg Asp Tyr Gln
                180                 185                 190

Pro Ile Ser Ile Asn Tyr Arg Thr Glu Ile Asp Lys Pro Ser Gln
            195                 200                 205

<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Val Ser Asp Val Pro Arg Asp Leu Glu Val Val Ala Ala Thr
1               5                   10                  15
```

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
            35                  40                  45

Glu Phe Thr Val Pro Leu Gln Pro Pro Thr Ala Thr Ile Ser Gly Leu
 50                  55                  60

Lys Pro Gly Val Asp Tyr Thr Ile Thr Val Tyr Ala Val Thr Asp Gly
 65                  70                  75                  80

Arg Asn Gly Arg Leu Leu Ser Ile Pro Ile Ser Ile Asn Tyr Arg Thr
                85                  90                  95

Glu Ile Asp Lys Gly Ser Gly Ser Gly Ser Gly Ser Gly Ser Gly Ser
            100                 105                 110

Gly Ser Gly Ser Gly Ser Gly Ser Val Ser Asp Val Pro Arg Asp Leu
            115                 120                 125

Glu Val Val Ala Ala Thr Pro Thr Ser Leu Leu Ile Ser Trp Ser Ala
 130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
            165                 170                 175

Ala Thr Ile Ser Gly Leu Lys Pro Gly Val Asp Tyr Thr Ile Thr Val
            180                 185                 190

Tyr Ala Val Thr Arg Phe Arg Asp Tyr Gln Pro Ile Ser Ile Asn Tyr
            195                 200                 205

Arg Thr Glu Ile Asp Lys Pro Ser Gln
 210                 215

<210> SEQ ID NO 16
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Val Ser Asp Val Pro Arg Asp Leu Glu Val Val Ala Ala Thr
 1               5                  10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
            35                  40                  45

Glu Phe Thr Val Pro Leu Gln Pro Pro Thr Ala Thr Ile Ser Gly Leu
 50                  55                  60

Lys Pro Gly Val Asp Tyr Thr Ile Thr Val Tyr Ala Val Thr Asp Gly
 65                  70                  75                  80

Arg Asn Gly Arg Leu Leu Ser Ile Pro Ile Ser Ile Asn Tyr Arg Thr
                85                  90                  95

Glu Ile Asp Lys Pro Ser Gln
            100

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 17

Glu Ile Asp Lys Pro Ser Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Ile Asp Lys Pro Cys Gln
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Ile Asp Lys
1

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Ser Thr Ser Thr Ser Thr
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Gly Ser Gly Ser Gly Ser Gly Ser
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Gly Ser Gly Ser Gly Ser Gly Ser Gly Ser Gly Ser Gly Ser
1               5                   10                  15

Gly Ser Gly Ser
            20
```

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Gly Gly Gly Ser Gly Gly Gly Gly Ser Gly Gly Gly Ser Gly
1               5                   10                  15

<210> SEQ ID NO 26
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
        50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Gln

<210> SEQ ID NO 27
<211> LENGTH: 99

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Val Ser Asp Val Pro Arg Asp Leu Glu Val Val Ala Ala Thr
1               5                  10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Cys Gln

<210> SEQ ID NO 28
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Glu Val Val Ala Ala Thr Pro Thr Ser Leu Leu Ile Ser Trp Arg
1               5                  10                  15

His Pro His Phe Pro Thr Arg Tyr Tyr Arg Ile Thr Tyr Gly Glu Thr
            20                  25                  30

Gly Gly Asn Ser Pro Val Gln Glu Phe Thr Val Pro Leu Gln Pro Pro
        35                  40                  45

Thr Ala Thr Ile Ser Gly Leu Lys Pro Gly Val Asp Tyr Thr Ile Thr
    50                  55                  60

Val Tyr Ala Val Thr Asp Gly Arg Asn Gly Arg Leu Leu Ser Ile Pro
65                  70                  75                  80

Ile Ser Ile Asn Tyr Arg Thr Glu Ile Asp Lys Pro Cys Gln
                85                  90

<210> SEQ ID NO 29
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Val Ser Asp Val Pro Arg Asp Leu Glu Val Val Ala Ala Thr
1               5                  10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60
```

```
Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Gly Pro Gly Val
                 85                  90                  95

Ser Asp Val Pro Arg Asp Leu Glu Val Val Ala Ala Thr Pro Thr Ser
            100                 105                 110

Leu Leu Ile Ser Trp Arg His Pro His Phe Pro Thr Arg Tyr Tyr Arg
        115                 120                 125

Ile Thr Tyr Gly Glu Thr Gly Gly Asn Ser Pro Val Gln Glu Phe Thr
130                 135                 140

Val Pro Leu Gln Pro Pro Thr Ala Thr Ile Ser Gly Leu Lys Pro Gly
145                 150                 155                 160

Val Asp Tyr Thr Ile Thr Val Tyr Ala Val Thr Asp Gly Arg Asn Gly
                165                 170                 175

Arg Leu Leu Ser Ile Pro Ile Ser Ile Asn Tyr Arg Thr
            180                 185
```

<210> SEQ ID NO 30
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Gly Val Ser Asp Val Pro Arg Asp Leu Glu Val Val Ala Ala Thr
 1               5                  10                  15

Pro Thr Ser Leu Leu Ile Ser Trp Ser Ala Arg Leu Lys Val Ala Arg
                 20                  25                  30

Tyr Tyr Arg Ile Thr Tyr Gly Glu Thr Gly Gly Asn Ser Pro Val Gln
             35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Gly Pro Gly Pro
                 85                  90                  95

Gly Pro Gly Val Ser Asp Val Pro Arg Asp Leu Glu Val Val Ala Ala
            100                 105                 110

Thr Pro Thr Ser Leu Leu Ile Ser Trp Arg His Pro His Phe Pro Thr
        115                 120                 125

Arg Tyr Tyr Arg Ile Thr Tyr Gly Glu Thr Gly Gly Asn Ser Pro Val
130                 135                 140

Gln Glu Phe Thr Val Pro Leu Gln Pro Pro Thr Ala Thr Ile Ser Gly
145                 150                 155                 160

Leu Lys Pro Gly Val Asp Tyr Thr Ile Thr Val Tyr Ala Val Thr Asp
                165                 170                 175

Gly Arg Asn Gly Arg Leu Leu Ser Ile Pro Ile Ser Ile Asn Tyr Arg
            180                 185                 190

Thr
```

<210> SEQ ID NO 31
<211> LENGTH: 197
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 31

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Asn Ser Pro Val Gln
        35                  40                  45

Glu Phe Thr Val Pro Lys Asn Val Tyr Thr Ala Thr Ile Ser Gly Leu
50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Gly Pro Gly Pro
                85                  90                  95

Gly Pro Gly Pro Gly Pro Gly Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr
            195

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Gly
1

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Pro Gly Pro Gly Pro Gly
1               5

<210> SEQ ID NO 34
<211> LENGTH: 11
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 34

Gly Pro Gly Pro Gly Pro Gly Pro Gly Pro Gly
1               5                   10

<210> SEQ ID NO 35
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Val Ala Ala Thr Pro Thr Ser Leu Leu Ile Ser Trp Ser Ala
1               5                   10                  15

Arg Leu Lys Val Ala Arg Tyr Tyr Arg Ile Thr Tyr Gly Glu Thr Gly
                20                  25                  30

Gly Asn Ser Pro Val Gln Glu Phe Thr Val Pro Lys Asn Val Tyr Thr
            35                  40                  45

Ala Thr Ile Ser Gly Leu Lys Pro Gly Val Asp Tyr Thr Ile Thr Val
        50                  55                  60

Tyr Ala Val Thr Arg Phe Arg Asp Tyr Gln Pro Ile Ser Ile Asn Tyr
65                  70                  75                  80

Arg Thr

<210> SEQ ID NO 36
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
        50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr
                85                  90

<210> SEQ ID NO 37
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Val Ser Asp Val Pro Arg Asp Leu Glu Val Val Ala Ala Thr
1               5                   10                  15
```

```
Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                    85                  90                  95
```

<210> SEQ ID NO 38
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Pro Ser
                85                  90                  95

Gln
```

<210> SEQ ID NO 39
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Arg Phe Arg Asp
 65                  70                  75                  80

Tyr Gln Pro Ile Ser Ile Asn Tyr Arg Thr Glu Ile Asp Lys Pro Cys
                85                  90                  95

Gln
```

<210> SEQ ID NO 40

```
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
50                  55                  60

Tyr Ala Val Thr Asp Gly Arg Asn Gly Arg Leu Leu Ser Ile Pro Ile
65                  70                  75                  80

Ser Ile Asn Tyr Arg Thr
                85

<210> SEQ ID NO 41
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Val Tyr Ala Val Thr Asp Gly Arg Asn
65                  70                  75                  80

Gly Arg Leu Leu Ser Ile Pro Ile Ser Ile Asn Tyr Arg Thr
                85                  90

<210> SEQ ID NO 42
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60
```

-continued

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Asp Lys
            100

<210> SEQ ID NO 43
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
    50                  55                  60

Gly Val Asp Tyr Thr Ile Thr Val Tyr Ala Val Thr Asp Gly Arg Asn
65                  70                  75                  80

Gly Arg Leu Leu Ser Ile Pro Ile Ser Ile Asn Tyr Arg Thr Glu Ile
                85                  90                  95

Asp Lys Pro Ser Gln
            100

<210> SEQ ID NO 44
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Pro Thr Ala Thr Ile Ser Gly Leu Lys Pro
    50                  55                  60

Gly Val Asp Tyr Thr Ile Thr Val Tyr Ala Val Thr Asp Gly Arg Asn
65                  70                  75                  80

Gly Arg Leu Leu Ser Ile Pro Ile Ser Ile Asn Tyr Arg Thr Glu Ile
                85                  90                  95

Asp Lys Pro Cys Gln
            100

<210> SEQ ID NO 45
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 45

Met Gly Val Ser Asp Val Pro Arg Asp Leu
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Ser Asp Val Pro Arg Asp Leu
1               5

<210> SEQ ID NO 47
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid and this region may encompass 1
      to 15 residues
<220> FEATURE:
<221> NAME/KEY: MOD_RES
<222> LOCATION: (26)..(35)
<223> OTHER INFORMATION: Any amino acid and this region may encompass 0
      to 10 residues
<220> FEATURE:
<221> NAME/KEY: MOD_RES
<222> LOCATION: (46)..(55)
<223> OTHER INFORMATION: Any amino acid and this region may encompass 0
      to 10 residues
<220> FEATURE:
<221> NAME/KEY: MOD_RES
<222> LOCATION: (64)..(83)
<223> OTHER INFORMATION: Any amino acid and this region may encompass 2
      to 20 residues
<220> FEATURE:
<221> NAME/KEY: MOD_RES
<222> LOCATION: (89)..(98)
<223> OTHER INFORMATION: Any amino acid and this region may encompass 0
      to 10 residues
<220> FEATURE:
<221> NAME/KEY: MOD_RES
<222> LOCATION: (105)..(114)
<223> OTHER INFORMATION: Any amino acid and this region may encompass 0
      to 10 residues
<220> FEATURE:
<221> NAME/KEY: MOD_RES
<222> LOCATION: (118)..(137)
<223> OTHER INFORMATION: Any amino acid and this region may encompass 2
      to 20 residues
<220> FEATURE:
<221> NAME/KEY: MOD_RES
<222> LOCATION: (147)..(156)
<223> OTHER INFORMATION: Any amino acid and this region may encompass 0
      to 10 residues
<220> FEATURE:
<221> NAME/KEY: MOD_RES
<222> LOCATION: (169)..(178)
<223> OTHER INFORMATION: Any amino acid and this region may encompass 0
      to 10 residues
<220> FEATURE:
<223> OTHER INFORMATION: See specification as filed for detailed
      description of substitutions and preferred embodiments
```

-continued

```
<400> SEQUENCE: 47

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Arg His Pro His Phe Pro Thr Arg Xaa Xaa Xaa
        35                  40                  45

Xaa Xaa Xaa Xaa Xaa Xaa Xaa Tyr Tyr Arg Ile Thr Tyr Gly Glu Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
                85                  90                  95

Xaa Xaa Pro Leu Gln Pro Pro Thr Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa
        115                 120                 125

Xaa Xaa Xaa Xaa Xaa Xaa Xaa Xaa Xaa Asp Tyr Thr Ile Thr Val Tyr
    130                 135                 140

Ala Val Xaa Xaa Xaa Xaa Xaa Xaa Xaa Xaa Xaa Thr Asp Gly Arg
145                 150                 155                 160

Asn Gly Arg Leu Leu Ser Ile Pro Xaa Xaa Xaa Xaa Xaa Xaa Xaa
                165                 170                 175

Xaa Xaa Ile Ser Ile Asn Tyr Arg Thr
            180                 185

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Val Ser Asp Val Pro Arg Asp Leu
1               5

<210> SEQ ID NO 49
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid and this region may encompass 1
      to 15 residues
<220> FEATURE:
<221> NAME/KEY: MOD_RES
<222> LOCATION: (26)..(35)
<223> OTHER INFORMATION: Any amino acid and this region may encompass 0
      to 10 residues
<220> FEATURE:
<221> NAME/KEY: MOD_RES
<222> LOCATION: (46)..(55)
<223> OTHER INFORMATION: Any amino acid and this region may encompass 0
      to 10 residues
<220> FEATURE:
<221> NAME/KEY: MOD_RES
<222> LOCATION: (64)..(83)
<223> OTHER INFORMATION: Any amino acid and this region may encompass 2
```

```
      to 20 residues
<220> FEATURE:
<221> NAME/KEY: MOD_RES
<222> LOCATION: (89)..(98)
<223> OTHER INFORMATION: Any amino acid and this region may encompass 0
      to 10 residues
<220> FEATURE:
<221> NAME/KEY: MOD_RES
<222> LOCATION: (105)..(114)
<223> OTHER INFORMATION: Any amino acid and this region may encompass 0
      to 10 residues
<220> FEATURE:
<221> NAME/KEY: MOD_RES
<222> LOCATION: (118)..(137)
<223> OTHER INFORMATION: Any amino acid and this region may encompass 2
      to 20 residues
<220> FEATURE:
<221> NAME/KEY: MOD_RES
<222> LOCATION: (147)..(156)
<223> OTHER INFORMATION: Any amino acid and this region may encompass 0
      to 10 residues
<220> FEATURE:
<221> NAME/KEY: MOD_RES
<222> LOCATION: (165)..(174)
<223> OTHER INFORMATION: Any amino acid and this region may encompass 0
      to 10 residues
<220> FEATURE:
<223> OTHER INFORMATION: See specification as filed for detailed
      description of substitutions and preferred embodiments

<400> SEQUENCE: 49

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
            20                  25                  30

Xaa Xaa Xaa Ser Trp Ser Ala Arg Leu Lys Val Ala Arg Xaa Xaa Xaa
            35                  40                  45

Xaa Xaa Xaa Xaa Xaa Xaa Xaa Tyr Tyr Arg Ile Thr Tyr Gly Glu Xaa
            50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Gln Glu Phe Thr Val Xaa Xaa Xaa Xaa Xaa Xaa Xaa
                85                  90                  95

Xaa Xaa Pro Lys Asn Val Tyr Thr Xaa Xaa Xaa Xaa Xaa Xaa Xaa
            100                 105                 110

Xaa Xaa Ala Thr Ile Xaa Xaa Xaa Xaa Xaa Xaa Xaa Xaa Xaa Xaa
            115                 120                 125

Xaa Xaa Xaa Xaa Xaa Xaa Xaa Xaa Asp Tyr Thr Ile Thr Val Tyr
130                 135                 140

Ala Val Xaa Xaa Xaa Xaa Xaa Xaa Xaa Xaa Xaa Thr Arg Phe Arg
145                 150                 155                 160

Asp Tyr Gln Pro Xaa Xaa Xaa Xaa Xaa Xaa Xaa Xaa Xaa Ile Ser
                165                 170                 175

Ile Asn Tyr Arg Thr
            180

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

```
Glu Ile Asp Lys Pro
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Ile Asp Lys Pro Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Ile Asp Lys Pro Cys
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present

<400> SEQUENCE: 53

Met Gly Ser Asp Val Pro Arg Asp Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present

<400> SEQUENCE: 54

Met Gly Asp Val Pro Arg Asp Leu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
```

```
<400> SEQUENCE: 55

Met Gly Val Pro Arg Asp Leu
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present

<400> SEQUENCE: 56

Met Gly Pro Arg Asp Leu
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present

<400> SEQUENCE: 57

Met Gly Arg Asp Leu
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 58

Met Gly Asp Leu
1

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

His His His His His His
1               5

<210> SEQ ID NO 60
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 60

Pro Ala Pro Ala Pro Ala
1               5

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Ala Pro Ala Pro Ala Pro Ala Pro Ala Pro Ala
1               5                   10

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Ala Pro Ala Pro Ala Pro Ala Pro Ala Pro Ala Pro Ala Pro Ala
1               5                   10                  15

Pro Ala

<210> SEQ ID NO 63
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ser Thr
                85                  90                  95

Ser Thr Ser Thr Val Ser Asp Val Pro Arg Asp Leu Glu Val Val Ala
            100                 105                 110

Ala Thr Pro Thr Ser Leu Leu Ile Ser Trp Arg His Pro His Phe Pro
        115                 120                 125

Thr Arg Tyr Tyr Arg Ile Thr Tyr Gly Glu Thr Gly Gly Asn Ser Pro
    130                 135                 140

Val Gln Glu Phe Thr Val Pro Leu Gln Pro Pro Thr Ala Thr Ile Ser
145                 150                 155                 160
```

```
Gly Leu Lys Pro Gly Val Asp Tyr Thr Ile Thr Val Tyr Ala Val Thr
                165                 170                 175

Asp Gly Arg Asn Gly Arg Leu Leu Ser Ile Pro Ile Ser Ile Asn Tyr
            180                 185                 190

Arg Thr Glu Gly Ser Gly Ser
        195

<210> SEQ ID NO 64
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ser Thr
                85                  90                  95

Ser Thr Ser Thr Val Ser Asp Val Pro Arg Asp Leu Glu Val Val Ala
            100                 105                 110

Ala Thr Pro Thr Ser Leu Leu Ile Ser Trp Arg His Pro His Phe Pro
        115                 120                 125

Thr Arg Tyr Tyr Arg Ile Thr Tyr Gly Glu Thr Gly Gly Asn Ser Pro
    130                 135                 140

Val Gln Glu Phe Thr Val Pro Leu Gln Pro Pro Thr Ala Thr Ile Ser
145                 150                 155                 160

Gly Leu Lys Pro Gly Val Asp Tyr Thr Ile Thr Val Tyr Ala Val Thr
                165                 170                 175

Asp Gly Arg Asn Gly Arg Leu Leu Ser Ile Pro Ile Ser Ile Asn Tyr
            180                 185                 190

Arg Thr Glu Gly Ser Gly Cys
        195

<210> SEQ ID NO 65
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45
```

```
Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Pro Ala Pro
                 85                  90                  95

Ala Pro Ala Val Ser Asp Val Pro Arg Asp Leu Glu Val Val Ala Ala
                100                 105                 110

Thr Pro Thr Ser Leu Leu Ile Ser Trp Arg His Pro His Phe Pro Thr
            115                 120                 125

Arg Tyr Tyr Arg Ile Thr Tyr Gly Glu Thr Gly Gly Asn Ser Pro Val
        130                 135                 140

Gln Glu Phe Thr Val Pro Leu Gln Pro Pro Thr Ala Thr Ile Ser Gly
145                 150                 155                 160

Leu Lys Pro Gly Val Asp Tyr Thr Ile Thr Val Tyr Ala Val Thr Asp
                165                 170                 175

Gly Arg Asn Gly Arg Leu Leu Ser Ile Pro Ile Ser Ile Asn Tyr Arg
                180                 185                 190

Thr Glu Gly Ser Gly Ser
            195
```

```
<210> SEQ ID NO 66
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Gly Val Ser Asp Val Pro Arg Asp Leu Glu Val Val Ala Ala Thr
  1               5                  10                  15

Pro Thr Ser Leu Leu Ile Ser Trp Ser Ala Arg Leu Lys Val Ala Arg
             20                  25                  30

Tyr Tyr Arg Ile Thr Tyr Gly Glu Thr Gly Gly Asn Ser Pro Val Gln
         35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Pro Ala Pro
                 85                  90                  95

Ala Pro Ala Val Ser Asp Val Pro Arg Asp Leu Glu Val Val Ala Ala
                100                 105                 110

Thr Pro Thr Ser Leu Leu Ile Ser Trp Arg His Pro His Phe Pro Thr
            115                 120                 125

Arg Tyr Tyr Arg Ile Thr Tyr Gly Glu Thr Gly Gly Asn Ser Pro Val
        130                 135                 140

Gln Glu Phe Thr Val Pro Leu Gln Pro Pro Thr Ala Thr Ile Ser Gly
145                 150                 155                 160

Leu Lys Pro Gly Val Asp Tyr Thr Ile Thr Val Tyr Ala Val Thr Asp
                165                 170                 175

Gly Arg Asn Gly Arg Leu Leu Ser Ile Pro Ile Ser Ile Asn Tyr Arg
                180                 185                 190

Thr Glu Gly Ser Gly Cys
```

<210> SEQ ID NO 67
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Val Ser Asp Val Pro Arg Asp
            100                 105                 110

Leu Glu Val Val Ala Ala Thr Pro Thr Ser Leu Leu Ile Ser Trp Arg
            115                 120                 125

His Pro His Phe Pro Thr Arg Tyr Tyr Arg Ile Thr Tyr Gly Glu Thr
        130                 135                 140

Gly Gly Asn Ser Pro Val Gln Glu Phe Thr Val Pro Leu Gln Pro Pro
145                 150                 155                 160

Thr Ala Thr Ile Ser Gly Leu Lys Pro Gly Val Asp Tyr Thr Ile Thr
                165                 170                 175

Val Tyr Ala Val Thr Asp Gly Arg Asn Gly Arg Leu Leu Ser Ile Pro
            180                 185                 190

Ile Ser Ile Asn Tyr Arg Thr Glu Gly Ser Gly Ser
        195                 200

<210> SEQ ID NO 68
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro

```
                    85                  90                  95
Ala Pro Ala Pro Ala Pro Ala Pro Ala Val Ser Asp Val Pro Arg Asp
                100                 105                 110

Leu Glu Val Val Ala Ala Thr Pro Thr Ser Leu Leu Ile Ser Trp Arg
            115                 120                 125

His Pro His Phe Pro Thr Arg Tyr Tyr Arg Ile Thr Tyr Gly Glu Thr
        130                 135                 140

Gly Gly Asn Ser Pro Val Gln Glu Phe Thr Val Pro Leu Gln Pro Pro
145                 150                 155                 160

Thr Ala Thr Ile Ser Gly Leu Lys Pro Gly Val Asp Tyr Thr Ile Thr
                165                 170                 175

Val Tyr Ala Val Thr Asp Gly Arg Asn Gly Arg Leu Leu Ser Ile Pro
            180                 185                 190

Ile Ser Ile Asn Tyr Arg Thr Glu Gly Ser Gly Cys
        195                 200

<210> SEQ ID NO 69
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Pro Ala Pro Ala Pro Ala Pro Ala Val
                100                 105                 110

Ser Asp Val Pro Arg Asp Leu Glu Val Val Ala Ala Thr Pro Thr Ser
            115                 120                 125

Leu Leu Ile Ser Trp Arg His Pro His Phe Pro Thr Arg Tyr Tyr Arg
        130                 135                 140

Ile Thr Tyr Gly Glu Thr Gly Gly Asn Ser Pro Val Gln Glu Phe Thr
145                 150                 155                 160

Val Pro Leu Gln Pro Pro Thr Ala Thr Ile Ser Gly Leu Lys Pro Gly
                165                 170                 175

Val Asp Tyr Thr Ile Thr Val Tyr Ala Val Thr Asp Gly Arg Asn Gly
            180                 185                 190

Arg Leu Leu Ser Ile Pro Ile Ser Ile Asn Tyr Arg Thr Glu Gly Ser
        195                 200                 205

Gly Ser
    210

<210> SEQ ID NO 70
<211> LENGTH: 210
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Pro Ala Pro
                85                  90                  95

Ala Pro Ala Pro Ala Pro Ala Pro Ala Pro Ala Pro Ala Pro Ala Val
            100                 105                 110

Ser Asp Val Pro Arg Asp Leu Glu Val Val Ala Ala Thr Pro Thr Ser
        115                 120                 125

Leu Leu Ile Ser Trp Arg His Pro His Phe Pro Thr Arg Tyr Tyr Arg
    130                 135                 140

Ile Thr Tyr Gly Glu Thr Gly Gly Asn Ser Pro Val Gln Glu Phe Thr
145                 150                 155                 160

Val Pro Leu Gln Pro Pro Thr Ala Thr Ile Ser Gly Leu Lys Pro Gly
                165                 170                 175

Val Asp Tyr Thr Ile Thr Val Tyr Ala Val Thr Asp Gly Arg Asn Gly
            180                 185                 190

Arg Leu Leu Ser Ile Pro Ile Ser Ile Asn Tyr Arg Thr Glu Gly Ser
        195                 200                 205

Gly Cys
    210

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Gly Ser Gly Ser
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Gly Ser Gly Cys
1               5